(12) United States Patent
Richardson et al.

(10) Patent No.: US 11,066,655 B2
(45) Date of Patent: *Jul. 20, 2021

(54) RNA POLYMERASE, METHODS OF PURIFICATION AND METHODS OF USE

(71) Applicant: President and Fellows of Harvard College, Cambridge, MA (US)

(72) Inventors: Charles C. Richardson, Newton, MA (US); Bin Zhu, Malden, MA (US); Stanley Tabor, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/042,660

(22) Filed: Feb. 12, 2016

(65) Prior Publication Data

US 2016/0369248 A1    Dec. 22, 2016

Related U.S. Application Data

(63) Continuation of application No. PCT/US2014/051506, filed on Aug. 18, 2014.

(60) Provisional application No. 61/952,192, filed on Mar. 13, 2014, provisional application No. 61/866,657, filed on Aug. 16, 2013.

(51) Int. Cl.
  *C12N 9/12* (2006.01)
  *C12P 19/34* (2006.01)
  *C12Q 1/6895* (2018.01)

(52) U.S. Cl.
  CPC ............ *C12N 9/1247* (2013.01); *C12P 19/34* (2013.01); *C12Q 1/6895* (2013.01); *C12Y 207/07006* (2013.01)

(58) Field of Classification Search
  CPC ................... C12N 9/1247; C12P 19/34; C12Y 207/07006
  See application file for complete search history.

(56) References Cited

U.S. PATENT DOCUMENTS 7,507,567 B2 *  3/2009  Sugiyama ............ C12N 9/1247
                                                           435/183
8,101,385 B2 *  1/2012  Cload .................. C12N 9/1247
                                                           435/6.12

OTHER PUBLICATIONS

Pope et al., Journal of Molecular Biology, vol. 368, pp. 966-981, 2007.*
Pope et al., Genbank Accession No. YP 001285424, Apr. 2009.*
Ikeda et al., Biochemistry, vol. 31, pp. 9073-9080, 1992.*
Zhu et al. Journal of Biological Chemistry, vol. 288, No. 5, pp. 3545-3552, Feb. 1, 2013, published online Dec. 19, 2012.*
Ngo et al. in The Protein Folding Problem and Tertiary Structure Prediction, 1994, Merz et al. (ed.), Birkhauser, Boston, MA, pp. 433 and 492-495.*

* cited by examiner

*Primary Examiner* — Richard G Hutson
(74) *Attorney, Agent, or Firm* — Banner & Witcoff, Ltd.

(57) ABSTRACT

Cyanophage Syn5 RNA polymerase (RNAP) and methods of purifying it are provided. Cyanophage Syn5 RNAP having one or more promoter mutations are provided. Methods of expressing cyanophage Syn5 RNAP are provided. Novel promoter sequences and in vitro transcription systems utilizing Syn5 RNAP are provided. Methods of making high range ssRNA ladders are also provided. Methods of incorporating 2'-modified dNTPs using Syn5 RNA polymerase are provided.

17 Claims, 30 Drawing Sheets

Specification includes a Sequence Listing.

FIG. 1A     FIG. 1B
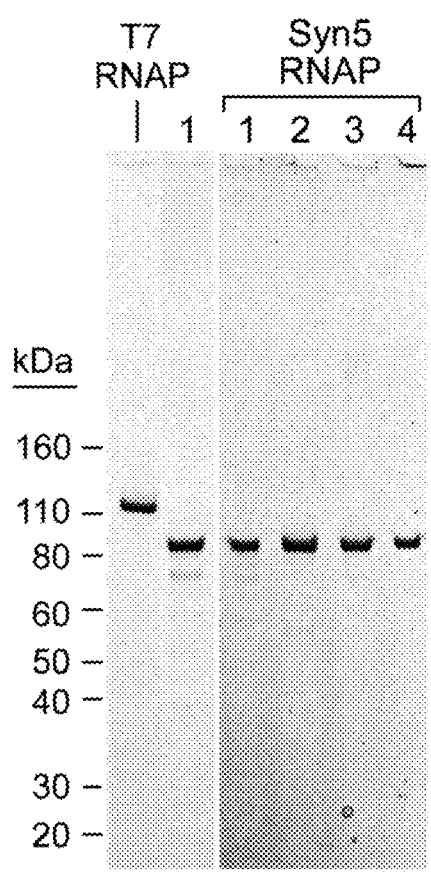
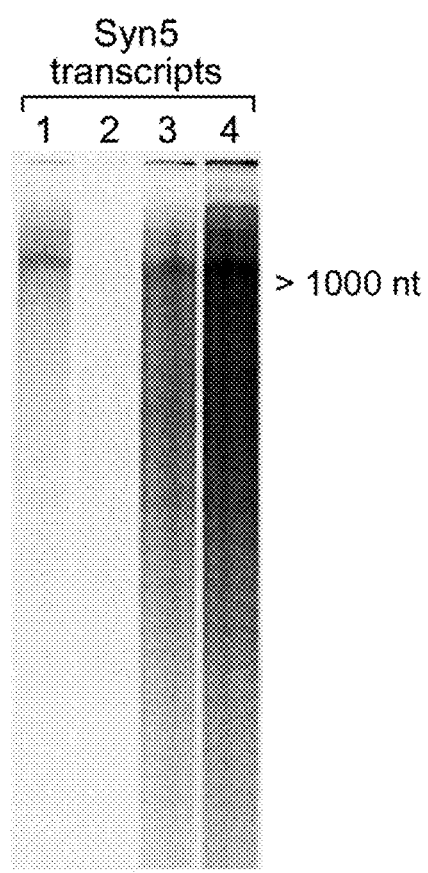

FIG. 2A
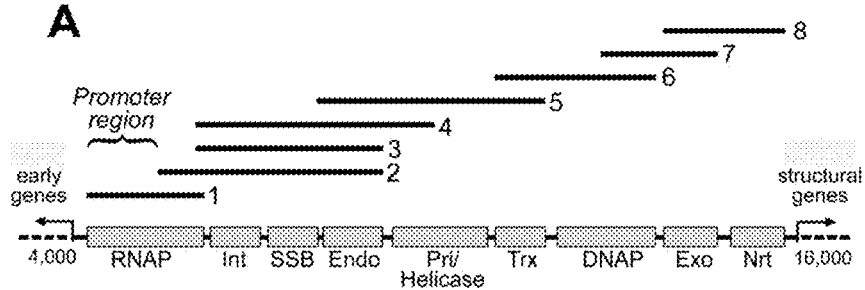
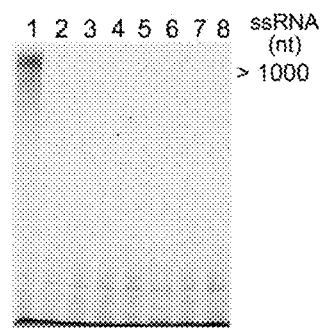
FIG. 2B
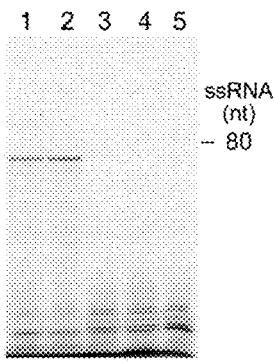
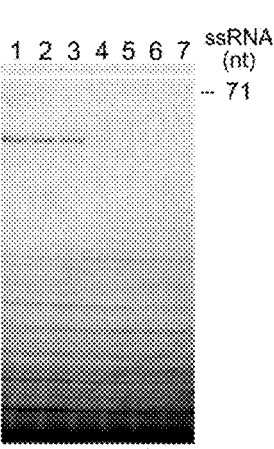
FIG. 2C

FIG. 3A
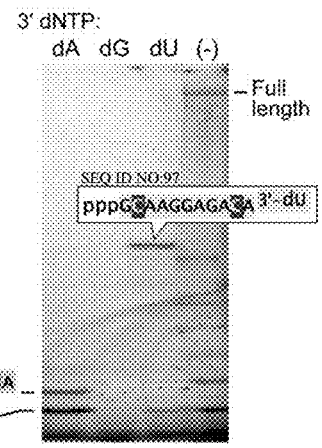
FIG. 3B
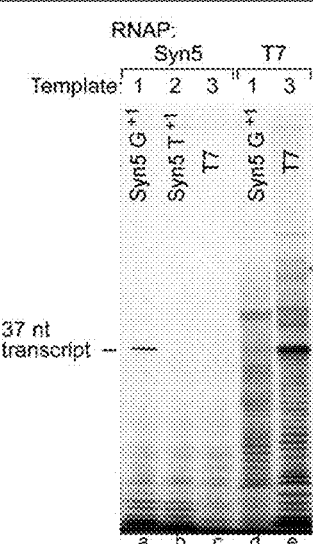
FIG. 3C
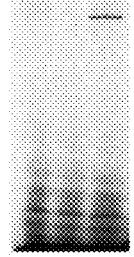
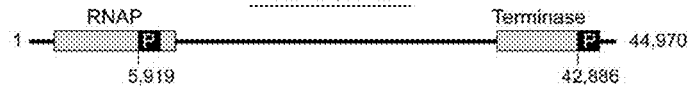

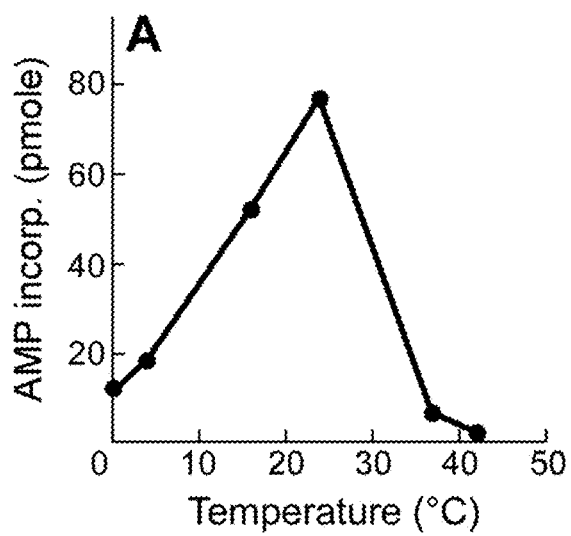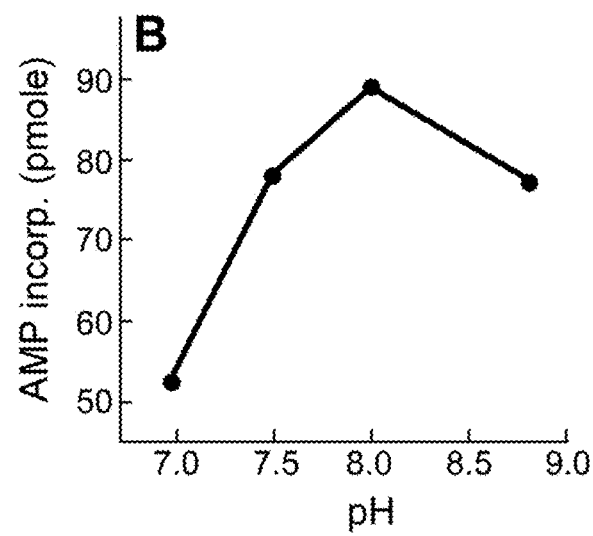
FIG. 4A  FIG. 4B

FIG. 5A
FIG. 5B
FIG. 5C
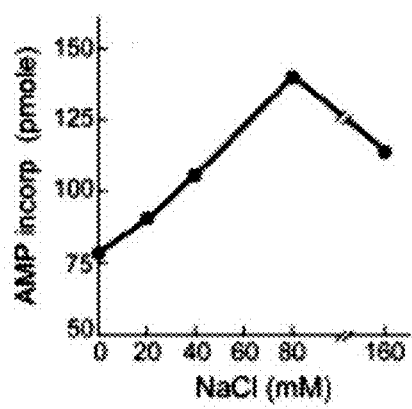
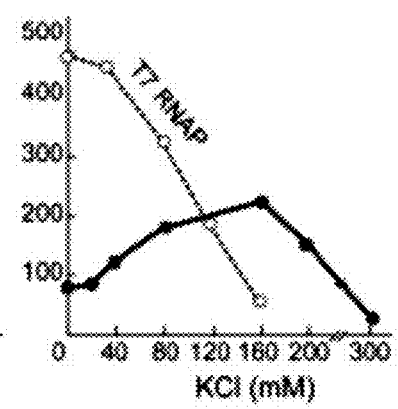
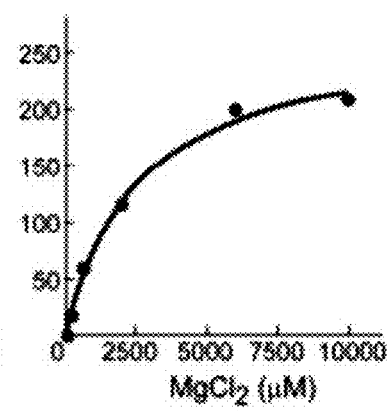

FIG. 7A
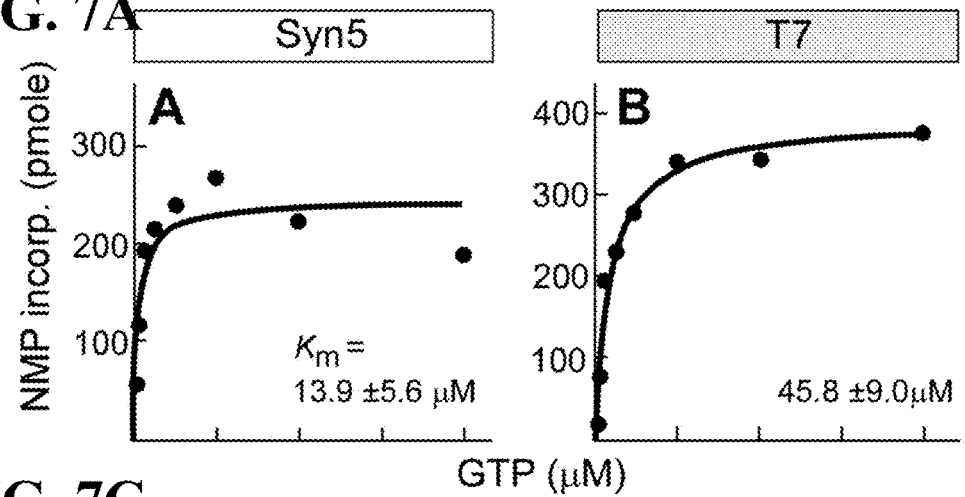
FIG. 7B
FIG. 7C
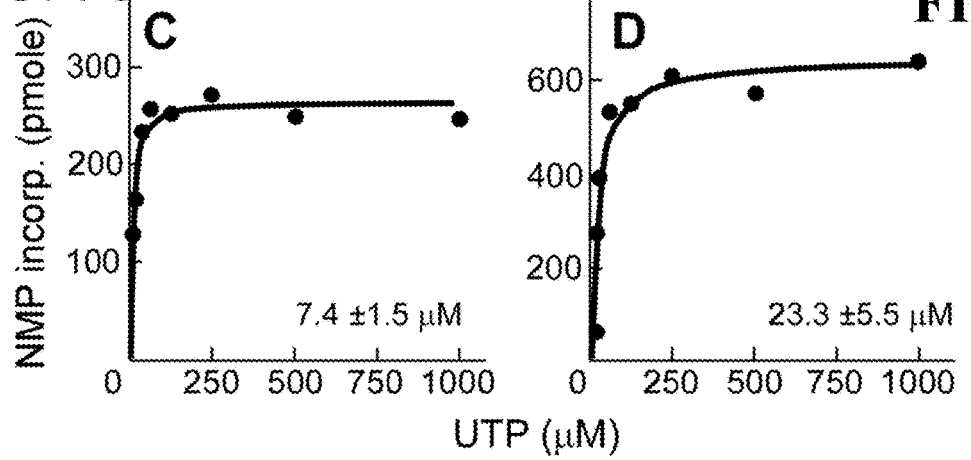
FIG. 7D

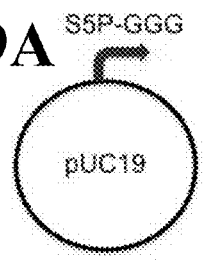
FIG. 9A
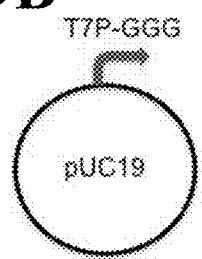
FIG. 9B
FIG. 9C
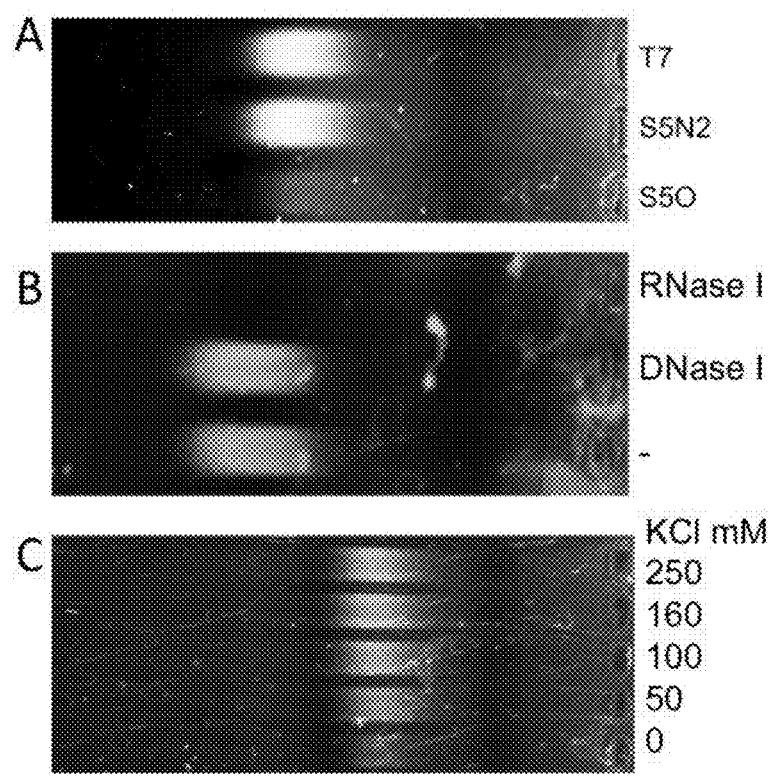
FIG. 9D
FIG. 9E
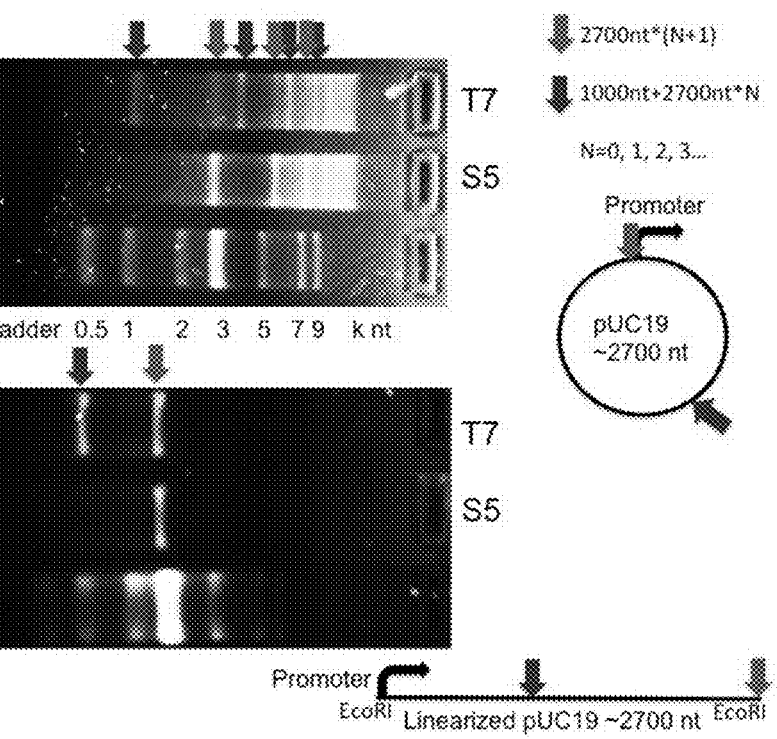

```
ATGTCCTTCGATCTCATCGCTCGCCAGCTTCAGCGTGAGACCGAGGCCGCGGAGCTGGCCCGCAAGCGTC
TACAAGACGCCCGACGCGAGGCCAATGAACGCTCCTATGCCTCAAGCAACATCGAGAGCCGCAAGGCCAT
CGCGACGTTCCTGGATCCCATCGCCCAACGCATCGGCGAACGCCTGTTCACGCTACGGCGTGGTACTGGT
GCAGTTGATGCCGCCGAGGTCTACAAGCATCTGAAGAACGCCGATCACCATCATCTGGCGCTCATCACGA
TGAAGACAGCCCTGGACGTCCTGGGCAAAGATCCCGAGCCACAGATCCAACAGCTGACCACAGCCATTGG
CCGCAACATCCAGCTGGAGCTCCGCCTCACGTACTACGCCGAGGAAAACCCGGAGCTCTACAAACAGGCC
TCCCGCTTCTTCCACGCAGGCACTGGCACCCGCCAGAAAGCCACGGTGATCAAACTCAAGTTCAACCGCG
AGGGCATTGAGTGGGACCAATGGTCCCGCGTCACCTGTCACAAGGTTGGCCAATGGCTCATGTTGGCTAT
GGCCGACGTCACCGGCTGGATTGAACGGGCAACCGACCGAACCAGTGGAGGACGCAAAACCAAGACCCGC
ATCTGCTACTCCCGCGAGTTCTTGCAGCATCGGGACACAATCCTCGCAGCAGCTGAGCAGTTGGCCTTCT
GCCAGTGGCCCATGCTTTGCCCTCCCATTGAGTGGTCCAACGACCACAACGGTGGGTACCTGAGCGAACA
GATCCGGCGGGTCAATCCGCTGATTCGTAAAACGGGTCCATTGGGCACCCGTAAGCAAGGAGACATACCC
CTTGCGATGCTCAACAACCTGCAGGGTCAGGCCTACAAGGTCAACCCTGAAGTTCTCGACATAGCGAACC
ACTGCTACGAGTCCAACGTGACCGTAGGCAAGTTCATACGCCACGCTCCCCTACCTGTTCCACCATCACC
CGGTGAGGACTGTACAGAGGACCAGCTCACAGCCTATAAACGGGCACGACGTGAGGCCGAGGACTTCAAC
GCACAGATCAGTCAGAAGAACTGGCGCACGACCGAGGTCATGTATGTGGCCCGCAAGTACGCCGACGAGG
CCTCCTTCTGGATGCCCGCCAGCTTCGACTATCGCGGCCGTGTTTACTTTCTGAACACTGCCCTCAACCC
GCAGGGGACTGACTTCGACAAGGCGCTCCTTTACTTCGCTGAGGAGGGTCCGGTCAACGAATGGTGGCTA
TCCTTCCACGTCGCGACCACCTACGGCCTCGACAAGGAGACCATGGTCAACCGGGTCCAATGGGCTCGGG
ACAACCACGAGCTCATCGATCGCATCGCCTCTGACCCCGTCCGCCATACCGAGTGGCACGACGCTGACGA
GCCCTGGTGCTTCCTGGCTGCCTGCCTCGAGTACAAGGCCTGCGTGATCGATGGCACCAAACAGACCAGC
GGCCTCCCTATCGGGATCGACGCCACCTGTTCAGGCCTGCAGCACCTCGCTGCTATGACCCGCTGCGGAC
GCACAGCCGCCCTGGTCAACGTGACACCGACCGACAAGCCGGCCGATGCTTACAAGACCGTGGCGCAAGC
ATCCCTCAAGCATCTCCCCAAGGAGCAGCACGAGTGGATCACCCGCAAGGTCACCAAAAGGCCCGTCATG
TGCACACCCTACGGGGTGACCATGTCATCGGCCCGCGGCTACATCCGCGATCAGCTGGTGAAGGACGGCC
ACAAGGAGGACCTCCGATCTCCTGGCGTGCTCAACGGCATCGTCAAGGCGATCTTTAATGAGGCCATCCC
TGAGGTCATCCCCGGCCCCGTGCAGGTCATGGCCTGGCTCAAGCGTTCAGCTGGTCAGATCATCGACCGG
GGTGATTCCACCATCACGTGGACCACGCCCTCAGGCTTCGAGGTTGTTCAAGACCTCAAAAAGTCCAAGA
CCTACGAGGTCAAGACCCGCATCATGGGCGGAGCACGGATCAAGCTCCAAGTGGGCGACGGGTTCACCGA
CGAGCCCGACCGTGACCACCACAAAAGCGCACTGGCTCCCAACGTGGTGCACAGCAACGATGCGTCTCTC
CTCCACCTGACCTTCGCCTTCTGGGACAAGCCCTTCACGGTCATCCATGACTGTGTCCTGGGCCGTTCCT
GCGACATGGATCAGATGGGCTCCGACATCCGGCTTCATTTCGCCGAGATGTACAAGGCCGACGTGATGCA
AGACTGGGCCGACCAGGTGGGCGTTGAGCTCCCTGTCGACCTGATCAAAAACACGCTCGACATCGACAGC
GTCAACCAGTCCCTTTACTTCTTCTCCTGA (SEQ ID NO:22)
```

FIG. 14

```
MSFDLIARQLQRETEAAELARKRLQDARREANERSYASSNIESRKAIATFLDPIAQRIGERLFTLRRGTG
AVDAAEVYKHLKNADHHHLALITMKTALDVLGKDPEPQIQQLTTAIGRNIQLELRLTYYAEENPELYKQA
SRFPHAGTGTRQKATVIKLKFNREGIEWDQWSRVTCHKVGQWLMLAMADVTGWIERATDRTSGGRKTKTR
ICYSREFLQHRDTILAAAEQLAFCQWPMLCPPIEWSNDHNGGYLSEQIRRVNPLIRKTGPLGTRKQGDIP
LAMLNNLQGQAYKVNPEVLDIANHCYESNVTVGKFIRHAPLPVPPSPGEDCTEDQLTAYKRARREAEDFN
AQISQKNWRTTEVMYVARKYADEASFWMPASFDYRGRVYFLNTALNPQGTDFDKALLYFAEEGPVNEWWL
SFHVATTYGLDKETMVNRVQWARDNHELIDRIASDPVRHTEWHDADEPWCFLAACLEYKACVIDGTKQTS
GLPIGIDATCSGLQHLAAMTRCGRTAALVNVTPTDKPADAYKTVAQASLKHLPKEQHEWITRKVTKRPVM
CTPYGVTMSSARGYIRDQLVKDGHKEDLRSPGVLNGIVKAIFNEAIPEVIPGPVQVMAWLKRSAGQIIDR
GDSTITWTTPSGFEVVQDLKKSKTYEVKTRIMGGARIKLQVGDGFTDEPDRDHHKSALAPNVVHSNDASL
LHLTFAFWDKPFTVIHDCVLGRSCDMDQMGSDIRLHFAEMYKADVMQDWADQVGVELPVDLIKNTLDIDS
VNQSLYFFS (SEQ ID NO:23)
```

FIG. 15

>Syn5 RNAP-NP
atgtccttcgatctcatcgctcgccagcttcagcgtgagaccgaggccgcggagctggcccgcaagcgtctacaagacgc
ccgacgcgaggccaatgaacgctcctatgcctcaagcaacatcgagagccgcaaggccatcgcgacgttcctggatccca
tcgcccaacgcatcggcgaacgcctgttcacgctacggcgtggtactggtgcagttgatgccgccgaggtctacaagcat
ctgaagaacgccgatcaccatcatctggcgctcatcacgatgaagacagccctggacgtcctgggcaaagatcccgagcc
acagatccaacagctgaccacagccattggccgcaacatccagctggagctccgcctcacgtactacgccgaggaaaacc
cggagctctacaaacaggcctcccgcttcttccacgcaggcactggcacccgccagaaagccacggtgatcaaactcaag
ttcaaccgcgagggcattgagtgggaccaatggtcccgcgtcacctgtcacaaggttggccaatggctcatgttggctat
ggccgacgtcaccggctggattgaacgggcaaccgaccgaaccagtggaggacgcaaaaccaagacccgcatctgctact
cccgcgagttcttgcagcatcgggacacaatcctcgcagcagctgagcagttggccttctgccagtggcccatgctttgc
cctcccattgagtggtccaacgaccacaacggtgggtacctgagcgaacagatccggcgggtcaatccgctgattcgtaa
aacgggtCCTCTTGGTACGCGCAAGcaaggagacatacccttgcgatgctcaacaacctgcagggtcaggc
ctacaagg
tcaaccctgaagttctcgacatagcgaaccactgctacgagtccaacgtgaccgtaggcaagttcatacgccacgctccc
ctacctgttccaccatcacccggtgaggactgtacagaggaccagctcacagcctataaacgggcacgacgtgaggccga
ggacttcaacgcacagatcagtcagaagaactggcgcacgaccgaggtcatgtatgtggcccgcaagtacgccgacgagg
cctccttctggatgcccgccagcttcgactatcgcggccgtgtttactttctgaacactgccctcaacccgcaggggact
gacttcgacaaggcgctcctttacttcgctgaggagggtccggtcaacgaatggtggctatccttccacgtcgcgaccac
ctacggcctcgacaaggagaccatggtcaaccgggtccaatgggctcgggacaaccacgagctcatcgatcgcatcgcct
ctgaccccgtccgccataccgagtggcacgacgctgacgagccctggtgcttcctggctgcctgcctcgagtacaaggcc
tgcgtgatcgatggcaccaaacagaccagcggcctccctatcgggatcgacgccacctgttcaggcctgcagcacctcgc
tgctatgacccgctgcggacgcacagccgccctggtcaacgtgacaccgaccgacaagccggccgatgcttacaagaccg
tggcgcaagcatccctcaagcatctccccaaggagcagcacgagtggatcacccgcaaggtcaccaaaaggcccgtcatg
tgcacaccctacggggtgaccatgtcatcggcccgcggctacatccgcgatcagctggtgaaggacggccacaaggagga
cctccgatctcctggcgtgctcaacggcatcgtcaaggcgatctttaatgaggccatccctgaggtcatccccggccccg
tgcaggtcatggcctggctcaagcgttcagctggtcagatcatcgaccggggtgattccaccatcacgtggaccacgccc
tcaggcttcgaggttgttcaagacctcaaaaagtccaagacctacgaggtcaagacccgcatcatgggcggagcacggat
caagctccaagtgggcgacgggttcaccgacgagcccgaccgtgaccaccacaaaagcgcactggctcccaacgtggtgc
acagcaacgatgcgtctctcctccacctgaccttcgccttctgggacaagcccttcacggtcatccatgactgtgtcctg
ggccgttcctgcgacatggatcagatgggctccgacatccggcttcatttcgccgagatgtacaaggccgacgtgatgca
agactgggccgaccaggtgggcgttgagctccctgtcgacctgatcaaaaacacgctcgacatcgacagcgtcaaccagt
ccctttacttcttctcctga (SEQ ID NO:83)

FIG. 22

RNA POLYMERASE, METHODS OF PURIFICATION AND METHODS OF USE

RELATED APPLICATION DATA

This application is a continuation of PCT application no. PCT/US2014/051506, designating the United States and filed Aug. 18, 2014; which claims the benefit U.S. Provisional Patent Application No. 61/866,657, filed on Aug. 16, 2013 and U.S. Provisional Application No. 61/952,192, filed on Mar. 13, 2014; each of which are hereby incorporated by reference in their entireties.

STATEMENT OF GOVERNMENT INTERESTS

This invention was made with government support under GM054937 awarded by the National Institutes of Health. The government has certain rights in the invention.

FIELD

The present invention relates in general to polymerases, their purification and use.

BACKGROUND

Bacteriophages are the most abundant and diverse biological entities on earth. Recently genome sequencing and bioinformatics studies have revealed marine phages to be the numerically largest and most diverse group of organisms in the ocean. Phages that infect the dominant cyanobacteria from the genera *Synechococcus* and *Prochlorococcus* are estimated at $10^{30}$ particles in the ocean (Suttle (2005)). 60-80% of their putative proteins have no sequence similarity to known proteins. Since a large portion of these proteins must play roles in nucleic acids metabolism, one would expect numerous novel mechanisms underlying the fundamental processes including transcription, DNA replication, and recombination. Phage enzymes have played critical roles in biochemical research and biotechnology as reagents for DNA/RNA processing. Biotechnology requires diverse and efficient molecular tools for nucleic acid manipulation and phage proteins are always good candidates due to their simplicity and high efficiency. However, biochemical characterization of phage proteins has been largely limited to phages identified during the onset of molecular biology when only a tiny portion of the huge phage group had been revealed. Consequently, the popular phage protein tools are mostly derived from very limited types of phages found in similar environments. Marine cyanophages are viruses that infect the dominant photoautotrophs—cyanobacteria. By killing 20% of marine biomass per day, cyanophages play a major role in the maintenance of the marine environment and in the cycling of marine energy (Suttle (2005), (2007)). Gene transfer between cyanophages and cyanobacteria represents the largest scale of genetic communication on Earth and is believed to have played a significant role in the evolution of the biosphere (Suttle (2005), (2007); Lindell et al. (2005), (2007)). Since 60 to 80% of the sequences in cyanophage genomes are not homologous to those in the existing database, cyanophages constitute a tremendous reservoir of unexplored genetic diversity (Suttle (2005)). Recent advances in genome sequencing and bioinformatics have greatly improved our understanding of cyanophages (Chen et al. (2002); Liu et al. (2008); Mann et al.; Liu et al. (2007); Millard et al.; Sullivan et al. (2005); Sullivan et al. (2009); Weigele et al.; Pope et al; Lindell et al.; Sharon et al.; Sabehi et al.), and studies of their gene products have provided intriguing insights into their physiology (Lindell et al. (2005), (2007); Raytcheva et al.; Gao et al.; Thompson et al.). However, there has been little characterization of the proteins involved in nucleic acid metabolism, one of the most critical aspects in the life cycle of cyanophage.

Syn5 is a cyanophage with a short tail isolated from the Sargasso Sea; it is homologous to bacteriophage T7 that infects *Escherichia coli* (Waterbury et al.). The laboratory host, cyanobacterial strain *Synechococcus* sp. WH8109 (Waterbury et al.; Sullivan et al.), belongs to marine cluster A of *Synechococcus*, Glade II, one of the most widely distributed clades in the oceans (Zwirglmaier et al.). The genome of Syn5 has 46,214 bp containing 61 predicted open reading frames (Pope et al.). The gene organization is typical of dsDNA phages with its DNA replication genes clustered in the left region of the genome and the genes encoding its structural proteins in the right region. The gene order shares strong similarity with bacteriophage T7 as well as several other cyanophages, notably *Synechococcus* phage P60 and *Prochlorococcus* phage P-SSP7. Id.

DNA-dependent RNA polymerases are responsible for transcription, the synthesis of messenger RNAs, from a double-stranded DNA template. A homologous family of single-subunit RNAP transcribes most T7-like bacteriophage genes. These single-subunit enzymes share many of the biochemical characteristics of the larger multienzyme RNAP of their hosts; their relative simplicity has made them attractive for biochemical and structural analysis (Cheetham et al.). One of the most extensively studied RNAP is that encoded by bacteriophage T7 (Cheetham et al.; Davanloo et al.). T7 RNAP and its promoters are widely used for overexpression of recombinant genes, and in vitro transcription by T7 RNA polymerase is useful in many molecular biology studies.

RNA plays fundamental roles in cell physiology and is an important target for biomedical research and biotechnology. RNA transcripts synthesized by RNA polymerase in vitro are used widely in applications that include hybridization analysis, NMR and crystallographic structural studies, biochemical and genetic studies, and the preparation of functional molecules such as tRNA, mRNA, sRNA, ribozymes, and aptamers.

The RNA polymerase encoded by bacteriophage T7 is widely used to synthesize RNA molecules (Chamberlin et al. (1982); Davanloo et al; Tabor et al.; Milligan et al. (1987); Milligan et al. (1989)). These reactions use DNA that contains a T7 RNA polymerase promoter to initiate synthesis. RNA synthesis proceeds to the end of the DNA, resulting in a "run-off synthesis" product. The other two enzymes available for run-off RNA synthesis are bacteriophage T3 and SP6 RNA polymerase (Chamberlin et al.; Melton et al.; Krieg et al.; Morris et al.), which have properties similar to those of T7 RNA polymerase. Problems encountered with these RNA polymerases include limited processivity, high salt sensitivity (Chamberlin et al. (1973)), undesired products resulting from abortive synthesis (Lyakhov et al.), and most significantly, the addition of a non-base-paired nucleotide at the 3'-end of the run-off transcript. This latter product is designated N+1 product (Krupp et al.). The N+1 product is usually 50%-200% of the desired RNA transcript depending on the reaction conditions (Moran et al.; Kao et al.). Extensive efforts have been made to improving the 3' homogeneity of T7 transcripts including modification of the DNA templates (Id.) and the attachment of ribozymes to the 3'-end of the desired RNAs (Schürer et al; Wichlacz et al;

Salvail-Lacoste et al.). These methods are partially effective but increase the cost and the complexity of the process. Consequently, an RNA polymerase reaction that would yield precise and homogeneous run-off products would offer a significant advantage over existing reagents methods.

SUMMARY

The RNA polymerase (RNAP) of Syn5 is homologous to T7 RNAP based on DNA sequence, although it is somewhat smaller in size. Characterization of the Syn5 RNAP is particularly interesting since its host, cyanobacteria *Synechococcus*, is one of the most ancient bacteria and therefore may have primitive features that provide insight into the evolution of transcription systems. An important first step in understanding the transcription of the Syn5 genome is the establishment of a transcription system using purified proteins from Syn5. Furthermore, the Syn5 RNAP should possess properties that distinguish it from T7 RNAP since it is adapted to the ocean environment.

A single subunit DNA-dependent RNAP was identified and purified to apparent homogeneity from cyanophage Syn5 that infects the marine cyanobacteria *Synechococcus*. Syn5 is homologous to bacteriophage T7 that infects *E. coli*. Using the purified enzyme its promoter has been identified by examining transcription of segments of Syn5 DNA and sequencing the 5'-termini of the transcripts. Only two Syn5 RNAP promoters, having the sequence 5'-ATTGGGCACCCGTAA-3' (SEQ ID NO:1), are found within the Syn5 genome. One promoter is located within the Syn5 RNAP gene and the other is located close to the right genetic end of the genome. The purified enzyme and its promoter have enabled a determination of the requirements for transcription. Unlike the salt-sensitive bacteriophage T7 RNAP, this marine RNAP requires 160 mM potassium for maximal activity. The optimal temperature for Syn5 RNAP is 24° C., much lower than that for T7 RNAP. Magnesium is required as a co-factor although some activity is observed with ferrous ions. Syn5 RNAP is more efficient in utilizing low concentrations of ribonucleotides than T7 RNAP.

The enzyme predominantly used for in vitro run-off RNA synthesis is bacteriophage T7 RNAP. T7 RNAP synthesizes, in addition to run-off products of precise length, a 3' N+1 product. This contaminating product is extremely difficult to remove. The single subunit RNAP from marine cyanophage Syn5 with the identified promoter sequence catalyzes RNA synthesis over a wider range of temperature and salinity than does T7 RNAP. Its processivity is greater than 30,000 nt without the appearance of intermediate products. Most significantly, Syn5 RNAP produces precise run-off transcripts with homogeneity in their 3' termini. This latter property makes it advantageous for production of RNAs that require precise 3'-termini such as tRNAs and RNA fragments for subsequent assembly.

Using homogeneous recombinant protein, an in vitro Syn5 transcription system was developed and the properties of the enzyme and its products were investigated, as described further herein. According to the present disclosure, Syn5 RNAP has several advantages over T7 RNAP in synthesizing RNA from linear DNA templates. These advantages include the recognition of a relatively short promoter sequence, a high tolerance to salt, and high processivity. However, the most significant advantage of the Syn5 enzyme is the much higher homogeneity of the 3'-terminus of its RNA products. RNA synthesis catalyzed by Syn5 RNAP results in precise run-off with the products lacking non-based additional nucleotides. The N+1 product synthesized by T7 RNAP cannot be removed by routine gel extraction and this impedes the function of these RNAs in applications where the precise 3'-terminus of the RNA is critical. These applications include the synthesis of tRNA molecules, RNA probes, RNA primers, genomes of some RNA viruses, RNAs for ligation and assembly, and specific RNAs for structure studies. Accordingly, embodiments of the present disclosure include the use of Syn5 RNAP in methods of making RNA having a precise 3'-terminus.

Accordingly, in certain exemplary embodiments, a method of performing in vitro transcription is provided. The method includes the steps of providing a cDNA encoding a cyanophage Syn5 RNA polymerase (RNAP) promoter sequence and a nucleic acid template sequence, a cyanophage Syn5 RNAP, and nucleotides, and incubating the nucleic acid template sequence, the cyanophage Syn5 RNAP and nucleotides together for a sufficient time to produce transcripts.

In certain aspects, the transcripts are selected from the group consisting of one or any combination of mRNA, tRNA, rRNA, miRNA, siRNA, snRNA, snoRNA, ribozymes, aptamers and RNA fragments. In other aspects, the incubating step is performed in the presence of a salt, e.g., KCl and/or NaCl, at a concentration of at least about 100 mM, at a concentration of at least about 160 mM, at a concentration of at least about 200 mM or at a concentration of about 250 mM. In still other aspects, the incubating step is performed at between about 4° C. and about 37° C., between about 10° C. and about 25° C., between about 14° C. and about 22° C., or at about 16° C. In certain aspects, the nucleotides are modified nucleotides. In other aspects, the purified cyanophage Syn5 RNAP includes a heterologous polypeptide sequence, e.g., a protein tag, selected from the group consisting of one or any combination of Avi tag, calmodulin tag, FLAG tag, HA tag, His tag, Myc tag, S tag, SBP tag, Softag 1, Softag 3, V5 tag, Xpress tag, Isopeptag, SpyTag, biotin carboxyl carrier protein tag, glutathione-s-tranferase tag, green fluorescent protein tag, maltose binding protein tag, Nus tag, streptavidin tag, streptactin tag, and thioredoxin tag. In certain aspects, the protein tag is removable from the purified cyanophage Syn5 RNAP. In other aspects, the transcripts are longer than about 10,000 nucleotides, longer than about 20,000 nucleotides, or longer than about 30,000 nucleotides. In some aspects, the nucleic acid template sequence comprises one or more T7 terminator-like sequences and full-length transcripts are synthesized. In other aspects, transcription is performed under stringent conditions, e.g., in the presence of less than about 2 mM $Mg^{2+}$ and/or in the presence of less than about 200 □M nucleotides. In other aspects, transcription is performed in the presence of one or both of $Mn^{2+}$ and $Fe^{2+}$.

In yet other aspects, greater than about 90% of the transcripts contain homogeneous 3' ends, greater than about 95% of the transcripts contain homogeneous 3' ends, or greater than about 99% of the transcripts contain homogeneous 3' ends. In other aspects, greater than about 90% of the transcripts contain precisely terminated 3' ends, greater than about 95% of the transcripts contain precisely terminated 3' ends, or greater than about 99% of the transcripts contain precisely terminated 3' ends. In still other aspects, greater than about 90% of the transcripts lack a nucleotide overhang at the 3' ends, greater than about 95% of the transcripts lack a nucleotide overhang at the 3' ends, or greater than about 99% of the transcripts lack a nucleotide overhang at the 3' ends. In other aspects, less than 20% of the transcripts contain a nucleotide overhang at their 3' ends, less than 10% of the transcripts contain a nucleotide overhang at their 3' ends, less than 5% of the transcripts contain a nucleotide overhang at their 3' ends or less than 1% of the transcripts contain a nucleotide overhang at their 3' ends. The method of claim 1, wherein less than 20% of the transcripts contain a nucleotide overhang at their 3' ends. In yet other aspects, less than 10% of the transcripts contain a nucleotide overhang at their 3' ends, less than 5% of the transcripts contain a nucleotide overhang at their 3' ends, or less than 1% of the transcripts contain a nucleotide overhang at their 3' ends.

In certain exemplary embodiments, a method of performing in vitro transcription is provided comprising the steps of providing a nucleic acid sequence encoding a cyanophage Syn5 RNAP promoter sequence and a nucleic acid template sequence, a cyanophage Syn5 RNAP having a protein tag, and nucleotides, and incubating the nucleic acid template sequence, the cyanophage Syn5 RNAP and nucleotides together for a sufficient time to produce transcripts.

In certain aspects, the transcripts are selected from the group consisting of one or any combination of mRNA, tRNA, rRNA, miRNA, siRNA, snRNA, snoRNA, ribozymes, aptamers and RNA fragments. In other aspects, the incubating step is performed in the presence of a salt, e.g., KCl and/or NaCl, at a concentration of at least about 100 mM, at a concentration of at least about 160 mM, at a concentration of at least about 200 mM or at a concentration of about 250 mM. In still other aspects, the incubating step is performed at between about 4° C. and about 37° C., between about 10° C. and about 25° C., between about 14° C. and about 22° C., or at about 16° C. In certain aspects, the nucleotides are modified nucleotides. In other aspects, the purified cyanophage Syn5 RNAP includes a heterologous polypeptide sequence, e.g., a protein tag, selected from the group consisting of one or any combination of Avi tag, calmodulin tag, FLAG tag, HA tag, His tag, Myc tag, S tag, SBP tag, Softag 1, Softag 3, V5 tag, Xpress tag, Isopeptag, SpyTag, biotin carboxyl carrier protein tag, glutathione-s-tranferase tag, green fluorescent protein tag, maltose binding protein tag, Nus tag, streptavidin tag, streptactin tag, and thioredoxin tag. In certain aspects, the protein tag is removable from the purified cyanophage Syn5 RNAP. In other aspects, the transcripts are longer than about 10,000 nucleotides, longer than about 20,000 nucleotides, or longer than about 30,000 nucleotides. In some aspects, the nucleic acid template sequence comprises one or more T7 terminator-like sequences and full-length transcripts are synthesized. In other aspects, transcription is performed under stringent conditions, e.g., in the presence of less than about 2 mM $Mg^{2+}$ and/or in the presence of less than about 200 □M nucleotides. In other aspects, transcription is performed in the presence of one or both of $Mn^{2+}$ and $Fe^{2+}$.

In yet other aspects, greater than about 90% of the transcripts contain homogeneous 3' ends, greater than about 95% of the transcripts contain homogeneous 3' ends, or greater than about 99% of the transcripts contain homogeneous 3' ends. In other aspects, greater than about 90% of the transcripts contain precisely terminated 3' ends, greater than about 95% of the transcripts contain precisely terminated 3' ends, or greater than about 99% of the transcripts contain precisely terminated 3' ends. In still other aspects, greater than about 90% of the transcripts lack a nucleotide overhang at the 3' ends, greater than about 95% of the transcripts lack a nucleotide overhang at the 3' ends, or greater than about 99% of the transcripts lack a nucleotide overhang at the 3' ends. In other aspects, less than 20% of the transcripts contain a nucleotide overhang at their 3' ends, less than 10% of the transcripts contain a nucleotide overhang at their 3' ends, less than 5% of the transcripts contain a nucleotide overhang at their 3' ends or less than 1% of the transcripts contain a nucleotide overhang at their 3' ends. The method of claim 1, wherein less than 20% of the transcripts contain a nucleotide overhang at their 3' ends. In yet other aspects, less than 10% of the transcripts contain a nucleotide overhang at their 3' ends, less than 5% of the transcripts contain a nucleotide overhang at their 3' ends, or less than 1% of the transcripts contain a nucleotide overhang at their 3' ends.

In certain exemplary embodiments, a kit for in vitro transcription is provided. The kit includes a cDNA plasmid comprising one or more promoter sequences, each promoter sequence having the nucleic acid sequence set forth as SEQ ID NO:1, wherein the one or more promoter sequences provide transcriptional control of an operably linked polynucleotide sequence, a cyanophage Syn5 RNAP (such as an isolated Syn5 RNAP or a purified Syn5 RNAP, or a synthetic Syn5 RNAP), optional nucleotides, and instructions for use. In certain aspects, the cyanophage Syn5 RNAP includes a protein tag. In other aspects, the operably linked polynucleotide sequence comprises one or more restriction sites.

In certain exemplary embodiments, a kit for in vitro transcription is provided. The kit includes a cDNA plasmid comprising one or more promoter sequences, each promoter sequence having the nucleic acid sequence set forth as SEQ ID NO:1, wherein the one or more promoter sequences provide transcriptional control of an operably linked polynucleotide sequence, a cyanophage Syn5 RNAP having a protein tag (such as an isolated Syn5 RNAP or a purified Syn5 RNAP, or a synthetic Syn5 RNAP), optional nucleotides, and instructions for use. In certain aspects, the plasmid is cDNA. In other aspects, the operably linked polynucleotide sequence comprises one or more restriction sites.

In certain exemplary embodiments, a kit for expressing cyanophage Syn5 RNAP is provided. The kit includes a cDNA encoding cyanophage Syn5 RNAP, and optional instructions for use. In certain aspects, the cDNA encoding the cyanophage Syn5 RNAP further comprises a nucleic acid sequence encoding a protein tag.

In certain exemplary embodiments, a cDNA encoding a cyanophage Syn5 RNAP having a protein tag, wherein the cDNA has least about 95% sequence identity to the nucleic acid sequence set forth as SEQ ID NO:22, is provided. In certain aspects, the protein tag is a His tag.

In certain exemplary embodiments, a cyanophage Syn5 RNAP having a protein tag, wherein the cyanophage Syn5 RNAP has least about 95% sequence identity to the amino acid sequence set forth as SEQ ID NO:23, is provided. In certain aspects, the protein tag is a His tag.

In certain exemplary embodiments, a method of purifying Syn5 RNAP is provided. The method includes the steps of expressing a Syn5 RNA polymerase comprising a heterologous protein tag, and purifying the Syn5 RNAP by contacting a chromatography column with the Syn5 RNAP in the presence of between about 1.5 M and 2.5 M salt, e.g., NaCl.

In certain exemplary embodiments, a plasmid is provided. The plasmid includes one or more promoter sequences, wherein each promoter sequence has the nucleic acid sequence set forth as SEQ ID NO:1, and wherein the one or more promoter sequences provide transcriptional control of an operably linked polynucleotide sequence.

In certain exemplary embodiments, a method of synthesizing a single-stranded RNA (ssRNA) ladder is provided. The method includes the steps of providing a circular template comprising a nucleic acid sequence including one or more promoters or terminators specific for an RNAP (e.g., Syn5 RNAP, T7 RNAP, T3 RNAP, SP6 RNAP or the like), providing RNA polymerase proteins specific for the one or more promoters or terminators, allowing transcription of the circular template under conditions that allow multiple RNA polymerase proteins to be present at or near the one or more promoters or terminators temporally, and allowing transcription of the template to generate an ssRNA ladder, wherein the largest nucleic acid sequence of the ladder is greater in size than the size of circular template.

In certain aspects, the largest nucleic acid sequence of the ssRNA ladder is greater than two, three, four, five, six, seven, eight, nine or ten times the size of the circular template. In other aspects, the largest nucleic acid sequence of the ssRNA ladder is greater than 1,000, 2,000, 3,000, 4,000, 5,000, 6,000, 7,000, 8,000, 9,000, 10,000, 15,000, 20,000, 25,000, 30,000, 35,000, 40,000, 45,000, 50,000, 55,000, 60,000, 65,000, 70,000, 75,000, 80,000, 85,000, 90,000, 95,000, 100,000 or more nucleotides in length. In still other aspects, the RNAP is provided in an amount causing an RNAP to stall at the one or more promoters or terminators. In yet other aspects, the circular template is about 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900 or about 4000 nucleotides in size.

In certain exemplary embodiments, a method of expressing a cyanophage Syn5 RNAP in a host cell is provided. The method includes the steps of providing a nucleic acid sequence comprising a cyanophage Syn5 RNAP cDNA having a mutation in its promoter region that inhibits cyanophage Syn5 RNAP protein from transcribing the cyanophage Syn5 RNAP cDNA sequence, transforming a host cell with the nucleic acid sequence, and allowing the host cell to express the Syn5 RNAP. In certain aspects, the mutation is silent with respect to the Syn5 RNAP protein sequence. In other aspects, the promoter region has about 90% identity or greater to the nucleic acid sequence set forth as SEQ ID NO:80.

In certain exemplary embodiments, a polynucleotide comprising a cyanophage Syn5 RNAP cDNA having a mutation in its promoter region that inhibits cyanophage Syn5 RNAP protein from transcribing the cyanophage Syn5 RNAP cDNA sequence is provided. In certain aspects, the mutation is silent with respect to the Syn5 RNAP protein sequence. In other aspects, the promoter region has about 90% identity or greater to the nucleic acid sequence set forth as SEQ ID NO:80. In still other aspects, the polynucleotide is a plasmid.

In certain exemplary embodiments, kit for in vitro transcription is provided. The kit includes a plasmid comprising one or more promoter sequences, each promoter sequence having about 90% identity or greater to the nucleic acid sequence set forth as SEQ ID NO:1, wherein the one or more promoter sequences provide transcriptional control of an operably linked polynucleotide sequence, a plasmid expressing a cyanophage Syn5 RNAP having a mutated promoter region, and optional instructions for use. In certain aspects, the mutated promoter region of the plasmid has about 90% identity or greater to the nucleic acid sequence set forth as SEQ ID NO:80.

In certain exemplary embodiments, a polynucleotide having about 80%, 85%, 90%, 95%, 96%, 97%, 98% or 99% identity or greater to the nucleic acid sequence set forth as SEQ ID NO:83 is provided.

In certain exemplary embodiments, a method of expressing a polynucleotide sequence is provided. The method includes the steps of providing a cDNA encoding the polynucleotide sequence and a cyanophage Syn5 promoter sequence, contacting the template sequence with cyanophage Syn5 RNAP, and allowing the cyanophage Syn5 RNAP to bind the cyanophage Syn5 RNAP promoter sequence and produce a transcript of the polynucleotide sequence. In certain aspects, the method utilizes an in vivo expression system or an in vitro expression system.

In certain exemplary embodiments, a method of expressing a polynucleotide sequence is provided. The method includes the steps of providing a template sequence encoding the polynucleotide sequence and a cyanophage Syn5 promoter sequence, contacting the template sequence with cyanophage Syn5 RNAP having a protein tag, and allowing the cyanophage Syn5 RNAP to bind the cyanophage Syn5 RNAP promoter sequence and produce a transcript of the polynucleotide sequence. In certain aspects, the method utilizes an in vivo expression system or an in vitro expression system.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present invention will be more fully understood from the following detailed description of illustrative embodiments taken in conjunction with the accompanying drawings in which:

FIGS. 1A-1B depict purified Syn5 RNAP and transcription on Syn5 DNA. A) SDS-PAGE gel of purified non-tagged Syn5 RNAP (lane 1) and N-terminal His-tagged Syn5 RNAP obtained after a Ni-NTA agarose column (lane 2), gel filtration column (lane 3), and cellulose phosphate column (lane 4). Purified T7 RNAP is shown for comparison. Proteins were stained with Coomassie Blue. B) A 10% denaturing TBE-Urea gel of radioactive labeled transcription products generated by Syn5 RNAPs on Syn5 genomic DNA. The lanes in B correspond to transcription by the proteins purified in A).

FIGS. 2A-2C depict identification of the Syn5 promoter. A) The entire 12 kb DNA metabolism region (beginning of the RNAP gene to the end of ribonucleotide reductase gene) of the Syn5 genome is shown in the schematic. Overlapping PCR fragments covering this region were examined for the presence of an active promoter for transcription by the purified Syn5 RNAP. Only the fragment containing the RNAP gene (template 1) was active for transcription. The following putative proteins derived from bioinformatics prediction (13) are shown: Int, integrase; SSB, ssDNA-binding protein; Endo, endonuclease; Pri/Helicase, primase/helicase; Trx, thioredoxin; DNAP, DNA polymerase; Exo, exonuclease and Nrt for ribonucleotide reductase. B) Narrowing the location of the Syn5 promoter using DNA templates with truncated 5'-ends. Based on the results obtained with templates 2 and 3 the promoter starts in the region highlighted in black background in template 2. C) Determination of the 5'-end of Syn5 promoter using DNA templates with truncated 5'-ends. A series of templates each with one more nucleotide removed from the 5'-terminus were screened as effective transcription templates for Syn5 RNAP. Based on the results obtained with templates 3 and 4 the promoter starts from the A highlighted in black background in template 3.

FIGS. 3A-3C depict characterization of the Syn5 promoter. A) Determination of the 3'-end of Syn5 promoter. 3'-dATP, 3'-dGTP, 3'-dUTP replaced ATP, GTP and UTP, respectively, as chain terminator to sequence the 5'-end of Syn5 RNAP transcript on a template same as template 1 in FIG. 2B. Once the 5'-terminus of the transcript was determined, the sequence preceding it should be the promoter and the 3'-end of the promoter can thus be defined. A 25% TBE-urea gel was used for this assay. B) Cross recognition between Syn5 and T7 transcription systems. Syn5 RNAP synthesizes runoff products on a fragment of T7 DNA provided the T7 promoter is replaced by a Syn5 promoter (lane a). Syn5 RNAP fails to produce transcripts if the first nucleotide downstream of the promoter is changed from G to T (lane b). Syn5 and T7 RNAP do not recognize the heterologous promoter (lane c and d). T7 RNAP produces runoff and "N+1" products upon its own promoter (lane e). Sequences of templates can be found in Table 1. C) Schematic showing the identity of the two promoters based on the above data and previous bioinformatics analysis on the Syn5 and P-SSP7 genomes, respectively. Syn5 RNAP transcribes DNA fragments containing a Syn5 promoter to produce transcripts (>1500 for template 1, lane 1; and >200 nt for template 3, lane 3). Syn5 RNAP does not transcribe the DNA fragment covering the region between the DNA metabolism and structural genes in the middle of Syn5 genome (lane 2).

FIGS. 4A-4B depict the effect of temperature and pH on Syn5 RNAP activity. A) Temperature. B) pH. RNA polymerase activity was measured as described in Materials and Methods described herein. The reactions contained 6 mM $MgCl_2$, 200 □M 4 rNTPs ($^3$H-ATP), 50 nM Syn5 RNAP and 4 nM template (pET24-S5RNAP). The pH was 8.0 for assays in A and the temperature was 24° C. for B. Reactions were terminated and the amount of AMP incorporated was measured at 3, 10, and 30 min. The AMP incorporation was linear in this time range and the data measured at 10 min are presented.

FIGS. 5A-5C depict reaction requirements for Syn5 RNAP. A) Effect of NaCl on Syn5 RNAP activity. B) Effect of KCl on Syn5 and T7 RNAP (dashed line) activity. C) $MgCl_2$ concentration on Syn5 RNAP activity. Reactions contained 200 □M 4 rNTPs ($^3$H-ATP), 50 nM Syn5 RNAP and 4 nM template (pET24-S5RNAP). For A and B, reactions also contained 6 mM $MgCl_2$. For C, 160 mM KCl was present. Reactions were terminated and the amount of AMP incorporated was measured at 2.5, 5, and 10 min. AMP incorporation was linear in this time range and the data measured at 10 min are presented.

FIGS. 7A-7D depict a comparison of transcription efficiency of Syn5 and T7 RNAP at various ribonucleotide concentrations. A) Incorporation of NMP by Syn5 RNAP at various GTP concentrations. B) Incorporation of NMP by T7 RNAP at various GTP concentrations. C) Incorporation of NMP by Syn5 RNAP at various UTP concentrations. D) Incorporation of NMP by T7 RNAP at various UTP concentrations. Varied ribonucleotide concentrations were 7.8, 15.6, 31.3, 62.5, 125, 250, 500, 1000 □M while other NTPs were all at 1 mM, RNAP and template were both 20 nM, and the reaction time was 5 min at 24° C. 160 mM KCl was added for Syn5 RNAP reactions.

FIGS. 9A-9H depict the processivity of Syn5 and T7 RNA polymerases. A) Agarose gel showing RNA synthesis by previously purified Syn5 RNA polymerase, newly purified Syn5 RNA polymerase with the improved procedure, and T7 RNA polymerase on a plasmid template containing a single cognate promoter (as shown in the schematic). B) Product as shown in A) by S5N2 RNA polymerase was incubated with 1 U/□l RNase I or DNase I to confirm its RNA nature. C) Effect of increasing KCl concentration on Syn5 RNA polymerase transcription. D) Products by Syn5 and T7 RNAP in a rolling-circle manner were analyzed at denaturing condition. E) Same assay as D) except that the template plasmids were linearized as shown in the schematic. F) & G) Decreasing the concentration of T7 (F) and Syn5 (G) RNA polymerase reduced the abortive products due to clash of RNA polymerases at promoter region. H) RNA polymerase promoter distribution on coliphage T7 and cyanophage Syn5 genomes.

FIG. 14 depicts a cDNA sequence encoding a cyanophage Syn5 RNAP, set forth as SEQ ID NO:22.

FIG. 15 depicts an amino acid sequence of a cyanophage Syn5 RNAP, set forth as SEQ ID NO:23.

FIG. 22 depicts a cDNA sequence encoding Syn5 RNAP-NP, set forth as SEQ ID N0:83. Mutated nucleotides are depicted in bold.

DETAILED DESCRIPTION OF CERTAIN EMBODIMENTS

Figure 6:
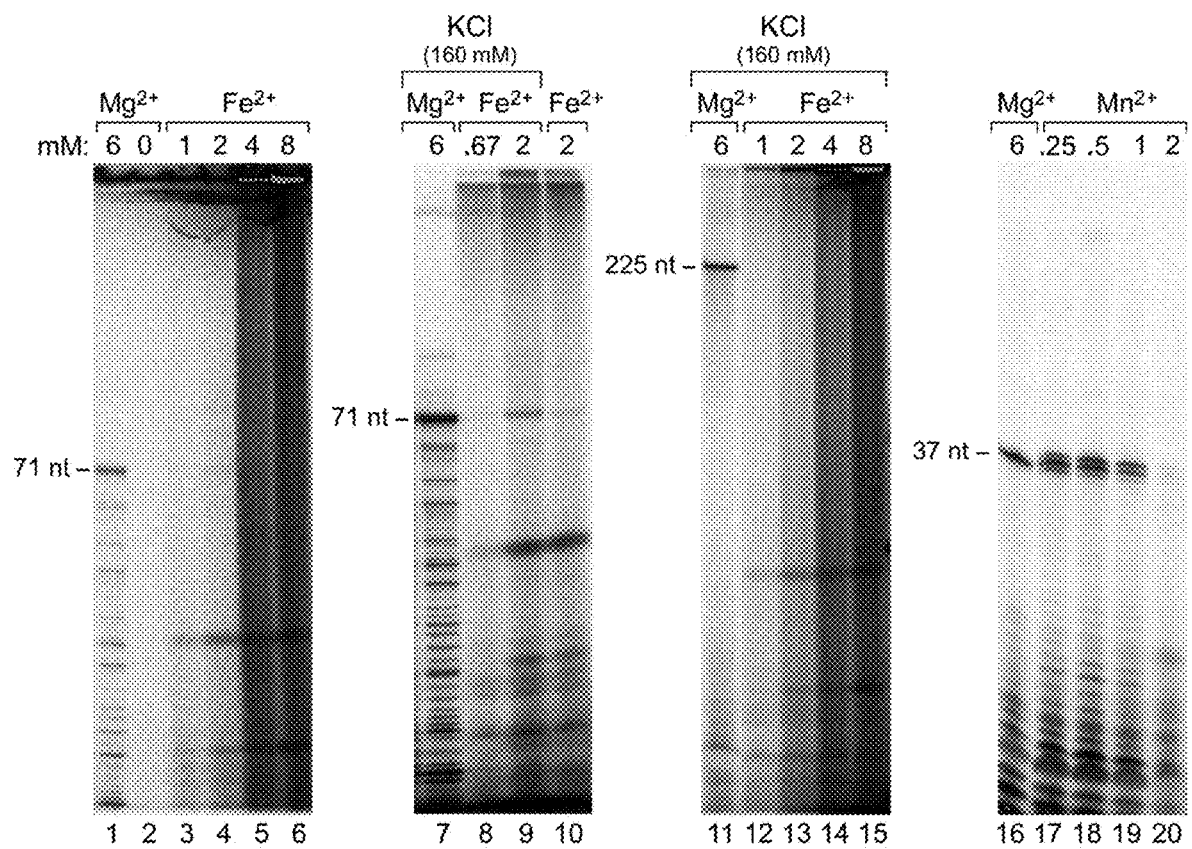
FIG. 6 depicts a comparison of Syn5 RNAP transcription products in the presence of $MgCl_2$, $FeCl_2$ or $MnCl_2$ on denaturing gels. Reactions contained 200 □M ATP, GTP, UTP and 10 □M□□□-$^{32}$P]CTP, 50 nM Syn5 RNAP, DNA templates (1 □M template as shown in FIG. 3A for 71 nt runoff transcript, 4 nM template 3 as shown in FIG. 3C for 225 nt product, or 1 □M template 1 as shown in FIG. 3B for 37 nt runoff transcript). Amounts of $MgCl_2$, $FeCl_2$, $MnCl_2$ and KCl in the reactions are shown in the figure.

The subject application is directed in part to purified cyanophage Syn5 RNAP, methods of purifying cyanophage Syn5 RNAP, methods of expressing cyanophage Syn5 RNAP, and in vitro transcription systems utilizing novel promoter sequences and Syn5 RNAP.

As used herein, the terms "nucleic acid molecule," "nucleic acid sequence," "nucleic acid fragment," "oligonucleotide," "oligonucleotide fragment" and "polynucleotide" are used interchangeably and are intended to include, but are not limited to, a polymeric form of nucleotides that may have various lengths, either deoxyribonucleotides or ribonucleotides, or analogs thereof. Nucleic acid molecules include single stranded DNA (ssDNA), double stranded DNA (dsDNA), single stranded RNA (ssRNA) and double stranded RNA (dsRNA). Different nucleic acid molecules may have different three-dimensional structures, and may perform various functions, known or unknown. Non-limiting examples of nucleic acid molecules include a gene, a gene fragment, a genomic gap, an exon, an intron, intergenic DNA (including, without limitation, heterochromatic DNA), messenger RNA (mRNA), transfer RNA, ribosomal RNA, ribozymes, small interfering RNA (siRNA), miRNA, small nucleolar RNA (snoRNA), cDNA, recombinant polynucleotides, branched polynucleotides, plasmids, vectors, isolated DNA of a sequence, isolated RNA of a sequence, nucleic acid probes, and primers. Nucleic acid molecules useful in the methods described herein may comprise natural nucleic acid sequences and variants thereof, artificial nucleic acid sequences, or a combination of such sequences.

An oligonucleotide sequence refers to a linear polymer of natural or modified nucleosidic monomers linked by phosphodiester bonds or analogs thereof. The term "oligonucleotide" usually refers to a shorter polymer, e.g., comprising from about 3 to about 100 monomers, and the term "polynucleotide" usually refers to longer polymers, e.g., comprising from about 100 monomers to many thousands of monomers, e.g., 10,000 monomers, or more. An "oligonucleotide fragment" refers to an oligonucleotide sequence that has been cleaved into two or more smaller oligonucleotide sequences. Oligonucleotides comprising probes or primers usually have lengths in the range of from 12 to 60 nucleotides, and more usually, from 18 to 40 nucleotides. Oligonucleotides and polynucleotides may be natural or synthetic. Oligonucleotides and polynucleotides include deoxyribonucleotides, ribonucleotides, and non-natural analogs thereof, such as anomeric forms thereof, peptide nucleic acids (PNAs), and the like, provided that they are capable of specifically binding to a target genome by way of a regular pattern of monomer-to-monomer interactions, such as Watson-Crick type of base pairing, base stacking, Hoogsteen or reverse Hoogsteen types of base pairing, or the like.

Usually nucleosidic monomers are linked by phosphodiester bonds. Whenever an oligonucleotide is represented by a sequence of letters, such as "ATGCCTG," it will be understood that the nucleotides are in 5' to 3' order from left to right and that "A" denotes deoxyadenosine, "C" denotes deoxycytidine, "G" denotes deoxyguanosine, "T" denotes deoxythymidine, and "U" denotes the ribonucleotide, uridine, unless otherwise noted. Usually oligonucleotides comprise the four natural deoxynucleotides; however, they may also comprise ribonucleotides or non-natural nucleotide analogs. It is clear to those skilled in the art when oligonucleotides having natural or non-natural nucleotides may be employed in methods and processes described herein. For example, where processing by an enzyme is called for, usually oligonucleotides consisting solely of natural nucleotides are required. Likewise, where an enzyme has specific oligonucleotide or polynucleotide substrate requirements for activity, e.g., single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al., *Molecular Cloning*, Second Edition (Cold Spring Harbor Laboratory, New York, 1989), and like references. Oligonucleotides and polynucleotides may be single stranded or double stranded.

Nucleic acid molecules may optionally include one or more non-standard nucleotide(s), nucleotide analog(s) and/or modified nucleotides. Examples of modified nucleotides include, but are not limited to diaminopurine, $S^2T$, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone.

The terms "nucleotide analog," "altered nucleotide" and "modified nucleotide" refer to a non-standard nucleotide, including non-naturally occurring ribonucleotides or deoxyribonucleotides. In certain exemplary embodiments, nucleotide analogs are modified at any position so as to alter certain chemical properties of the nucleotide yet retain the ability of the nucleotide analog to perform its intended function. Examples of positions of the nucleotide which may be derivitized include the 5 position, e.g., 5-(2-amino)propyl uridine, 5-bromo uridine, 5-propyne uridine, 5-propenyl uridine, etc.; the 6 position, e.g., 6-(2-amino) propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; 0- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310.

Nucleotide analogs may also comprise modifications to the sugar portion of the nucleotides. For example the 2' OH-group may be replaced by a group selected from H, OR, R, F, Cl, Br, I, SH, SR, $NH_2$, NHR, $NR_2$, COOR, or OR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. 2000 Apr. 10(2):117-21, Rusckowski et al. Antisense Nucleic Acid Drug Dev. 2000 Oct. 10(5):333-45, Stein, Antisense Nucleic Acid Drug Dev. 2001 Oct. 11(5): 317-25, Vorobjev et al. Antisense Nucleic Acid Drug Dev. 2001 Apr. 11(2): 77-85, and U.S. Pat. No. 5,684,143. Certain of the above-referenced modifications (e.g., phosphate group modifications) decrease the rate of hydrolysis of, for example, polynucleotides comprising said analogs in vivo or in vitro.

In certain exemplary embodiments, large polynucleotides are provided. In certain aspects, isolation techniques that maximize the lengths of polynucleotides (e.g., DNA molecules) obtained are used. For example, in situ lysis or deproteinization (e.g., with EDTA, detergent, protease, any combinations thereof and the like) after agarose embedding (as routinely performed for pulsed field gel electrophoresis) can be used to obtain polynucleotides.

Nucleic acid molecules may be isolated from natural sources or purchased from commercial sources. Oligonucleotide sequences may also be prepared by any suitable method, e.g., standard phosphoramidite methods such as those described by Beaucage and Carruthers ((1981) *Tetrahedron Lett.* 22: 1859) or the triester method according to Matteucci et al. (1981) *J. Am. Chem. Soc.* 103:3185), or by other chemical methods using either a commercial automated oligonucleotide synthesizer or high-throughput, high-density array methods known in the art (see U.S. Pat. Nos. 5,602,244, 5,574,146, 5,554,744, 5,428,148, 5,264,566, 5,141,813, 5,959,463, 4,861,571 and 4,659,774, incorporated herein by reference in its entirety for all purposes). Pre-synthesized oligonucleotides may also be obtained commercially from a variety of vendors.

Nucleic acid molecules may be obtained from one or more biological samples. As used herein, a "biological sample" may be a single cell or many cells. A biological sample may comprise a single cell type or a combination of two or more cell types. A biological sample further includes a collection of cells that perform a similar function such as those found, for example, in a tissue. Accordingly, certain aspects of the invention are directed to biological samples containing one or more tissues. As used herein, a tissue includes, but is not limited to, epithelial tissue (e.g., skin, the lining of glands, bowel, skin and organs such as the liver, lung, kidney), endothelium (e.g., the lining of blood and lymphatic vessels), mesothelium (e.g., the lining of pleural, peritoneal and pericardial spaces), mesenchyme (e.g., cells filling the spaces between the organs, including fat, muscle, bone, cartilage and tendon cells), blood cells (e.g., red and white blood cells), neurons, germ cells (e.g., spermatozoa, oocytes), amniotic fluid cells, placenta, stem cells and the like. A tissue sample includes microscopic samples as well as macroscopic samples.

In certain aspects, nucleic acid sequences expressed in, derived from or obtained from one or more organisms or host cells are provided. As used herein, the term "organism" includes, but is not limited to, a human, a non-human primate, a cow, a horse, a sheep, a goat, a pig, a dog, a cat, a rabbit, a mouse, a rat, a gerbil, a frog, a toad, a fish (e.g., *Danio rerio*) a roundworm (e.g., *C. elegans*) and any transgenic species thereof. As used herein, a "host cell" can be any cell derived or obtained from an organism. The terms "organism" and "host cell" further include, but are not limited to, a yeast (e.g., *S. cerevisiae*) cell, a yeast tetrad, a yeast colony, a bacterium, a bacterial colony, a virion, virosome, virus-like particle and/or cultures thereof, and the like.

In certain aspects, one or more biological samples are isolated from one or more subjects. As used herein, a "biological sample" may be a single cell or many cells. A biological sample may comprise a single cell type or a combination of two or more cell types. A biological sample further includes a collection of cells that perform a similar function such as those found, for example, in a tissue. As used herein, a tissue includes, but is not limited to, epithelial tissue (e.g., skin, the lining of glands, bowel, skin and organs such as the liver, lung, kidney), endothelium (e.g., the lining of blood and lymphatic vessels), mesothelium (e.g., the lining of pleural, peritoneal and pericardial spaces), mesenchyme (e.g., cells filling the spaces between the organs, including fat, muscle, bone, cartilage and tendon cells), blood cells (e.g., red and white blood cells), neurons, germ cells (e.g., spermatozoa, oocytes), amniotic fluid cells, placenta, stem cells and the like. A tissue sample includes microscopic samples as well as macroscopic samples. In certain aspects, a sample can be obtained from one or more of single cells in culture, metagenomic samples, embryonic stem cells, induced pluripotent stem cells, cancer samples, tissue sections, biopsies and the like, and any combinations of these.

In certain aspects of the invention, vectors and plasmids useful for transformation of a variety of host cells are provided. Vectors and plasmids are common and commercially available from companies such as Invitrogen Corp. (Carlsbad, Calif.), Stratagene (La Jolla, Calif.), New England Biolabs, Inc. (Beverly, Mass.) and Addgene (Cambridge, Mass.).

Certain aspects of the invention pertain to vectors, such as, for example, expression vectors. As used herein, the term "vector" refers to a nucleic acid sequence capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. By way of example, but not of limitation, a vector of the invention can be a single-copy or multi-copy vector, including, but not limited to, a BAC (bacterial artificial chromosome), a fosmid, a cosmid, a plasmid, a suicide plasmid, a shuttle vector, a P1 vector, an episome, YAC (yeast artificial chromosome), a bacteriophage or viral genome, or any other suitable vector. The host cells can be any cells, including prokaryotic or eukaryotic cells, in which the vector is able to replicate.

Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors."

In general, expression vectors of utility in recombinant DNA techniques are often in the form of plasmids. In the present specification, "plasmid" and "vector" can be used interchangeably. However, the invention is intended to include such other forms of expression vectors, such as viral vectors (e.g., replication defective retroviruses, adenoviruses and adeno-associated viruses), which serve equivalent functions.

In certain exemplary embodiments, an exogenous nucleic acid described herein is expressed in bacterial cells using a bacterial expression vector such as, e.g., a fosmid. A fosmid is a cloning vector that is based on the bacterial F-plasmid. The host bacteria will typically only contain one fosmid molecule, although an inducible high-copy on can be included such that a higher copy number can be obtained (e.g., pCC1FOS™, pCC2FOS™). Fosmid libraries are particularly useful for constructing stable libraries from complex genomes. Fosmids and fosmid library production kits are commercially available (EPICENTRE® Biotechnologies, Madison, Wis.). For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

In certain exemplary embodiments, the recombinant expression vectors comprise a nucleic acid sequence in a form suitable for expression of the nucleic acid sequence in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the foreign nucleic acid sequence encoding a plurality of ribonucleic acid sequences described herein is linked to the regulatory sequence(s) in a manner which allows for expression of the nucleic acid sequence. The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). It will be appreciated by those skilled in the art that the design of the expression vector can depend on such factors as the choice of the host cell to be transformed, the level of expression of protein desired, and the like.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

Cells according to the present disclosure include any cell into which foreign nucleic acids can be introduced and expressed as described herein. It is to be understood that the basic concepts of the present disclosure described herein are not limited by cell type. Cells according to the present disclosure include eukaryotic cells, prokaryotic cells, animal cells, plant cells, insect cells, fungal cells, archaeal cells, eubacterial cells, a virion, a virosome, a virus-like particle, a parasitic microbe, an infectious protein and the like. Cells include eukaryotic cells such as yeast cells, plant cells, and animal cells. Particular cells include bacterial cells. Other suitable cells are known to those skilled in the art.

Foreign nucleic acids (i.e., those which are not part of a cell's natural nucleic acid composition) may be introduced into a cell using any method known to those skilled in the art for such introduction. Such methods include transfection, transduction, infection (e.g., viral transduction), injection, microinjection, gene gun, nucleofection, nanoparticle bombardment, transformation, conjugation, by application of the nucleic acid in a gel, oil, or cream, by electroporation, using lipid-based transfection reagents, or by any other suitable transfection method. One of skill in the art will readily understand and adapt such methods using readily identifiable literature sources.

As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection (e.g., using commercially available reagents such as, for example, LIPOFECTIN® (Invitrogen Corp., San Diego, Calif.), LIPOFECTAMINE® (Invitrogen), FUGENE® (Roche Applied Science, Basel, Switzerland), JETPEI™ (Polyplus-transfection Inc., New York, N.Y.), EFFECTENE® (Qiagen, Valencia, Calif.), DREAMFECT™ (OZ Biosciences, France) and the like), or electroporation (e.g., in vivo electroporation). Suitable methods for transforming or transfecting host cells can be found in Sambrook, et al. (*Molecular Cloning: A Laboratory Manual.* 2nd, ed., Cold Spring harbor Laboratory, Cold Spring Harbor Laboratory Press, Cold Spring Harbor, N.Y., 1989), and other laboratory manuals.

Typically, the vector or plasmid contains sequences directing transcription and translation of a relevant gene or genes, a selectable marker, and sequences allowing autonomous replication or chromosomal integration. Suitable vectors comprise a region 5' of the gene which harbors transcriptional initiation controls and a region 3' of the DNA fragment which controls transcription termination. Both control regions may be derived from genes homologous to the transformed host cell, although it is to be understood that such control regions may also be derived from genes that are not native to the species chosen as a production host.

Initiation control regions or promoters, which are useful to drive expression of the relevant pathway coding regions in the desired host cell are numerous and familiar to those skilled in the art. Virtually any promoter capable of driving these genetic elements is suitable for the present invention including, but not limited to, lac, ara, tet, trp, $IP_L$, $IP_R$, T7, tac, and trc (useful for expression in *Escherichia coli* and *Pseudomonas*); the amy, apr, npr promoters and various phage promoters useful for expression in *Bacillus subtilis*, and *Bacillus licheniformis*; nisA (useful for expression in gram positive bacteria, Eichenbaum et al. *Appl. Environ. Microbiol.* 64(8):2763-2769 (1998)); and the synthetic P11 promoter (useful for expression in *Lactobacillus plantarum*, Rud et al., *Microbiology* 152:1011-1019 (2006)). Termination control regions may also be derived from various genes native to the preferred hosts.

Certain vectors are capable of replicating in a broad range of host bacteria and can be transferred by conjugation. The complete and annotated sequence of pRK404 and three related vectors-pRK437, pRK442, and pRK442(H) are available. These derivatives have proven to be valuable tools for genetic manipulation in gram negative bacteria (Scott et al., Plasmid 50(1):74-79 (2003)). Several plasmid derivatives of broad-host-range Inc P4 plasmid RSF1010 are also available with promoters that can function in a range of gram negative bacteria. Plasmid pAYC36 and pAYC37, have active promoters along with multiple cloning sites to allow for the heterologous gene expression in gram negative bacteria.

Chromosomal gene replacement tools are also widely available. For example, a thermosensitive variant of the broad-host-range replicon pWV101 has been modified to construct a plasmid pVE6002 which can be used to create gene replacement in a range of gram positive bacteria (Maguin et al., J. Bacteriol. 174(17):5633-5638 (1992)). Additionally, in vitro transposomes are available to create random mutations in a variety of genomes from commercial sources such as EPICENTRE® (Madison, Wis.).

Vectors useful for the transformation of *E. coli* are common and commercially available. For example, the desired genes may be isolated from various sources, cloned onto a modified pUC19 vector and transformed into *E. coli* host cells. Alternatively, the genes encoding a desired biosynthetic pathway may be divided into multiple operons, cloned into expression vectors, and transformed into various *E. coli* strains.

According to certain aspect of the invention, phages and their genetic material are provided. As used herein, the terms "phage" and "bacteriophage" are used interchangeably. Phage can be distinguished from each another based on their genetic composition and/or their virion morphology. Some phage have double stranded DNA genomes, including phage of the corticoviridae, lipothrixviridae, plasmaviridae, myroviridae, siphoviridae, sulfolobus shibate, podoviridae, tectiviridae and fuselloviridae families. Other phage have single stranded DNA genomes, including phage of the microviridae and inoviridae families. Other phage have RNA genomes, including phage of the leviviridae and cystoviridae families. Exemplary bacteriophage include, but are not limited to, Wphi, Mu, T1, T2, T3, T4, T5, T6, T7, P1, P2, P4, P22, fd, phi6, phi29, phiC31, phi80, phiX174, SP01, M13, MS2, PM2, SSV-1, L5, PRD1, Qbeta, lambda, UC-1, HK97, HK022 and the like.

Isolation, extraction or derivation of nucleic acid sequences may be carried out by any suitable method. Isolating nucleic acid sequences from a biological sample generally includes treating a biological sample in such a manner that nucleic acid sequences present in the sample are extracted and made available for analysis. Any isolation method that results in extracted nucleic acid sequences may be used in the practice of the present invention. It will be understood that the particular method used to extract nucleic acid sequences will depend on the nature of the source.

Methods of DNA extraction are well-known in the art. A classical DNA isolation protocol is based on extraction using organic solvents such as a mixture of phenol and chloroform, followed by precipitation with ethanol (J. Sambrook et al., "Molecular Cloning: A Laboratory Manual," 1989, $2^{nd}$ Ed., Cold Spring Harbour Laboratory Press: New York, N.Y.). Other methods include: salting out DNA extraction (P. Sunnucks et al., Genetics, 1996, 144: 747-756; S. M. Aljanabi and I. Martinez, Nucl. Acids Res. 1997, 25: 4692-4693), trimethylammonium bromide salts DNA extraction (S. Gustincich et al., BioTechniques, 1991, 11: 298-302) and guanidinium thiocyanate DNA extraction (J. B. W. Hammond et al., Biochemistry, 1996, 240: 298-300). A variety of kits are commercially available for extracting DNA from biological samples (e.g., BD Biosciences Clontech (Palo Alto, Calif.): Epicentre Technologies (Madison, Wis.); Gentra Systems, Inc. (Minneapolis, Minn.); MicroProbe Corp. (Bothell, Wash.); Organon Teknika (Durham, N.C.); and Qiagen Inc. (Valencia, Calif.)).

Methods of RNA extraction are also well known in the art (see, for example, J. Sambrook et al., "Molecular Cloning: A Laboratory Manual" 1989, $2^{nd}$ Ed., Cold Spring Harbour Laboratory Press: New York) and several kits for RNA extraction from bodily fluids are commercially available (e.g., Ambion, Inc. (Austin, Tex.); Amersham Biosciences (Piscataway, N.J.); BD Biosciences Clontech (Palo Alto, Calif.); BioRad Laboratories (Hercules, Calif.); Dynal Biotech Inc. (Lake Success, N.Y.); Epicentre Technologies (Madison, Wis.); Gentra Systems, Inc. (Minneapolis, Minn.); GIBCO BRL (Gaithersburg, Md.); Invitrogen Life Technologies (Carlsbad, Calif.); MicroProbe Corp. (Bothell, Wash.); Organon Teknika (Durham, N.C.); Promega, Inc. (Madison, Wis.); and Qiagen Inc. (Valencia, Calif.)).

Certain embodiments of the subject invention are directed to a first nucleic acid (e.g., a nucleic acid sequence encoding a Syn5 RNAP) or polypeptide sequence (e.g., a Syn5 RNAP) having a certain sequence identity or percent homology to a second nucleic acid or polypeptide sequence, respectively.

Techniques for determining nucleic acid and amino acid "sequence identity" are known in the art. Typically, such techniques include determining the nucleotide sequence of genomic DNA, mRNA or cDNA made from an mRNA for a gene and/or determining the amino acid sequence that it encodes, and comparing one or both of these sequences to a second nucleotide or amino acid sequence, as appropriate. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100.

An approximate alignment for nucleic acid sequences is provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov (1986) *Nucl. Acids Res.* 14:6745. An exemplary implementation of this algorithm to determine percent identity of a sequence is provided by the Genetics Computer Group (Madison, Wis.) in the "BestFit" utility application. The default parameters for this method are described in the *Wisconsin Sequence Analysis Package Program Manual*, Version 8 (1995) (available from Genetics Computer Group, Madison, Wis.).

One method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages, the Smith-Waterman algorithm can be employed where default parameters are used for the scoring table (for example, gap open penalty of 12, gap extension penalty of one, and a gap of six). From the data generated the "match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+PDB+GenBank CDS translations+Swiss protein+Spupdate+PIR. Details of these programs can be found at the NCBI/NLM web site.

Alternatively, homology can be determined by hybridization of polynucleotides under conditions that form stable duplexes between homologous regions, followed by digestion with single-stranded-specific nuclease(s), and size determination of the digested fragments. Two DNA sequences, or two polypeptide sequences are "substantially homologous" to each other when the sequences exhibit at least about 80%-85%, at least about 85%-90%, at least about 90%-95%, or at least about 95%-98%, or about 95%, about 96%, about 97%, about 98%, or about 99% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., *Molecular Cloning: A Laboratory Manual*, Second Edition, (1989) Cold Spring Harbor, N.Y.; *Nucleic Acid Hybridization: A Practical Approach*, editors B. D. Hames and S. J. Higgins, (1985) Oxford; Washington, D.C.; IRL Press.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., supra). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, Nucleic Acid Hybridization, supra).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as varying wash conditions. The selection of a particular set of hybridization conditions is selected following standard methods in the art (see, for example, Sambrook et al., supra).

As used herein, the term "hybridizes under stringent conditions" is intended to describe conditions for hybridization and washing under which nucleotide sequences at least 60% identical to each other typically remain hybridized to each other. In one aspect, the conditions are such that sequences at least about 70%, at least about 80%, at least about 85% or 90% or more identical to each other typically remain hybridized to each other. Such stringent conditions are known to those skilled in the art and can be found in *Current Protocols in Molecular Biology*, John Wiley & Sons, NY (1989), 6.3.1-6.3.6. A non-limiting example of stringent hybridization conditions are hybridization in 6× sodium chloride/sodium citrate (SSC) at about 45° C., followed by one or more washes in 0.2×SSC, 0.1% SDS at 50° C., at 55° C., or at 60° C. or 65° C.

In certain exemplary embodiments, a polymerase of the subject invention (e.g., a cyanophage Syn5 RNAP) includes one or more protein tags. As used herein, the term "protein tag" refers to a heterologous polypeptide sequence linked to a polymerase of the invention. Protein tags include, but are not limited to, Avi tag (GLNDIFEAQKIEWHE) (SEQ ID NO:8), calmodulin tag (KRRWKKNFIAVSAANRFK-KISSSGAL) (SEQ ID NO:9), FLAG tag (DYKDDDDK) (SEQ ID NO:10), HA tag (YPYDVPDYA) (SEQ ID NO:11), His tag (HHHHHH) (SEQ ID NO:12), Myc tag (EQKLISEEDL) (SEQ ID NO:13), S tag (KETAAAKFER-QHMDS) (SEQ ID NO:14), SBP tag (MDEK-TTGWRGGHVVEGLAGELEQLRARLEHHPQGQREP) (SEQ ID NO:15), Softag 1 (SLAELLNAGLGGS) (SEQ ID NO:16), Softag 3 (TQDPSRVG) (SEQ ID NO:17), V5 tag (GKPIPNPLLGLDST) (SEQ ID NO:18), Xpress tag (DLYDDDDK) (SEQ ID NO:19), Isopeptag (TDKDM-TITFTNKKDAE) (SEQ ID NO:20), SpyTag (AHIVMV-DAYKPTK) (SEQ ID NO:21), and streptactin tag (Strep-tag II: WSHPQFEK) (SEQ ID NO:7).

As used herein, a "kit" refers to any delivery system for delivering materials or reagents for carrying out a method of the invention. In the context of assays, such delivery systems include systems that allow for the storage, transport, or delivery of reaction reagents (e.g., enzymes (e.g., a polymerase such as, for example, cyanophage Syn5 RNAP), nucleotides, buffers, etc. in the appropriate containers) and/or supporting materials (e.g., written instructions for performing the assay (e.g., in vitro transcription), etc.) from one location to another. For example, kits include one or more enclosures (e.g., boxes) containing the relevant reaction reagents and/or supporting materials for assays of the invention. Such contents may be delivered to the intended recipient together or separately. For example, a first container may contain an enzyme (e.g., enzymes (e.g., a polymerase such as, for example, cyanophage Syn5 RNAP)) for use in an assay, while a second container contains nucleotides.

This invention is further illustrated by the following examples, which should not be construed as limiting. The contents of all references, patents and published patent applications cited throughout this application are hereby incorporated by reference in their entirety for all purposes.

Example I

Materials and Methods

Oligonucleotides were obtained from Integrated DNA Technology. DNA purification kits and Ni-NTA resin were from Qiagen. Cellulose phosphate resin and DE81 filter disks were from Whatman. Preparative Superdex S200 for gel filtration and ion exchange column Mono Q were from GE Healthcare.

Restriction endonucleases, Deep Vent® polymerase, Phusion® High-Fidelity DNA polymerase, T4 DNA ligase, DNase I, RNase I, and T7 RNAP were from New England Biolabs. Radiolabeled nucleotides were from Perkin Elmer. $FeCl_2.4H_2O$ (99.0%) and other chemicals were from Sigma-Aldrich. RNA Clean & Concentrator™-5 kit was from ZYMO Research. RNaseOUT™ Recombinant Ribonuclease Inhibitor was from Invitrogen. Yeast inorganic pyrophosphatase was from Sigma-Aldrich. Nucleoside-5'-triphosphates were from USB except that 5-methylcytidine-5'-triphosphate and pseudouridine-5'-triphosphate were from Trilink. *E. coli* total aminoacyl-tRNA synthetases were purchased from Sigma-Aldrich.

Protein Purification

Syn5 genomic DNA was isolated from Syn5 particles purified by CsCl centrifugation (17). DNA fragments encoding Syn5 RNAP were amplified from the Syn5 genome using the primers listed in Table 1 (Example III) and inserted into plasmid pET24a between the NdeI and NotI sites. Plasmids were used to transform *E. coli* BL21(DE3). The bacteria were cultured in LB medium containing 50 □g/ml kanamycin at 37° C. until they reached an $OD_{600}$ of approximately 1.2. The gene for Syn5 RNAP was induced by the addition of 0.5 mM IPTG at 28° C. and incubation continued for 3 hr. Cells were harvested, resuspended in 50 mM sodium phosphate, pH 8.0 and 100 mM NaCl, and lysed by three cycles of freeze-thaw in the presence of 0.5 mg/ml lysozyme. Cleared lysate was collected by centrifugation. His-tagged Syn5 RNAP was isolated from the lysate using Ni-NTA agarose chromatography according to the standard Qiagen His-tagged protein purification procedure. Ammonium sulfate (40% w/v) was added to a pool of the fractions containing predominately RNAP to precipitate the protein. The pellet was then dissolved in 1 ml 20 mM Tris-HCl pH 7.5, 50 mM NaCl, 0.5 mM DTT, and 0.5 mM EDTA and the RNAP was further purified by gel filtration chromatography on a 200 mL preparative Superdex S200 column. Fractions eluting from this column were analyzed on SDS-PAGE gels and those containing the RNAP were pooled. This pool was then loaded onto a cellulose phosphate column. The column was washed extensively with 20 mM potassium phosphate pH 7.5, 1 mM DTT, 1 mM EDTA, 10% glycerol, and 20 mM KCl and eluted with the same buffer containing a 0.02 to 1 M KCl gradient. Syn5 RNAP eluted at ~0.7 M KCl; fractions containing the protein were pooled and dialyzed against 20 mM potassium phosphate pH 7.5, 0.1 mM DTT, 0.1 mM EDTA, and 50% glycerol. The fractions at each step containing Syn5 RNAP with the least amount of contaminating proteins are shown in FIG. 1. For the purification of Syn5 RNAP lacking a histidine tag, the order of purification steps was adjusted to cellulose phosphate chromatography, ammonium sulfate precipitation, gel filtration chromatography, and an additional step consisting of Mono Q ion-exchange column chromatography. Syn5 RNAP eluted at ~0.3 M NaCl from the Mono Q column. The yield of His-tagged Syn5 RNAP was 500 □g per gram of wet cells while the yield of non-tagged Syn5 RNAP was 5 □g per gram of wet cells.

His-tagged Syn5 RNAP was expressed from a pET24 vector harboring His-tagged Syn5 RNAP gene between the NdeI and NotI sites (Zhu et al. (2013)) and purified by Ni-NTA agarose and gel filtration chromatography. 2 M NaCl was present during the purification procedure and was removed by dialysis as the protein was finally concentrated. E. coli BL21(DE3) cells over-producing the protein were cultured in 2 L LB medium containing 50 □g/ml kanamycin at 37° C. until they reached an $OD_{600}$ of approximately 1.2. The gene for Syn5 RNAP was induced by the addition of 0.5 mM IPTG at 16° C. and incubation continued for 3 hr. Cells were harvested, resuspended in 50 mM sodium phosphate, pH 8.0, 100 mM NaCl, and lysed by three cycles of freeze-thaw in the presence of 0.5 mg/ml lysozyme. 2 M NaCl was then added to the lysed cells and the cleared lysate was collected by centrifugation. 2 ml Ni-NTA agarose was added to the clear lysate and mixed at 4° C. overnight. The resin was then washed with 30 ml of wash buffer (50 mM sodium phosphate, pH 8.0, 2 M NaCl, and 20 mM imidazole). Syn5 RNAP was eluted from the column with 60 ml gradient (20 to 250 ml imidazole) in 50 mM sodium phosphate, pH 8.0, 2 M NaCl. Fractions were analyzed on SDS-PAGE gels and those with Syn5 RNAP over 80% were collected and concentrated with Amicon Ultra-15 Centrifugal Filter Units (Millipore) to 1 ml. Concentrated solution was directed loaded onto a 200 mL preparative Superdex S200 column. The elution buffer for gel filtration contains 20 mM Tris-HCl pH 7.5, 2 M NaCl, 0.5 mM DTT, and 0.5 mM EDTA. Fractions were analyzed on SDS-PAGE gels and those with homogenous Syn5 RNAP were pooled. The pooled protein solution was concentrated by Amicon Ultra-15 Centrifugal Filter followed by dialysis against 50 mM Tris-HCl pH 8.0, 100 mM NaCl, 20 mM β-ME, 1 mM EDTA, 50% glycerol, and 0.1% Triton® X-100 at −20° C. Dilutions for enzyme assays were made using the final dialysis buffer. The protein remains soluble even at a high concentration over 400 □M. The yield of His-tagged Syn5 RNAP following this procedure was 5 mg per gram of wet cells. His-tagged T7 RNAP was purified from E. coli BL21 (DE3) harboring plasmid pET28a with the T7 RNAP gene inserted between the NdeI and HindIII sites, using Ni-NTA and DEAE ion-exchange chromatography.

DNA Templates

Syn5 genomic DNA was prepared according to a previous report (13,17). Primers used to amplify the Syn5 RNAP gene and the transcription templates are listed in Table 1. PCR reactions for DNA shorter than 3 kb were carried out using Deep Vent® DNA polymerase while reactions for DNA longer than 3 kb were carried out using Phusion® High-Fidelity DNA polymerase (New England Biolabs). PCR products were purified using Qiagen Gel Extraction Kits and DNA concentrations were determined by measuring the $A_{260}$. Short transcription templates were prepared by annealing complementary synthetic DNA oligonucleotides whose sequences are shown in Table 1.

DNA Templates for Transcription Assays

DNA templates for transcription assays were either plasmids or dsDNA fragments made of synthesized oligonucleotides. To test the processivity of Syn5 and T7 RNAP, a single Syn5 or T7 promoter plus 3 guanosine downstream of the promoter (Syn5 5'-ATTGGGCACCCGTAAGGG-3' (SEQ ID NO:1) or T7 5'-TAATACGACTCACTATAGGG-3') (SEQ ID NO:2) was inserted between the BamHI and XbaI sites of plasmid pUC19 to form pUC19-S5P or pUC19-T7P. The templates for run-off tRNA$^{Arg}$ synthesis were formed by annealing of two complementary synthesized DNA oligos of which sequences are as following:

S5P-tDNAR:
(SEQ ID NO: 3)
5'-GCCATTGGGCACCCGTAAGCATCCGTAGTTCAGCTGGATAGAGTA

CTCGGCTACGAACCGAGCGGTCGGAGGTTCGAATCCTCCCGGATGCAC

CA-3'
and

T7P-tDNAR:
(SEQ ID NO: 4)
GCCTAATACGACTCACTATAGCATCCGTAGTTCAGCTGGATAGAGTAC

TCGGCTACGAACCGAGCGGTCGGAGGTTCGAATCCTCCCGGATGCACC

A.

Two templates are same except for the promoter region.

Figure 12A:
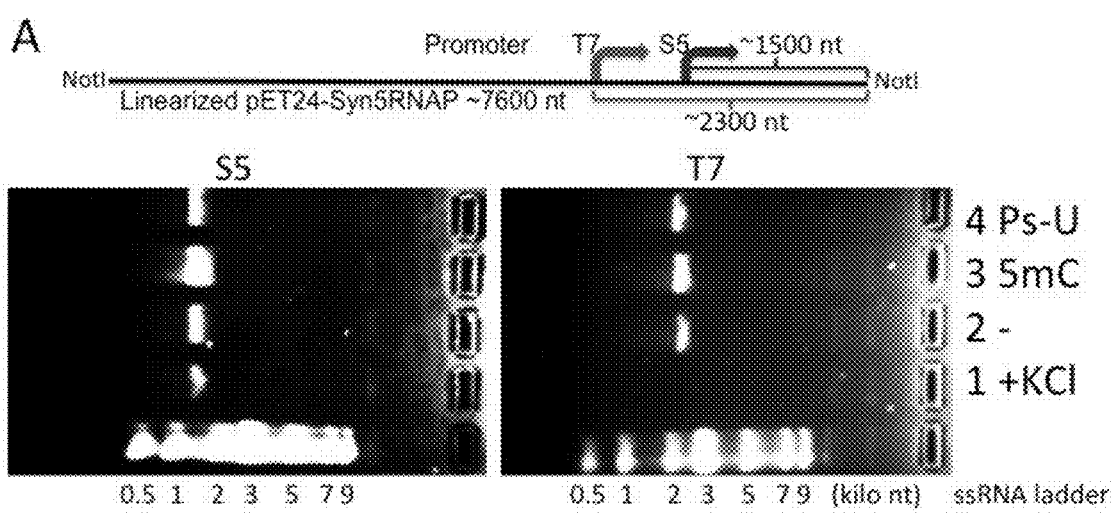
FIGS. 12A-12B depict synthesis of long run-off product and the incorporation of modified nucleotides by Syn5 and T7 RNA polymerase. A) On the linearized plasmid template as shown in the schematic, the production of RNA by either RNA polymerase (10 nM) was analyzed on agarose gel as lane 2. Lane 1 shows the same RNA synthesis in the presence of 160 mM KCl. Lane 3 and 4 show the same RNA synthesis when CTP was replaced by 5mCTP and UTP by Ps-UTP, respectively. B) Incorporation of UTP or Ps-UTP into small RNA by 22, 67, and 200 nM Syn5 and T7 RNA polymerase as analyzed by denaturing TBE polyacrylamide gel. Full-length run-off product and the N+1 product are shown.

The plasmid pET24 harboring the Syn5 RNAP gene (pET24-S5RNAP) that contains a single Syn5 promoter in the RNAP gene and a single T7 promoter preceding the gene was used for filter binding assay as shown in FIG. 8. pET24-S5RNAP was also linearized by EcoRI treatment and recovered by gel extraction to serve as template for FIG. 12A.

Transcription Assays

For the gel assay results shown in FIGS. 1, 2, 3, and 13, reaction mixtures (20 µl) contained 40 mM Tris-HCl (pH 7.9), 6 mM $MgCl_2$, 2 mM spermidine, 10 mM DTT, 200 □M□□□P, GTP and UTP, 10 □M [□-$^{32}$P]CTP, 1.5 U/□l RNaseOUT™ recombinant ribonuclease inhibitor (Invitrogen), 100 nM Syn5 or T7 RNAP, and DNA templates as described in the figure legends (either 2 nM phage genomic DNA, 4 nM purified PCR products, or 1 □M synthetic dsDNA fragments). Reaction mixtures were incubated at 24° C. for 30 min. The reaction mixtures described in FIG. 6 contained 40 mM Tris-HCl (pH 8.0), 200 □M□□□P, GTP and UTP, 10 □M [□-$^{32}$P]CTP, 1.5 U/□l RNaseOUT™, 50 nM Syn5 RNAP, DNA templates, and various amounts of $MgCl_2$, $FeCl_2$, $MnCl_2$ and KCl as described in the figure legends. After 30 min incubations at 24° C., one unit of RQ1 RNase-Free DNase (Promega) was added to each reaction mixture and incubated for an additional 20 min at 37° C. to remove the DNA templates. Reactions were then terminated by the addition of 8 □l of loading dye containing 95% formamide and 40 mM EDTA. Samples were then heated at 90° C. for 1 min and loaded onto either 10% or 25% TBE-Urea denaturing gels. After electrophoresis, gels were dried and analyzed using a Fuji BAS 1000 Bioimaging Analyzer.

Filter-binding assays were used for the results shown in FIGS. 4, 5 and 7. Basic reaction mixtures contained 40 mM Tris-HCl (pH 8.0 unless otherwise specified), 2 mM spermidine, 10 mM DTT, 200 □M□ GTP, C□P, UTP and $^3$H-ATP (20 cpm/pmole), 1.5 U/□l RNaseOUT™, 50 nM Syn5 or T7 RNAP and 4 nM plasmid pET24 DNA harboring the Syn5 RNAP gene (pET24-S5RNAP) that contains a single Syn5 promoter in the RNAP gene and a single T7 promoter preceding the gene. Reaction mixtures were incubated at 24° C. unless otherwise specified.

Various salts and co-factors were added as indicated in the figure legends. For the assays described in FIG. 7, reaction mixtures contained 40 mM Tris-HCl (pH 8.0), 6 mM MgCl$_2$, 2 mM spermidine, 10 mM DTT, 20 nM Syn5 or T7 RNAP, 20 nM pET24-S5RNAP DNA, 1 mM $^3$H-ATP (20 cpm/pmole), CTP, UTP (or GTP), and varying amounts of GTP (or UTP). 160 mM KCl was added for the Syn5 RNAP reactions. After various times the reactions were stopped by the addition of 20 mM EDTA. 4 μl of the mixtures were then loaded onto Whatman DE81 filter paper disks and the disks were washed to remove the unincorporated $^3$H-ATP. The amount of insoluble $^3$H-AMP, corresponding to nucleotides incorporated into newly synthesized RNA, was measured using a scintillation counter. The data were analyzed using Prism software.

Figure 8A:
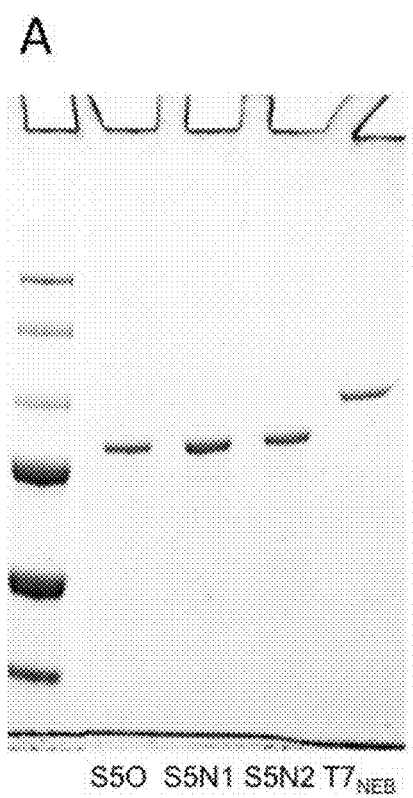
FIGS. 8A-8B depict RNA polymerases described further herein. A) SDS-PAGE gel of Syn5 RNA polymerase purified as previously reported (S50, 18), newly purified Syn5 RNA polymerase using Ni-NTA chromatography in the presence of 2 M NaCl (S5N1), newly purified Syn5 RNA polymerase purified using Ni-NTA and gel filtration chromatography in the presence of 2 M NaCl (S5N2), and T7 RNA polymerase. B) Incorporation of AMP at RT by 50 nM RNA polymerases shown in A). A plasmid with both a Syn5 and T7 promoter was used as template for transcription.
Figure 8B:
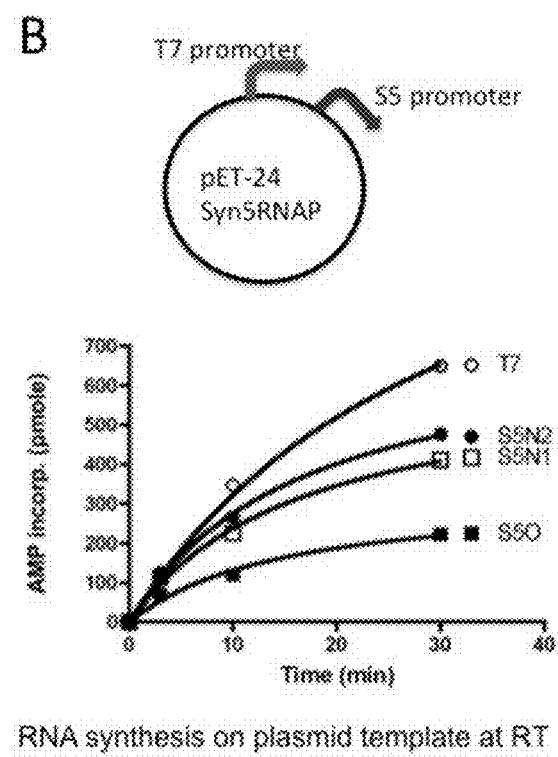

Reactions for FIG. 8B contained 40 mM Tris-HCl pH 8.0, 2 mM spermidine, 10 mM DTT, 200 μM GTP, CTP, UTP and $^3$H-ATP (20 cpm/pmole), 1.5 U/μl RNaseOUT™, 50 nM Syn5 or T7 RNAP and 4 nM plasmid pET24-S5 RNAP. Reaction mixtures were incubated at room temperature (RT, ~24° C.). After various times the reactions were stopped by the addition of 20 mM EDTA. 4 μl of the mixtures were then loaded onto Whatman DE81 filter paper disks and the disks were washed to remove the unincorporated $^3$H-ATP. The amount of insoluble $^3$H-AMP, corresponding to nucleotides incorporated into newly synthesized RNA, was measured using a scintillation counter. The data were analyzed using Prism software.

For the results shown in FIG. 9, reaction mixtures (10 μl) contained 40 mM Tris-HCl pH 8.0, 6 mM MgCl$_2$, 2 mM spermidine, 10 mM DTT, 600 μM NTP, GTP, CTP, and UTP, 1.5 U/μl RNaseOUT™ recombinant ribonuclease inhibitor, 0.04 U/μl yeast inorganic pyrophosphatase, 10 nM pUC19-Syn5P3G or pUC19-T7P3G, 10 nM Syn5 or T7 RNAP and various amount of KCl as noted in the figure or described in the figure legend. After 1 hr incubations at RT, one unit of DNase I was added to each reaction mixture and incubated for an additional 15 min at 37° C. to remove the DNA templates. For FIGS. 8A-8C, 2 μl reaction mixture was directly mixed with native loading dye and loaded onto 1.6% TAE agarose gel. For FIGS. 8D-8F, RNA products were purified with RNA Clean & Concentrator™-5 kit into a final solution of 10 μl and 5 μl each was mixed with 5 μl denaturing RNA loading dye (New England Biolabs). Samples were then heated at 65° C. for 5 min and loaded onto 1.6% TAE agarose gel. RNA products were visualized by ethidium bromide staining.

For the results shown in FIG. 10, reaction mixtures (10 μl) contained 40 mM Tris-HCl pH 8.0, 6 mM MgCl$_2$, 2 mM spermidine, 10 mM DTT, 200 μM NTP, GTP and UTP, 10 μM [α-$^{32}$P]CTP, 1.5 U/μl RNaseOUT™ recombinant ribonuclease inhibitor, 0.5 μM DNA templates S5P-tDNAR or T7P-tDNAR, 100 nM Syn5 or T7 RNAP, and various amount of KCl as noted in the figure. Reactions were carried out at various temperatures of 16° C., room temperature, or 37° C. for 30 min before adding of one unit of DNase I to each reaction mixture and an additional incubation of 15 min at 37° C. Reactions were then terminated by the addition of 4 μl of loading dye containing 95% formamide and 40 mM EDTA. Samples were then heated at 90° C. for 1 min and 4 μl sample each was loaded onto 15% TBE-Urea denaturing polyacrylamide gels. After electrophoresis, gels were dried and analyzed using a Fuji BAS 1000 Bioimaging Analyzer.

Figure 11A:
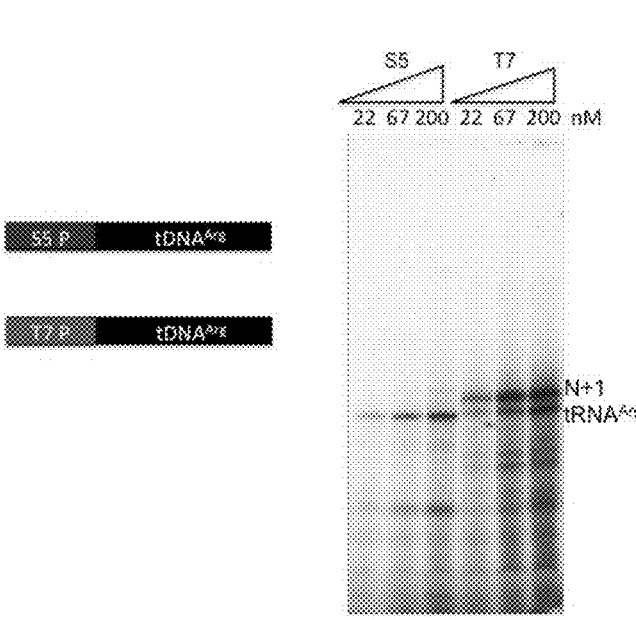
FIGS. 11A-11B depict synthesis of tRNA$^{Arg}$ by Syn5 and T7 RNA polymerase. A) Synthesis of tRNA$^{Arg}$ at analytical scale by various amounts of Syn5 and T7 RNA polymerase. Using radioactively labeled CTP, the tRNA$^{Arg}$ and N+1 product (as marked) produced by 22, 67, 200 nM Syn5 and T7 RNA polymerase at 37° C. are shown. The schematic diagram shows the constructs for DNA templates for transcription assays. The DNA encoding E. coli tRNA$^{Arg}_{ACG}$ is directly downstream of a Syn5 or T7 promoter for the cognate RNA polymerase to synthesize run-off tRNA transcript. B) Synthesis of tRNA$^{Arg}$ at preparative scale by Syn5 and T7 RNA polymerase. The sequencing gel is showing the analysis of the total RNA products by Syn5 and T7 RNAP at 37° C. in a 200 □l reaction. RNAs were purified by either ZYMO RNA clean kit or phenol/chloroform extraction followed by ethanol precipitation (P/C/E), as noted on top of the gel. The native tRNA$^{Arg}$ (with modifications) overexpressed and purified from E. coli cells was used as a size marker. The two major bands in the total RNAs are tRNA$^{Arg}$ and N+1 product as marked. The inset curve shows the charging of arginine on tRNA$^{Arg}$ from total RNAs (purified native tRNA$^{Arg}$, Syn5 RNA polymerase products, or T7 RNA polymerase products) by E. coli total aminoacyl-tRNA synthetases with time increased. The maximum charging capacity at 30 min was turned into amount of functional tRNA$^{Arg}$ molecules (arginine and tRNA$^{Arg}$ are at 1:1 ratio in the aminoacylation product), and then the percentage of functional tRNA$^{Arg}$ molecules in total RNA transcripts was calculated and showed as column chart in the figure.

For the results shown in FIG. 11A, reaction mixtures (10 μl) containing 40 mM Tris-HCl pH 8.0, 6 mM MgCl$_2$, 2 mM spermidine, 10 mM DTT, 200 μM NTP, GTP and UTP, 10 μM [α-$^{32}$P]CTP, 1.5 U/μl RNaseOUT™ recombinant ribonuclease inhibitor, 0.5 μM DNA templates S5P-tDNAR or T7P-tDNAR, and various amount of Syn5 or T7 RNAP were incubated at 37° C. for 30 min before adding of one unit of DNase I to each reaction mixture and an additional incubation of 15 min at 37° C. Reactions were then terminated by the addition of 4 μl of loading dye containing 95% formamide and 40 mM EDTA. Samples were then heated at 90° C. for 1 min and 4 μl sample each was loaded onto 6% TBE-Urea denaturing polyacrylamide gel. After electrophoresis, gels were dried and analyzed using a Fuji BAS 1000 Bioimaging Analyzer. For the results shown in FIG. 11B, 200 μl reactions containing 40 mM Tris-HCl pH 8.0, 6 mM MgCl$_2$, 2 mM spermidine, 10 mM DTT, 600 μM NTP, GTP CTP and UTP each, 1.5 U/μl RNaseOUT™ recombinant ribonuclease inhibitor, 0.04 U/μl yeast inorganic pyrophosphatase, 0.5 μM DNA templates S5P-tDNAR or T7P-tDNAR, 100 nM Syn5 or T7 RNAP were incubated at 37° C. for 2 hours before adding of 10 unit of DNase I to each reaction mixture and an additional incubation of 20 min at 37° C. RNA products were then purified with RNA Clean & Concentrator™-5 kit or traditional phenol chloroform extraction/ethanol precipitation into 30 μl H$_2$O. RNA quantification was based on OD260 measurement using NANOPHOTOMETER (IMPLEN). 5 μl final solution from Syn5 RNAP reaction and 1 μl from T7 RNAP reaction were mixed with denaturing dye, heated at 90° C. for 1 min and loaded onto 15% TBE-Urea denaturing polyacrylamide gel. RNAs were visualized by ethidium bromide staining. Native tRNA$_{Arg}$ expressed in and purified from *E. coli* (Zhu et al. (2012)) was loaded as a marker.

For the results shown in FIG. 12A, reaction mixtures (10 μl) contained 40 mM Tris-HCl pH 8.0, 6 mM MgCl$_2$, 2 mM spermidine, 10 mM DTT, 600 μM NTP, GTP, CTP (or 5Me-CTP), and UTP (or Pseudo-UTP), 1.5 U/μl RNaseOUT™ recombinant ribonuclease inhibitor, 0.04 U/μl yeast inorganic pyrophosphatase, 10 nM linearized (NotI treated) pET24-Syn5RNAP, 0 or 160 mM KCl, and 10 nM Syn5 or T7 RNAP. Syn5 reaction was carried out at RT and T7 at 37° C. RNA products were then purified with RNA Clean & Concentrator™-5 kit into a final solution of 10 μl and 5 μl each was mixed with 5 μl denaturing RNA loading dye. Samples were then heated at 65° C. for 5 min and loaded onto 1.6% TAE agarose gel. RNA products were visualized by ethidium bromide staining. For FIG. 12B, reaction mixtures (10 μl) containing 40 mM Tris-HCl pH 8.0, 6 mM MgCl$_2$, 2 mM spermidine, 10 mM DTT, 200 μM NTP, GTP and UTP (or Pseudo-UTP), 10 μM [α-$^{32}$P]CTP, 1.5 U/μl RNaseOUT™ recombinant ribonuclease inhibitor, 0.5 μM DNA templates S5P-tDNAR or T7P-tDNAR, and various amount of Syn5 or T7 RNAP were incubated at RT (for Syn5 RNAP) or 37° C. (for T7 RNAP) for 30 min before adding of one unit of DNase I to each reaction mixture and an additional incubation of 15 min at 37° C. Reactions were then terminated by the addition of 4 μl of loading dye containing 95% formamide and 40 mM EDTA. Samples were then heated at 90° C. for 1 min and 4 μl sample each was loaded onto 6% TBE-Urea denaturing polyacrylamide gel. After electrophoresis, gels were dried and analyzed using a Fuji BAS 1000 Bioimaging Analyzer.

tRNA Aminoacylation Assay tRNA aminoacylation assay was performed as described previously (Tan et al.). A reaction containing 100 mM Tris-HCl, pH 7.5, 30 mM KCl, 12 mM MgCl$_2$, 0.5 mM DTT, 4 mM ATP, 0.2 μM RNA (purified native *E. coli* tRNA$^{Arg}$ (Zhu et al. (2012)), or purified tRNA$^{Arg}$ transcripts from Syn5 or T7 RNAP reaction using RNA Clean & Concentrator™-5 kit), 15 μM [³H] arginine (15 Ci/mmol), and 4 μM *E. coli* total aminoacyl-tRNA synthetases was incubated at 37° C. for the indicated time period. 5 μl reaction mixtures were spotted onto Whatman DE(81) filters and reactions stopped by 10% TCA solution containing 0.5 mM arginine. The filters were washed twice with 10% TCA and once with ethanol, and then dried. The amount of amino acid charged to tRNA was determined by measuring radioactivity remained on the filters.

Example II

Overproduction and Purification of Syn5 RNAP

The Syn5 RNAP gene was cloned into a plasmid under the control of a T7 promoter and overproduced the Syn5 RNAP in *E. coli*. The target protein is soluble and has been purified to greater than 80% purity using cellulose phosphate chromatography, ammonium sulfate precipitation, gel filtration chromatography, and anion-exchange chromatography (FIG. 1A, lane 1). The Syn5 RNAP binds tightly (eluting at 0.7 M KCl) to cellulose phosphate resulting in the greatest purification. The protein could not be further purified despite using chromatography on Sepharose-Blue, ATP-agarose, and DEAE cellulose. Therefore, a hybrid gene fusion that attached a His-Tag on the N-terminus of Syn5 RNAP was constructed. This tagged-protein was purified to apparent homogeneity by Ni-NTA agarose chromatography, gel filtration chromatography, and cellulose phosphate chromatography (FIG. 1A, lane 4). Fractions from each step of this procedure were collected and their purity established by gel electrophoresis and staining with Coomassie Blue (FIG. 1A, lanes 2 and 3). During purification, fractions from each step were assayed for RNAP activity by transcription on Syn5 genomic DNA (FIG. 1B). The increased protein purity significantly increased the yield of RNA transcripts. Without intending to be bound by scientific theory, this was most likely due to the removal of contaminating ribonuclease activity (FIG. 1B).

The non-tagged Syn5 RNAP had biochemical properties similar to the His-tagged RNAP although it synthesized fewer transcripts compared to the tagged protein (FIG. 1B, lane 1 versus lane 4). Again, the apparent decrease in RNAP activity probably reflects the lower purity of the non-tagged protein, and thus the presence of contaminating ribonuclease activity. The results shown in the following sections were all carried out using the His-tagged Syn5 RNAP.

Example III

Identification of the Syn5 RNAP Promoter

Syn5 shares many features in common with other T7 phage groups including morphology, genome size, and the presence of a terminal redundancy at the two ends of its genome (Pope et al.). Another common feature is their transcription system. The phages encode their own RNAP that initiate transcription at conserved promoters distributed along the genome (Chen et al. (2005)). Bioinformatics identified a 12 bp sequence 5'-CCTTAATTAACT-3' (SEQ ID NO:5) in the middle/late portion of the Syn5 genome, the only sequence that appears several times within the genome (Pope et al.).

A number of early Syn5 genes appear to have sigma70-like promoters, suggesting that the host RNAP is responsible for their transcription. Id. By analogy to other T7-like phages, the genes downstream of the RNAP are most likely to be transcribed from Syn5 promoters. Therefore, in order to identify the Syn5 promoters, overlapping DNA fragments were prepared covering the entire region that encodes the predicted DNA metabolism proteins downstream of the RNAP gene. These fragments were then screened for promoters using an in vitro transcription assay with the purified Syn5 RNAP (FIG. 2A). Syn5 RNAP was only active on one of the templates, the template containing the RNAP gene itself. T7 phage has a promoter immediately after its RNAP gene, and thus it is reasonable that Syn5 has a promoter to transcribe its downstream genes. However, in contrast to the single promoter found in Syn5 over this region, T7 has 10 promoters distributed over the analogous region.

Figure 13A:
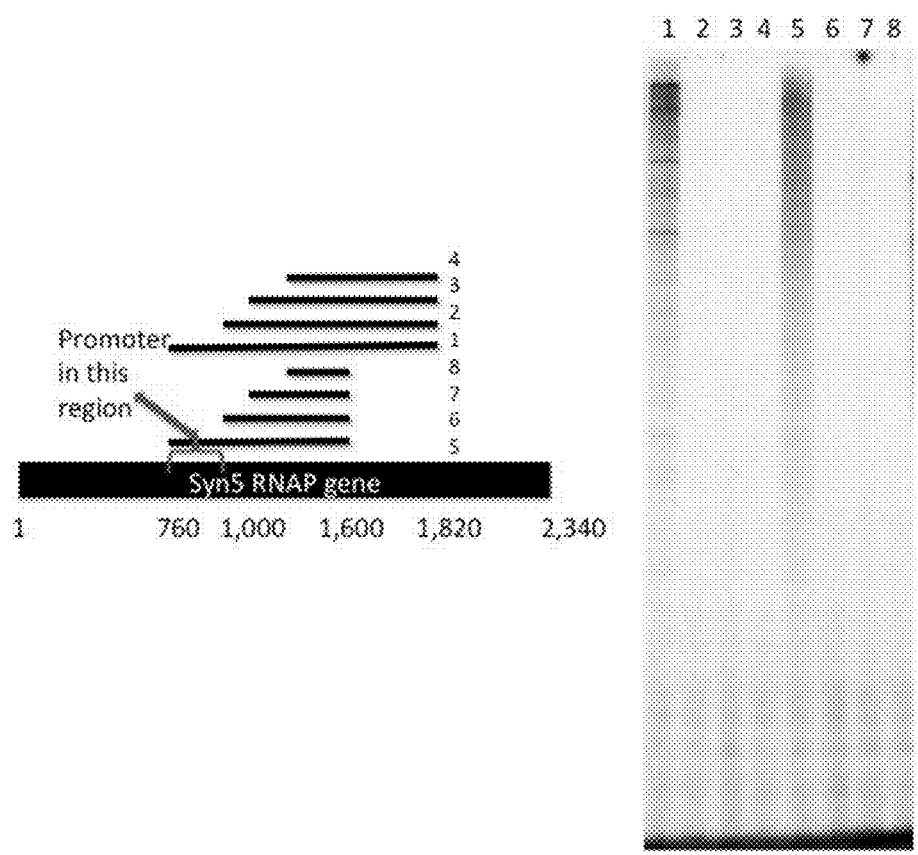
FIGS. 13A-13B depict the location of the Syn5 promoter in the Syn5 RNAP gene. A) Two sets of PCR fragments both confirmed that the promoter was in the region between the $760^{th}$ and $1000^{th}$ nucleotides in the RNAP gene (lane 1 vs. lane 2; lane 5 vs. lane 6). B) Two sets of PCR fragments both confirmed that the promoter starts from a small region between the $797^{th}$ and $842^{nd}$ nucleotides in the RNAP gene (lane 2 vs. lane 3; lane 8 vs. lane 9).
Figure 13B:
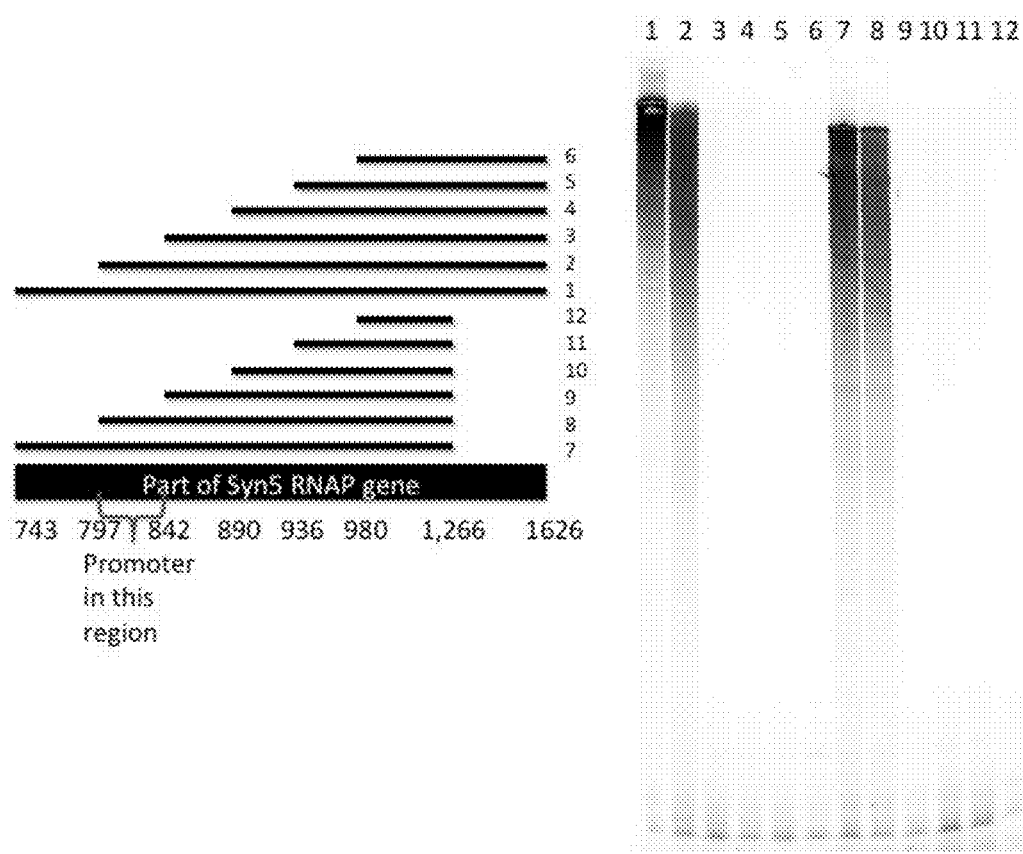

Using two sets of PCR fragments as transcription templates, the location of the Syn5 promoter was narrowed to the region between 760 and 1000 nt in the RNAP gene; templates lacking this region were not transcribed by the Syn5 RNAP (FIG. 13A). A similar strategy was used to further narrow the promoter to between 797 and 842 nt in the Syn5 RNAP gene (FIG. 13B). In order to precisely identify the 5' nucleotide of the promoter in this 46 nt region, every 10 nt (FIG. 2B) and then every 1 nt (FIG. 2C) were screened. DNA fragments are effective transcription templates for Syn5 RNAP as long as they contain the A highlighted in black background in FIG. 2C; thus this A is designated the 5' end of the Syn5 promoter. The 3' end of the promoter was determined using 3'-dNTPs as chain terminators (FIG. 3A). In this experiment, [α-³²P]CTP was used to replace either GTP, ATP, or UTP with their 3'-dNTP analog. 3'-dGTP blocked any transcription, suggesting that there is a G before the first C. 3'-dATP resulted in the production of a trinucleotide; thus the first three nucleotides are predicted to be pppGCA. A dinucleotide, presumably pppGC, is also present. 3'-dUTP resulted in the production of a 12 nt transcript (FIG. 3A). Combining these results the sequence of the Syn5 promoter was designated as 5'-ATTGGGCACCCGTAA-3' (SEQ ID NO:1) (sequence in blue background in FIG. 3). The Syn5 RNAP also produces significant amounts of abortive transcripts ranging from 2-11 nt together with the runoff product (FIG. 3A). These abortive transcripts are observed with all RNAPs and occur during the transition between the initiation and elongation of transcription (Cheetham et al.).

Syn5 RNAP does not recognize a T7 promoter, since it is unable to initiate transcription from a T7 DNA fragment containing the T7 Φ1.1 B promoter (FIG. 3B, lane c). In contrast, when the T7 promoter was replaced with the Syn5 promoter, Syn5 RNAP transcribed the template to produce a run-off product of the expected size (FIG. 3B, lane a). With T7 RNAP, the first nucleotide following the promoter is important in determining transcription efficiency (Milligan et al.). Syn5 RNAP is unable to incorporate UTP as the first ribonucleotide (FIG. 3B, lane b). At a T7 promoter, T7 RNAP initiates transcription and produces a runoff transcript (FIG. 3B, lane e). However, at a Syn5 promoter it does not initiate transcription but does catalyze some non-specific RNA synthesis (FIG. 3B, lane d).

On the Syn5 genome, there is only one other sequence identical to the Syn5 promoter sequence identified herein. The second sequence is located near the right end of Syn5 genome, after the terminase gene (FIG. 3C). Transcription on a PCR fragment covering this region confirms that this sequence is indeed an active promoter (FIG. 3C, lane 3). Several sequences within the Syn5 genome were identified by alignment to be similar to the promoter (up to 73% identity) but none of them served as effective Syn5 promoters in in vitro transcription reactions. Most T7-like phages have several strong promoters in the middle of their genomes to control the expression of their structural genes. However, Syn5 RNAP does not initiate specific transcription on a 6 kb fragment of the Syn5 genome encompassing the region from the end of the DNA metabolism genes through the end of the gene encoding the major capsid protein (FIG. 3C, lane 2).

Support was found for the presence of only two cyanophage promoters from previous bioinformatics analysis. Chen and Schneider extensively analyzed the promoter systems of T7-like phages (Chen et al. (2005)). For P-SSP7, the only cyanophage analyzed, no T7-like promoters were identified. However, when they aligned every 1 kb fragment of the P-SSP7 genome against the rest of the genome they found two identical sequences, 5'-AACCCC-TACGTATACA-3' (SEQ ID NO:6), one located within the RNAP gene and the other after the terminase gene (FIG. 3C). Although these two cyanophages infect different groups of host cyanobacteria, their similar distribution of promoters indicates a common transcription regulation mechanism among cyanophages, which differs from that found in other T7-like phage. In spite of this similarity, there is no obvious sequence similarity between the putative promoters from these two cyanophages.

Sequences of templates.

| PCR primers No. | Sequences (5'-3') | Forward (F) or reverse (R) | PCR products |
|---|---|---|---|
| 1 | GGAATTCCATATGTCCTTCGATCTCATCGCTCGCC (SEQ ID NO: 24) | F | DNA encoding Syn5 RNAP Template 1 in FIG. 2A and FIG. 3C |
| 2 | ACTGGCGGCCGCTCAGGAGAAGAAGTAAAGGGACTGGTTG (SEQ ID NO: 25) | R | DNA encoding Syn5 RNAP Template 1 in FIG. 2A and FIG. 3C |
| 3 | GGAATTCCATATGCATCACCATCACCATCACGGCGGAGGTGGAGGCTCCTTCGATCTCATCGCTCGCCAGCTTCAGCG (SEQ ID NO: 26) | F | DNA encoding His-tagged Syn5 RNAP |
| 4 | CTGCGGACGCACAGCCGCCCTGG (SEQ ID NO: 27) | F | Template 2 in FIG. 2A |
| 5 | GCCTTCTGGGACAAGCCCTTCACGG (SEQ ID NO: 28) | F | Template 3, 4 in FIG. 2A |
| 6 | ACTGGCGGCCGCCTAGGGTTTGAGCCATGATTCGGGGATG (SEQ ID NO: 29) | R | Template 2, 3 in FIG. 2A |
| 7 | CGATGCGGCCGCTCAGTAAGGATAATCAGCATCCCGACCATGGAGG (SEQ ID NO: 30) | R | Template 4 in FIG. 2A |
| 8 | GGAATTCCATATGCCTGCCTTCGATCTGGTCTGG (SEQ ID NO: 31) | F | Template 5 in FIG. 2A |
| 9 | ACTGGCGGCCGCTCATGTGTTGCGGTTGTATCGGATGGTG (SEQ ID NO: 32) | R | Template 5 in FIG. 2A |
| 10 | GGAATTCCATATGACGACTTCTGACGTTGCCCACC (SEQ ID NO: 33) | F | Template 6 in FIG. 2A |
| 11 | ACTGGCGGCCGCTTAGTGGCAATCCGCCCAGGAGTTACCTG (SEQ ID NO: 34) | R | Template 6 in FIG. 2A |
| 12 | CGATTCAGGTAAGCCCAAGATTG (SEQ ID NO: 35) | F | Template 7 in FIG. 2A |
| 13 | ACTGGCGGCCGCTCATTGCGGGGTAATAAGTATGGGTAC (SEQ ID NO: 36) | R | Template 7 in FIG. 2A |
| 14 | GGAATTCCATATGACCTTTGAGCCTCCCACCCTTC (SEQ ID NO: 37) | F | Template 8 in FIG. 2A |
| 15 | CCCAAGCTTTTACTCGGCGCAGGATGAACAGAATTGGTCG (SEQ ID NO: 38) | R | Template 8 in FIG. 2A |
| 16 | CCCGGTGAGGACTGTACAGAGGACC (SEQ ID NO: 39) | F | Template 1, 5 in FIG. 13A |
| 17 | GGGACTGACTTCGACAAGGCGCTCC (SEQ ID NO: 40) | F | Template 2, 6 in FIG. 13A |
| 18 | CCCTGGTGCTTCCTGGCTGCCTGCC (SEQ ID NO: 41) | F | Template 3, 7 in FIG. 13A |
| 19 | GCCTTCTGGGACAAGCCCTTCACGG (SEQ ID NO: 42) | F | Template 4, 8 in FIG. 13A |
| 20 | CACGGGGCCGGGGATGACCTCAGGG (SEQ ID NO: 43) | R | Template 1, 2, 3, 4 in FIG. 13A |
| 21 | GAGATGCTTGAGGGATGCTTGCGCC (SEQ ID NO: 44) | R | Template 5, 6, 7, 8 in FIG. 13A |
| 22 | ACCACAACGGTGGGTACCTGAGCG (SEQ ID NO: 45) | F | Template 1, 7 in FIG. 13B |
| 23 | GTAAAACGGGTCCATTGGGCACCCG (SEQ ID NO: 46) | F | Template 2, 8 in FIG. 13B |
| 24 | TTGCGATGCTCAACAACCTGCAGGG (SEQ ID NO: 47) | F | Template 3, 9 in FIG. 13B |

Sequences of templates.

| | | | |
|---|---|---|---|
| 25 | AGTTCTCGACATAGCGAACCACTGC<br>(SEQ ID NO: 48) | F | Template 4, 10 in FIG. 13B |
| 26 | GGCAAGTTCATACGCCACGCTCCCC<br>(SEQ ID NO: 49) | F | Template 5, 11 in FIG. 13B |
| 27 | CCCGGTGAGGACTGTACAGAGGACC<br>(SEQ ID NO: 50) | F | Template 6, 12 in FIG. 13B |
| 28 | GAGATGCTTGAGGGATGCTTGCGCC<br>(SEQ ID NO: 51) | R | Template 1, 2, 3, 4, 5, 6 in FIG. 13B |
| 29 | AGGATAGCCACCATTCGTTGACCGG<br>(SEQ ID NO: 52) | R | Template 7, 8, 9, 10, 11, 12 in FIG. 13B |
| 30 | CTCAGACCAGCCTGTATTACGCGC<br>(SEQ ID NO: 53) | F | Template 2 in FIG. 3C |
| 31 | GCGACTGCGTAACGCTCACCAGCG<br>(SEQ ID NO: 54) | R | Template 2 in FIG. 3C |
| 32 | GCCGGCACTCTTACTCATGACCCG<br>(SEQ ID NO: 55) | F | Template 3 in FIG. 3C |
| 33 | GGGTCGACTGGTGTCTCCCCTACG<br>(SEQ ID NO: 56) | R | Template 3 in FIG. 3C |

| DNA oligos No. | Sequences (5'-3') | Plus (P) or minis (M) strand | dsDNA fragments |
|---|---|---|---|
| 1 | GTAAAACGGGTCCATTGGGCACCCGTAAGCAAGGA<br>GACATACCCCTTGCGATGCTCAACAACCTGCAGGG<br>TCAGGCCTACAAGGTCAACCCTGAAGTTC<br>(SEQ ID NO: 57) | P | Template 1 in FIG. 2B |
| 2 | TCCATTGGGCACCCGTAAGCAAGGAGACATACCCC<br>TTGCGATGCTCAACAACCTGCAGGGTCAGGCCTAC<br>AAGGTCAACCCTGAAGTTC<br>(SEQ ID NO: 58) | P | Template 2 in FIG. 2B |
| 3 | ACCCGTAAGCAAGGAGACATACCCCTTGCGATGCT<br>CAACAACCTGCAGGGTCAGGCCTACAAGGTCAACC<br>CTGAAGTTC<br>(SEQ ID NO: 59) | P | Template 3 in FIG. 2B |
| 4 | AAGGAGACATACCCCTTGCGATGCTCAACAACCTG<br>CAGGGTCAGGCCTACAAGGTCAACCCTGAAGTTC<br>(SEQ ID NO: 60) | P | Template 4 in FIG. 2B |
| 5 | ACCCCTTGCGATGCTCAACAACCTGCAGGGTCAGG<br>CCTACAAGGTCAACCCTGAAGTTC<br>(SEQ ID NO: 61) | P | Template 5 in FIG. 2B |
| 6 | GAACTTCAGGGTTGACCTTGTAGGCCTGACCCTGC<br>AGGTTGTTGAGCATCGCAAGGGGTATGTCTCCTTG<br>CTTACGGGTGCCCAATGGACCCGTTTTAC<br>(SEQ ID NO: 62) | M | Template 1, 2, 3, 4, 5 in FIG. 2B |
| 7 | CCATTGGGCACCCGTAAGCAAGGAGACATACCCCT<br>TGCGATGCTCAACAACCT<br>(SEQ ID NO: 63) | P | Template 1 in FIG. 2C |
| 8 | CATTGGGCACCCGTAAGCAAGGAGACATACCCCTT<br>GCGATGCTCAACAACCT<br>(SEQ ID NO: 64) | P | Template 2 in FIG. 2C |
| 9 | ATTGGGCACCCGTAAGCAAGGAGACATACCCCTTG<br>CGATGCTCAACAACCT<br>(SEQ ID NO: 65) | P | Template 3 in FIG. 2C |
| 10 | TTGGGCACCCGTAAGCAAGGAGACATACCCCTTGC<br>GATGCTCAACAACCT<br>(SEQ ID NO: 66) | P | Template 4 in FIG. 2C |
| 11 | TGGGCACCCGTAAGCAAGGAGACATACCCCTTGCG<br>ATGCTCAACAACCT<br>(SEQ ID NO: 67) | P | Template 5 in FIG. 2C |
| 12 | GGGCACCCGTAAGCAAGGAGACATACCCCTTGCGA<br>TGCTCAACAACCT<br>(SEQ ID NO: 68) | P | Template 6 in FIG. 2C |
| 13 | GGCACCCGTAAGCAAGGAGACATACCCCTTGCGAT<br>GCTCAACAACCT<br>(SEQ ID NO: 69) | P | Template 7 in FIG. 2C |
| 14 | AGGTTGTTGAGCATCGCAAGGGGTATGTCTCCTTG<br>CTTACGGGTGCCCAATGGA<br>(SEQ ID NO: 70) | M | Template 1, 2, 3, 4, 5, 6, 7 in FIG. 3C |
| 15 | GGTATTGGGCACCCGTAAGGAGAACCTTAAGGTTT<br>AACTTTAAGACCCTTAAGTG<br>(SEQ ID NO: 71) | F | Template 1 in FIG. 3B |
| 16 | CACTTAAGGGTCTTAAAGTTAAACCTTAAGGTTCT<br>CCTTACGGGTGCCCAATACC<br>(SEQ ID NO: 72) | R | Template 1 in FIG. 3B |

-continued

Sequences of templates.

| 17 | GGTATTGGGCACCCGTAATGAGAACCTTAAGGTTT AACTTTAAGACCCTTAAGTG (SEQ ID NO: 73) | F | Template 2 in FIG. 3B |
|---|---|---|---|
| 18 | CACTTAAGGGTCTTAAAGTTAAACCTTAAGGTTCT CATTACGGGTGCCCAATACC (SEQ ID NO: 74) | R | Template 2 in FIG. 3B |
| 19 | GGTTAATACGACTCACTATAGGAGAACCTTAAGGT TTAACTTTAAGACCCTTAAGTG (SEQ ID NO: 75) | F | Template 3 in FIG. 3B |
| 20 | CACTTAAGGGTCTTAAAGTTAAACCTTAAGGTTCT CCTATAGTGAGTCGTATTAACC (SEQ ID NO: 76) | R | Template 3 in FIG. 3B |

Example IV

Characterization of Syn5 RNAP Transcription

Optimal Temperature and pH

The in vitro Syn5 transcription system was optimized using the purified RNAP and a plasmid containing a single Syn5 promoter. The optimum temperature for Syn5 RNAP is 24° C. (FIG. 4A). The activity decreases with lower temperatures but retains 15% of its maximum activity at 0° C. Only 8% of the maximum activity is observed at 37° C. and 2% at 42° C. In contrast, the maximum activity of T7 RNAP is observed at 37° C. and decreases dramatically below 20° C. (Chamberlin et al. (1973)). The lower temperature optimum for Syn5 RNAP probably reflects the temperature of the ocean environment of the host Synechococcus (Zwirglmaier et al.).

The pH of seawater is in the range of 7.5 to 8.4. The activity of Syn5 RNAP is highest at pH 8.0 and does not vary significantly in the range from pH 7.5 to 8.8 (FIG. 4B).

Salt and Metal Cofactors

T7 RNAP is highly sensitive to the ionic strength of the reaction (Chamberlin et al.; FIG. 5B). Since the environment of Syn5 is the ocean, it was tested whether it would be less sensitive to salt concentration. In fact, both NaCl and KCl significantly stimulate Syn5 RNAP activity. A two-fold increase is observed in the presence of 80 mM NaCl (FIG. 5A) and a three-fold stimulation in the presence of 160 mM KCl (FIG. 5B). The activity decreases above 160 mM KCl (FIG. 5B), with only 10% remaining at 300 mM (FIG. 5B). $MgCl_2$ is required as a cofactor for Syn5 RNAP activity, with a Km of about 2.5 mM in the presence of 160 mM KCl (FIG. 5C).

Other metal ions were tested in place of $Mg^{2+}$ as cofactors for the Syn5 RNAP using the filter-binding assay. At concentrations of 10 mM, $Ca^{2+}$, $Co^{2+}$, $Cu^{2+}$ or $Ni^{2+}$ cannot replace $Mg^{2+}$ in the Syn5 RNAP reaction. A small amount of activity is observed with 10 mM $Zn^{2+}$ or $Mn^{2+}$. Ferrous and manganese ions are of particular interests since they are abundant in cyanobacteria (Shcolnick et al.; Imashimizu et al.). Denaturing gels were used to characterize the products by Syn5 RNAP with ferrous as a cofactor (FIG. 6), since ferrous caused non-specific NTP precipitation in the filter-binding assay. $FeCl_2$ concentrations higher than 4 mM result in retardation of radioactive NTP in the gel and bands that are not distinguishable. 2 mM $FeCl_2$ clearly enabled the Syn5 RNAP to produce a 71 nt runoff transcript identical to that produced in the presence of $MgCl_2$ (FIG. 6, lane 4 versus lane 1). KCl stimulated the ferrous-catalyzed reaction (FIG. 6, lane 9 versus lane 10). Iron is the metal used at the active site of many important redox enzymes dealing with cellular respiration, oxidation and reduction in plants and animals. In addition, iron-sulphur clusters have been found in many nucleic acid processing enzymes including a RNAP (White et al.). However, iron as a cofactor in a polymerase reaction has not been reported. The efficiency of iron as a cofactor, however, is several times less than that of magnesium (FIG. 6, lane 9 versus lane 7). Furthermore, in the presence of iron, Syn5 RNAP did not produce longer transcripts (e.g. 225 nt, FIG. 6 lanes 11-15). Manganese, at lower concentration than that of magnesium, is also an active cofactor for Syn5 RNAP. The maximum yield of short runoff products synthesized by Syn5 RNAP was higher in the presence of manganese (0.25 to 1 mM) than that with magnesium (FIG. 6 lanes 16-20). Higher concentration of manganese inhibited the activity. It is noteworthy that the "N+1" runoff product was significantly higher with manganese than that with magnesium.

Nucleotides

The catalytic efficiencies were compared between Syn5 and T7 RNAPs at various ribonucleotide concentrations. For Syn5 RNAP, the apparent Km for GTP was 13.9±5.6 µM and the kcat was 2.5 $s^{-1}$ (FIG. 7A). Under the same conditions (except that KCl was omitted) the $Km_{GTP}$ for T7 RNAP was 45.8±9.0 µM and the kcat was 4.1 $s^{-1}$ (FIG. 7B). Although the maximal efficiency of T7 RNAP was higher than that of Syn5 RNAP, the latter showed greater activity with lower GTP concentrations. The kcat/$Km_{GTP}$ was higher for Syn5 RNAP (0.18) than for T7 RNAP (0.09). Similar results were obtained with UTP. The $Km_{GTP}$ for Syn5 RNAP was 7.4±1.5 µM and the $kcat_{GTP}$ was 2.8 $s^{-1}$ (FIG. 7C) while for T7 RNAP the $Km_{GTP}$ was 23.3±5.5 µM and the $kcat_{GTP}$ was 6.8 $s^{-1}$ (FIG. 7D). Syn5 RNAP consistently showed higher efficiency than T7 RNAP when comparing the kcat/$Km_{GTP}$ (0.38 versus 0.29). Without intending to be bound by scientific theory, the higher efficiency of ribonucleotides utilization at low concentration by Syn5 RNAP may benefit the cyanophage in the open ocean environment where nutrition is usually stringent.

Example V

Purification of Syn5 RNAP

The three-step purification of Syn5 RNAP from E. coli cells described above yielded active enzyme suitable for preliminary biochemical characterization and identification of its promoter (Zhu et al. (2013)). The purification procedure for Syn5 RNAP was modified and improved. The yield of protein was improved more than 10-fold by using an unusually high concentration of NaCl (2M) during chromatography (details see Materials and Methods). Additional benefits of this procedure were that the time required for purification is reduced 2-fold and the specific activity of the enzyme is increased 2-fold (FIG. 8). The Ni-NTA chromatography step alone in the presence of 2 M NaCl yielded apparently homogenous enzyme (FIG. 8A). The activity of the Syn5 RNAP by Ni-NTA and gel filtration chromatography was close to that of T7 RNAP (FIG. 8B). Hereafter Syn5 RNAP purified by this procedure was used in all experiments.

Example VI

Processivity of Syn5 RNAP

Figure 9F:
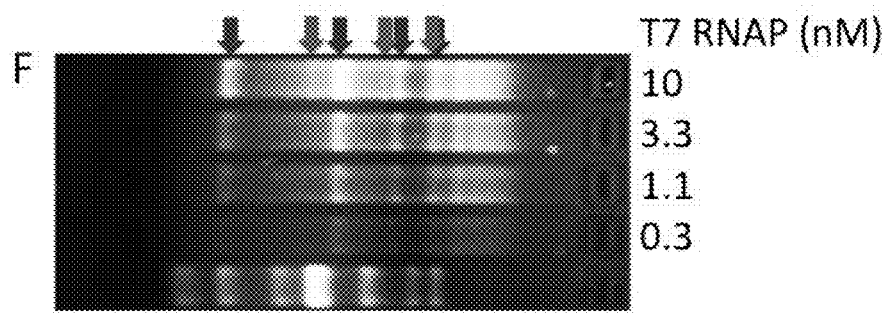
Figure 9G:
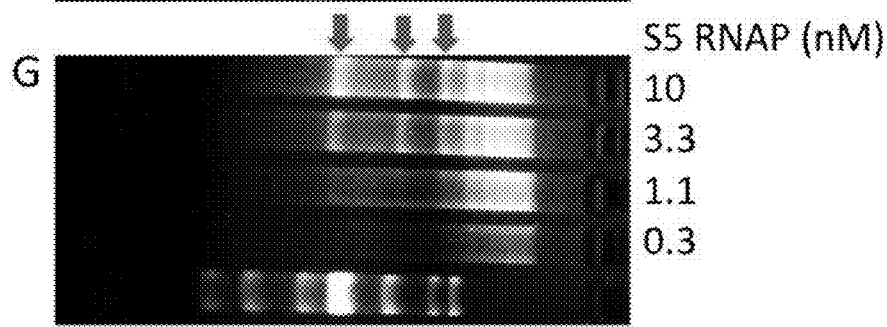

Syn5 RNAP has an apparently high processivity since only two promoters are present in the phage genome (Zhu et al. (2013)). To confirm this feature, plasmid templates were constructed containing a single promoter for Syn5 and T7 RNAPs, respectively. On such templates the RNAPs could perform rolling-circle synthesis to reach their maximum processivity. A gel assay was established to measure the processivity. Both Syn5 and T7 RNAP synthesize RNAs as shown on the gel. Syn5 RNAP shows activity similar to that of T7 RNAP (FIG. 9A). The product of the Syn5 RNAP reaction was confirmed to be RNA by DNase I and RNase I treatment (FIG. 9B). Addition of KCl increases the yield of transcripts of Syn5 RNAP (FIG. 9C), consistent with previous report (Zhu et al. (2013)). However, this stimulation was only observed when circular plasmids were used as templates (see following sections). The RNAP products were then separated under denaturing conditions. As shown in FIG. 9D, the longest products synthesized by both enzymes were longer than 9 kilo nt, with more products over 9 kilo nt produced by Syn5 RNAP. However, abortive products of specific patterns were observed. For Syn5 RNAP, the abortive products were of the size of multiple rounds of the plasmid, indicating that the clash of an elongating and initiating RNAP at the promoter region of the same plasmid is the cause of synthesis abortion. For T7 RNAP, two sets of abortive products were present, of which one was the same as above mentioned for Syn5 RNAP. Another set started from about 1000 nt, and then added multiple rounds of the plasmid length, indicating that a certain sequence in the plasmid terminated the T7 reaction, although a T7-terminator-like sequence could not be found in the plasmid. Both plasmids were then linearized to allow run-off transcription. As expected, both RNAPs synthesized a full-length run-off product of the plasmid size and T7 RNAP had an additional abortive product (FIG. 9E). To confirm the identity of the abortive products synthesized by Syn5 RNAP, various amount of enzyme were tested over same amount of templates. Without intending to be bound by scientific theory, if the assumption that the clash of multiple enzymes at the promoter was the basis for transcription abortion, then decreasing the amount of enzyme should result in less abortion of synthesis. Indeed, lowering the concentration of both enzymes reduced one set of abortive product (FIGS. 9F and 9G). However, another set of T7 products remained (FIG. 9F), confirming that these products were template dependent. The undesired termination presents one of the major withdraws of T7 RNAP in run-off transcription.

Figure 9H:
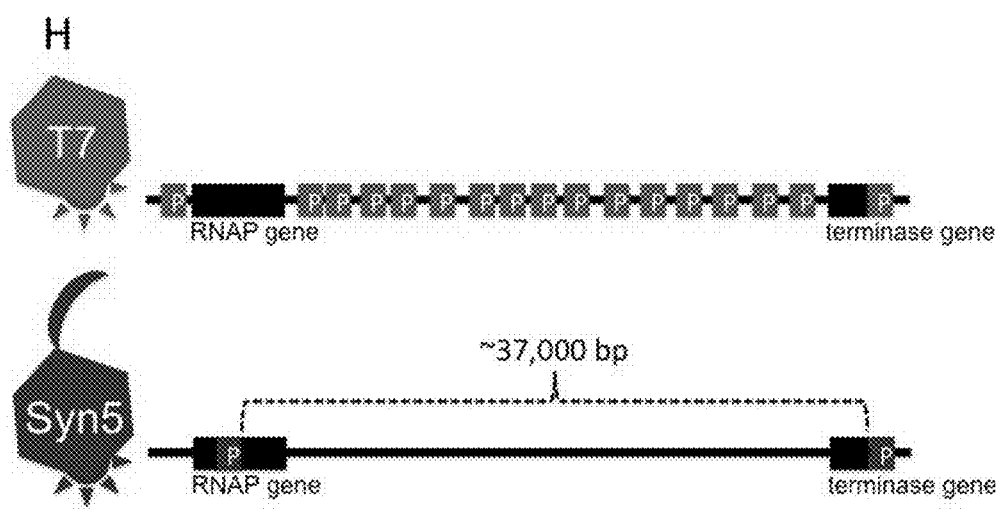

For Syn5 RNAP at low enzyme concentration, most products were over 9 kilo nt with some approaching 30 kilo nt (FIG. 9G). Without intending to be bound by scientific theory, the difference in processivity between the two RNAPs was consistent with the promoter distribution in the two phage genomes, Syn5 RNAP used one promoter to transcribe over 37 kilo nt while T7 required 15 promoters (FIG. 9H).

Example VII

Syn5 Versus T7 RNAP in Run-Off Transcription

Figure 10A:
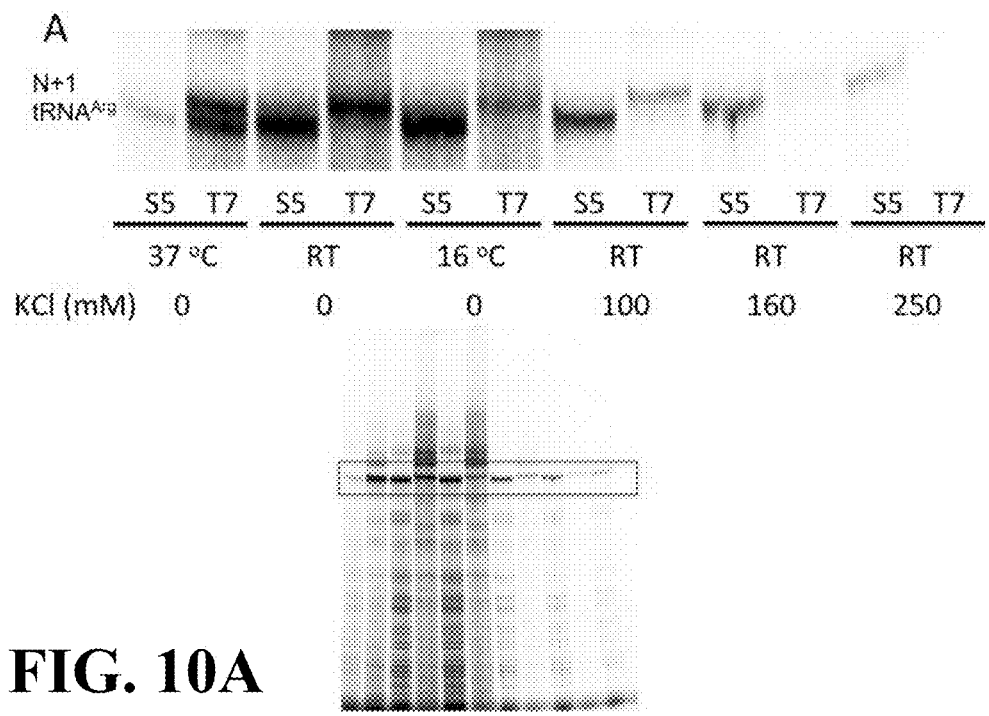
FIGS. 10A-10B depict a comparison of T7 and Syn5 RNA polymerase in run-off synthesis of small RNA. A) Effect of temperature and salt concentration on the RNA synthesis by T7 and Syn5 RNA polymerase. The region of precise product and the N+1 product was amplified from the whole gel as shown in the figure. B) Similar as A) except that His-tagged T7 RNA polymerase was used.
Figure 10B:
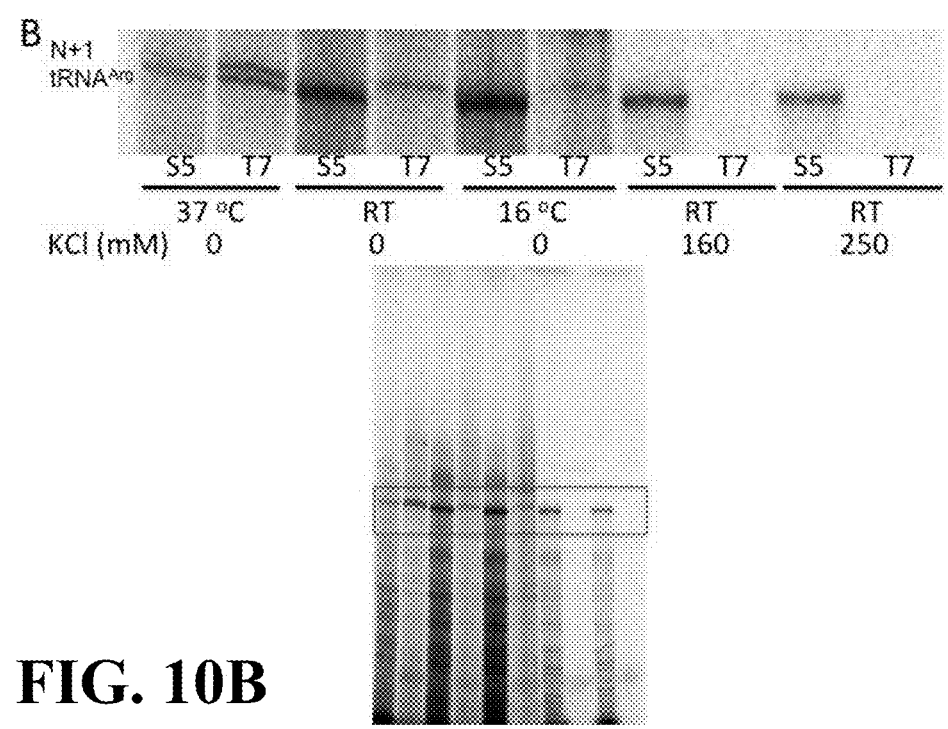

Parameters of Syn5 and T7 RNAP in run-off transcription were investigated using defined dsDNA templates. The DNA oligonucleotides contain the sequence encoding $E.\ coli$ tRNA$^{Arg}_{ACG}$ directly downstream of a Syn5 or T7 RNAP promoter so that the function of run-off products can be analyzed. Under all conditions examined, the Syn5 RNAP products did not contain detectable N+1 product band. On the other hand, the products obtained with T7 RNAP contained abundant amounts of the N+1 product (FIG. 10A). Syn5 RNAP also demonstrated much better activity over a range of temperatures and salt concentrations. Only at 37° C. did T7 RNAP have a higher yield of desired run-off product. T7 RNAP is known to be inhibited by high salt; little activity is seen with T7 RNAP at 160 mM KCl while even at 250 mM KCl Syn5 RNAP produces significant amounts of product. To exclude the possibility that the differences between the two RNAPs were a result of the His-tag on Syn5 RNAP, His-tagged T7 RNAP was prepared and the two enzymes were compared. Similar results were obtained confirming that the higher homogeneity of product 3'-end is an intrinsic property of Syn5 RNAP (FIG. 10B).

Example VIII

Synthesis of tRNA by Syn5 and T7 RNAP

In order to determine the effect of enzyme concentration on the homogeneity of the products, various amounts of both Syn5 and T7 RNAP were used to synthesize tRNA. A reaction temperature of 37° C. was used since T7 RNAP synthesizes more homogeneous products at this temperature. Under the same reaction condition except for the promoter sequences, at all concentrations of enzyme, Syn5 RNAP consistently produced more tRNA$^{Arg}$ with the absence of N+1 product. T7 RNAP, in contrast, produced more N+1 product than the desired product (FIG. 11A).

Figure 11B:
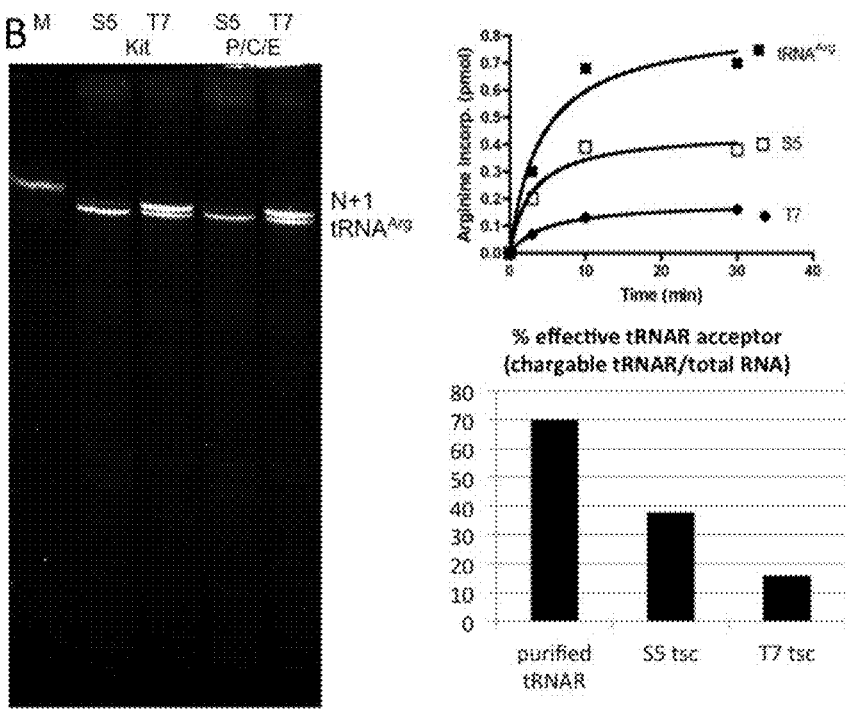

The ability of both enzymes to synthesize tRNA on a preparative scale was also compared. Under the same conditions described in Materials and Methods described herein, RNAs were recovered from a 200 □l Syn5 and T7 RNAP reaction using either a RNA Clean & Concentrator™-5 kit or by phenol chloroform extraction/ethanol precipitation. Analysis of both products on a sequencing gel again confirmed that the T7 products contain more than 50% N+1 products while the amount of Syn5 N+1 products are negligible (FIG. 11B). To confirm the identities of tRNA and N+1 products, tRNA function of the purified RNAs was measured in an aminoacylation assay. Only tRNAs with a precise 3'-end CCA can accept the cognate amino acid. Using an excess amount of $E.\ coli$ aminoacyl-tRNA synthetases and radioactive labeled arginine, it was determined that the amino acid charging activity of Syn5 RNAP products was much higher than that obtained from the T7 RNAP reaction. This result confirmed that the dominant specie of products from the Syn5 reaction was tRNA of precise length while that from the T7 RNAP reaction was contaminated with the N+1 product. Without a gel extraction step, the Syn5 products contained the desired tRNA (40%) while for T7 the desired product was much less (15%) (FIG. 11B). In practice, the N+1 product could not be removed by gel extraction due to the limited separation of products with one nucleotide difference on PAGE gel, especially when large amount of RNAs were loaded.

Example IX

Incorporation of Modified Nucleotides

Figure 12B:
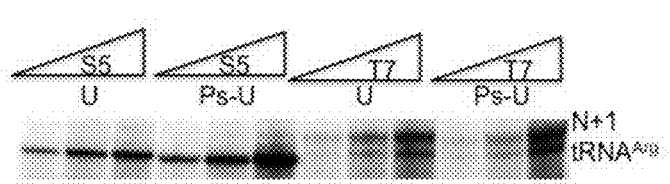

In some applications using RNAP, modified nucleotides are incorporated into run-off RNA transcripts to mimic functional RNA molecules or to improve the function of RNA. For instance, 5-methylcytidine (5mC) and pseudouridine (Ps-U) are introduced into mRNA to improve its function in vivo (Mandal et al.). The efficiency to incorporate 5mC and Ps-U into a 1500 nt run-off RNA transcript by Syn5 RNAP was examined. When CTP or UTP in the reaction was replaced by 5mCTP or Ps-UTP, respectively, the yield of RNA, based on $A_{260}$, was 0.76 □g and 0.63 □g, comparable to 0.69 □g when CTP and UTP are present (FIG. 12A). T7 RNAP incorporates 5mC and Ps-U at a similar efficiency with the yield of RNA being 0.64 □g, 0.75 □g, or 0.59 □g when normal C/UTP, 5mCTP or Ps-UTP was present, respectively. The yield of RNA by each RNAP at their optimal temperatures was identical (0.69 □g versus 0.64 □g, respectively). T7 RNAP was completely inhibited by 160 mM KCl while Syn5 RNAP still produced 0.31 □g RNA, about 50% the yield in the absence of salt (FIG. 12A). The efficiency of incorporation of Ps-U into small RNA transcripts by both RNAPs was also investigated. Using radioactively labeled CTP, the yield of $tRNA^{Arg}$ was higher for both RNAPs when UTP was replaced by Ps-UTP, while T7 RNAP again produced predominantly N+1 products (FIG. 12B).

Example X

Synthesis and Activity of Modified Syn5 RNAP

Materials
5× Transcription Buffer
200 mM Tris-HCl, pH 8.0
10 mM spermidine
100 mM DTT
100 mM $MgCl_2$
Enzyme Dilution Buffer
50 mM Tris-HCl pH 8.0
100 mM NaCl
20 mM β-ME
1 mM EDTA
50% glycerol
0.1% Triton® X-100
80 mM each NTP, pH 8.0
Inorganic Pyrophosphatase
RNase inhibitor
Template
Transcription templates could be synthetic DNA, PCR products, or linearized vectors with the (SEQ ID NO: 77)
5'-GCC<u>ATTGGGCACCCGTAA</u>-3' promoter sequence attached at the 5' end. Synthetic templates purified by urea-PAGE were desired.
Syn5 RNA Polymerase
Working solution was (10-100 □M) in enzyme dilution buffer.

Preparation of Syn5 RNA Polymerase

Figure 16:
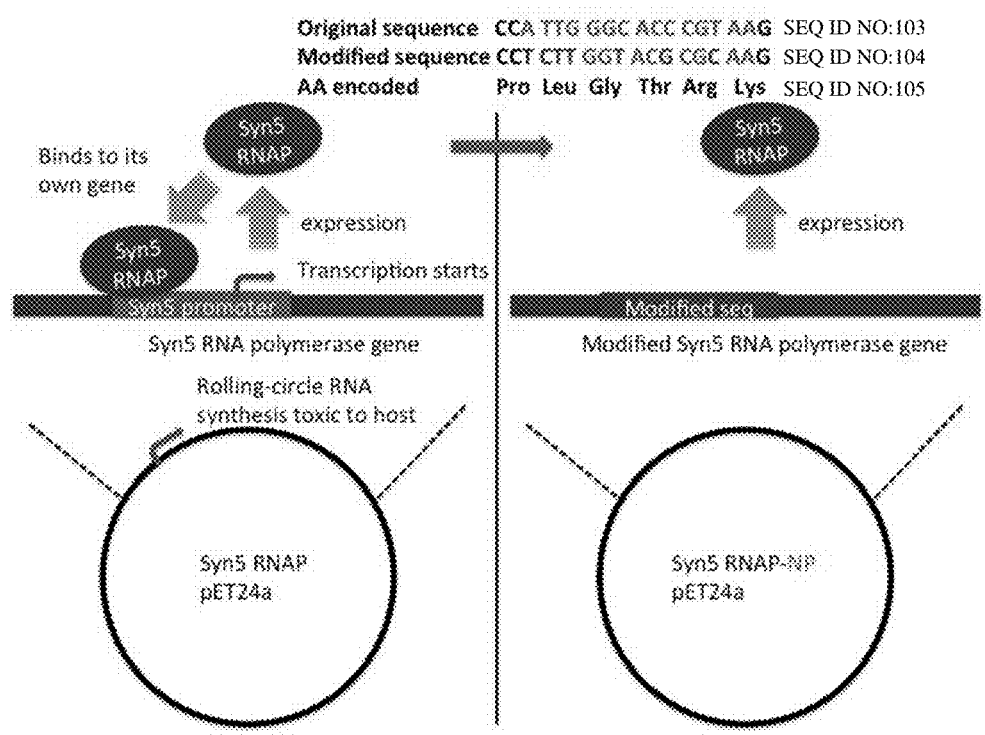
FIG. 16 schematically depicts the construction of vectors expressing wild-type Syn5 RNAP and Syn5 RNAP having a modified promoter region (Syn5 RNAP-NP). The original nucleotide sequence is set forth as SEQ ID NO:78. The modified nucleotide sequence is set forth as SEQ ID NO:80. The amino acid sequence encoded is set forth as SEQ ID NO:79.
Figure 17:
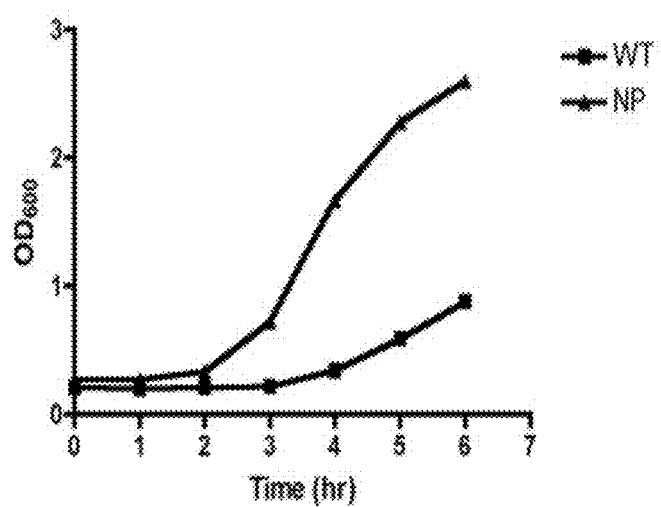
FIG. 17 graphically depicts a growth curve of E. coli BL21 (DE3) expressing Syn5 RNA polymerase from wild-type (WT, Syn5 RNAP-pET24a) or modified (Syn5 RNAP-NP-pET24a) vector. The graph illustrates that a vector expressing Syn5 RNAP-NP was less toxic to host cells than a vector expressing wild-type Syn5 RNAP.
Figure 18:
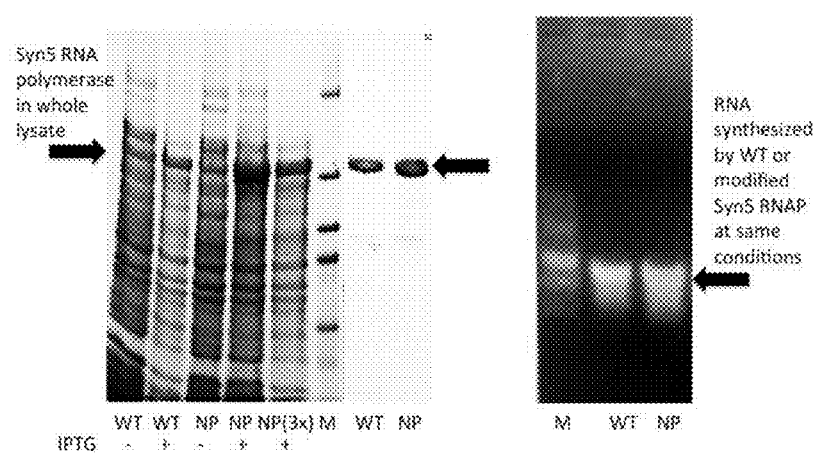
FIG. 18 depicts gels showing expression and activity of Syn5 RNAP-NP. Modified (Syn5 RNAP-NP-pET24a) vector produced more Syn5 RNAP than wild-type (WT, Syn5 RNAP-pET24a) vector, while maintaining comparable enzymatic activity.

The wild-type Syn5 RNA polymerase gene was modified as follows to improve expression in *E. coli* cells. Nucleotides in Syn5 RNA polymerase gene (No. 808-825) CCA TTG GGC ACC CGT AAG (SEQ ID NO:78) encoding Pro Leu Gly Thr Arg Lys (SEQ ID NO:79) were mutated to CCT CTT GGT ACG CGC AAG (SEQ ID NO:80) without changing the amino acids encoded, and the Syn5 promoter A TTG GGC ACC CGT AA (SEQ ID NO:81) within this region was removed (FIG. 16). Thus, when expressed in *E. coli*, the enzyme produced by the modified gene would not start transcription from its own gene, enabling the cells to grow much faster (FIG. 17) and yield at least 5 times more enzyme than cells expressing wild-type Syn5 RNAP. The protein produced from the modified gene had same amino acids constitution and exhibited the same enzymatic activity as the wild-type Syn5 RNAP (FIG. 18). The modified gene was designated as Syn5 RNAP-NP (SEQ ID NO:83, shown in FIG. 22).

*E. coli* BL21(DE3) was transformed with plasmid Syn5 RNAP-NP-pET24 encoding an N-terminal His-tagged Syn5 RNA polymerase. Cells were grown at 37° C. until they reached an OD of 1.2, at which point the temperature was reduced to 25° C. and IPTG was added at final concentration of 0.5 mM. Cells were grown an additional 4 hours before collection. The purification procedure used is described in "Zhu B, Tabor S, Richardson CC. (2014) Syn5 RNA polymerase synthesizes precise run-off RNA products. Nucleic Acids Res [Epub ahead of print]" by Ni-NTA and gel filtration in the presence of 2 M NaCl. From 2 L cells, 40 mg Syn5 RNA polymerase was produced (as 1 mM stock solution).

Importantly, the modified Syn5 RNAP described in this example provided higher expression than the wild-type Syn5 RNAP. The modified Syn5 RNAP described in this example also provides decreased toxicity to host cells. Accordingly, modified Syn5 RNAP proteins provide commercial advantages over wild-type Syn5 RNAP proteins.

Example XI

High Range ssRNA Ladder

Syn5 RNA polymerase had an apparent processivity over 30-kilo nucleotides. A circular plasmid containing a Syn5 promoter was used as a transcription template in the presence of excess Syn5 RNAP relative to template for rolling-circle RNA synthesis. Collision of multiple RNAPs at the promoter generated an RNA ladder of length equal to multiple rounds of the plasmid. For example when pUC19 (2.7 k nt) was used as a template, the product was a ladder of 2.7*n (n=1, 2, 3, 4, 5, 6, 7, 8 . . . )k nucleotides.

For a 10 □l reaction:

| | |
|---|---|
| 5X transcription Buffer | 2 □l |
| 80 mM NTP | 0.5 □l (final concentration 4 mM)* |
| 250 nM plasmid S5P-pUC19 | 4 □l (final concentration 100 nM) |
| 40 U/□l RNaseOUT RNase inhibitor | 0.4 □l |
| 1 U/□L Inorganic Pyrophosphatase | 0.2 □l |
| 10 □M Syn5 RNA Polymerase | 1 □l (final concentration 1 □M) * |
| 1.6M KCl# | 1 □l |
| RNase free $H_2O$ | 0.9 □l |

The reaction was incubated at room temperature for 4 hours. The reaction was diluted 2-fold with $H_2O$, and 1 U DNase I was added. This was incubated at 37° C. for 30 minutes. RNA was then purified using a spinning kit. Into 50

Figure 19:
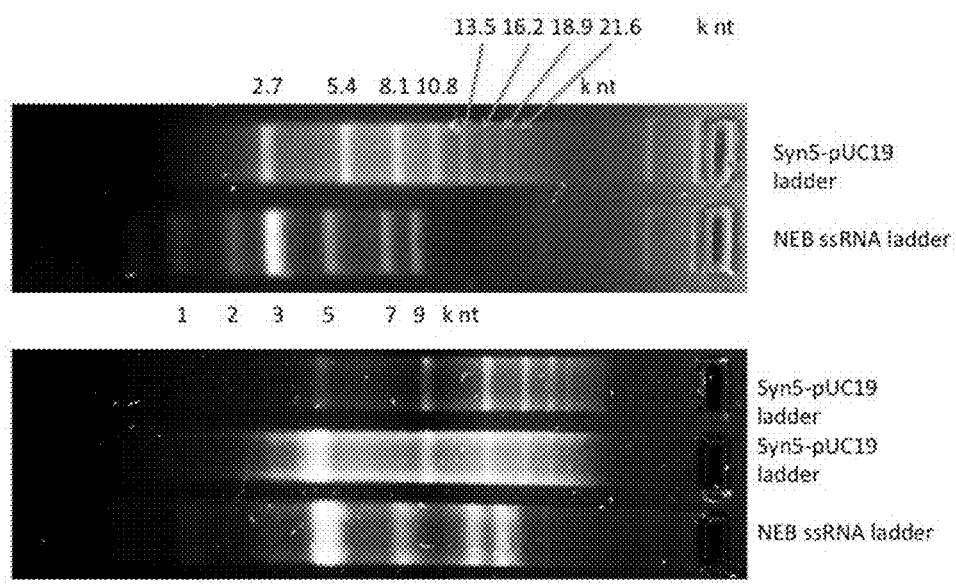
FIG. 19 depicts gels showing an S5 RNAP-pUC19 RNA ladder. The high range ladder was generated using Syn5 RNAP-pUC19 in a single reaction.

□l H₂O (~1 □g/□l), 2-5 □l of the reaction was mixed with denaturing dye, incubated at 70° C. for 3 minutes, and loaded onto a 1.6% TAE-agarose gel (FIG. 19).

Importantly, large RNA markers (e.g., greater than 10,000 nucleotides in length) were generated. These markers are much longer than commercially available markers. Large markers such as those described herein are unprecedented and will provide significant cost savings over markers known by others in the art.

Changing the NTP and/or RNAP concentrations could alter the relative intensity of bands. Using 160 mM KCl increased the yield only when a circular plasmid was used as the template.

Example XII

Synthesis of Human Mt tRNA$_{Pro}$—Short RNA

Oligos from IDT (100 Nmole Scale)

[S5PhmttRNAProUGGF.xdna]-89 bp
GCCATTGGGCACCCGTAACAGAGAATAGTTTAAATTAGAATCTTAGCTTT

GGGTGCTAATGGTGGAGTTAAAGACTTTTTCTCTGACCA

[S5PhmttRNAProUGGR.xdna]-89 bp
TGGTCAGAGAAAAAGTCTTTAACTCCACCATTAGCACCCAAAGCTAAGAT

TCTAATTTAAACTATTCTCTGTTACGGGTGCCCAATGGC

Dissolved in nuclease free water to make 200 □M solution, purify with Urea-PAGE gel extraction (omit gel purification results in 50% lower yield).
Annealing Reaction:

| Tris-HCl pH 7.5 | final 10 mM |
| NaCl | final 50 mM |
| S5PhmttRNAProUGGF | final 40 □M |
| S5PhmttRNAProUGGR | final 40 □M |

The annealing reaction was placed in a heating block at 90° C. The heating block was then turned off and allowed to slowly cool down to room temperature. A pilot assay (using 10-20 □l) is recommended for determining the best ratio of template/enzyme to use in various situations.

For a 100 □l reaction:

| 5X transcription Buffer | 20 □l |
| 80 mM NTP | 10 □l (final concentration 8 mM)# |
| 40 □M dsDNA template | 10 □l (final concentration 4 □M) |
| 40 U/□l RNaseOUT RNase inhibitor | 10 □l |
| 1 U/□L Inorganic Pyrophosphatase | 2 □l |
| 50 □M Syn5 RNA Polymerase | 10 □l (final concentration 5 □M)@ |
| 30% PVP-40 | 10 □l |
| RNase free H₂O | 28 □l |

Figure 20:
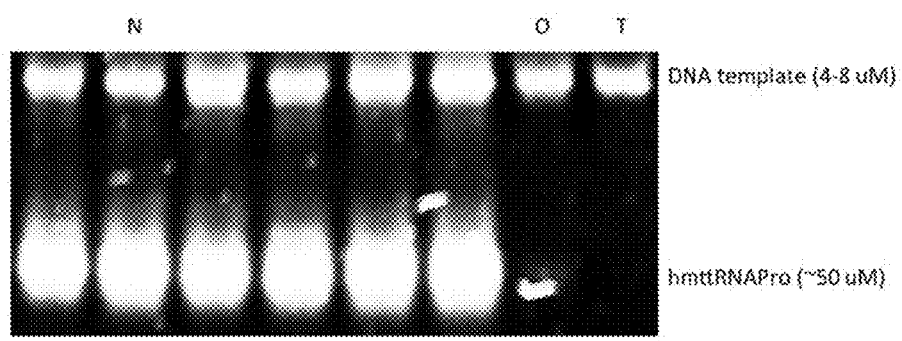
FIG. 20 depicts a gel showing that Syn5 RNAP synthesizes precise run-off RNA products. N, transcription reaction performed using optimized conditions. O, transcription reaction performed using art-known conditions. T, DNA template marker.

The reaction was incubated at 37° C. for 4 hours. 0.2 □l of the reaction was loaded on a 10% TBE native gel. The gel was run until the bromphenol blue reached the bottom. The gel was stained with ethidium bromide (FIG. 20).

Under these conditions, 37° C. gave better yield for short RNAs, however it impeded the processivity of the enzyme. For RNAs longer than 3,000 nucleotides, incubation should be performed at room temperature. Temperatures higher than 37° C. should be avoided—at 42° C. enzyme activity was very low. A final NTP concentration of 4 mM also gave a good yield (approximately 20% less). A final concentration over 5 □M for Syn5 RNAP in the reaction resulted in severe protein precipitation. Slight precipitation observed at concentrations of 5 □M or lower did not impede results.

Optional DNase I Treatment

DNase I was inhibited by 8 mM (but not 4 mM) NTP. If used, the DNase I was diluted with an equal volume of water prior to its addition to the reaction.

Figure 21:
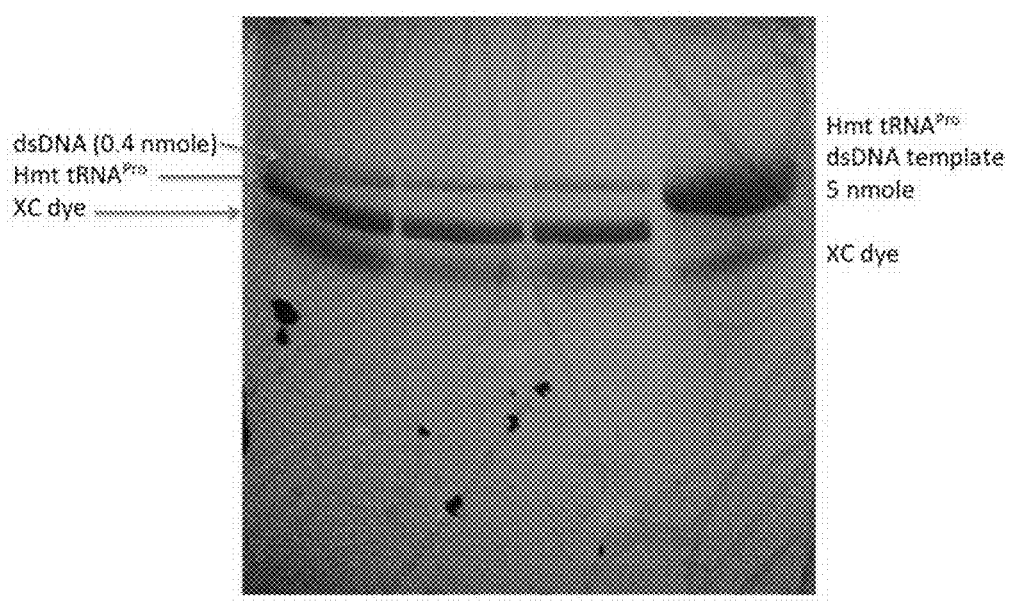
FIG. 21 depicts a 10% TBE-7M urea gel. Each 100 □l Syn5 transcription reaction produced an estimated yield of 4 nmole/100 □l. A 11×6.5×0.1 inch gel was used and run at 400 V. The bromphenol blue was run to the bottom, and the gel was visualized under UV light.

Gel extraction (FIG. 21) could be used to facilely separate DNA and tRNA. In a 100 □l transcription reaction, the tRNA was recovered and the DNA template could be recycled and used in additional transcription reactions.

An optimized condition for short RNA production was used based on methods described in in Zhu et al. ((2014) Syn5 RNA polymerase synthesizes precise run-off RNA products. Nucleic Acids Res [Epub ahead of print]).

Example XIII ssRNA Ladder Production by RNA Polymerases

According to certain aspects of the invention, a ssRNA ladder is generated using rolling circle-based transcription, using any single-subunit RNA polymerase known in the art (e.g., Syn5, T7, T3, SP6 and the like) coupled with its promoter and/or terminator present in a circular plasmid of desired size.

Figure 23:
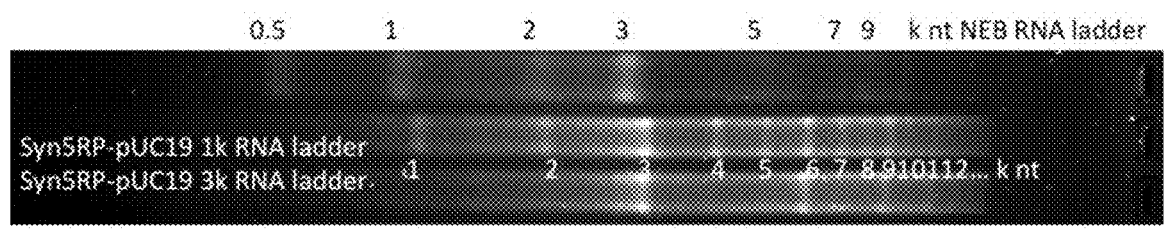
FIG. 23 depicts a gel showing that multiple Syn5 promoters placed in pUC19 yielded a 1 kb RNA ladder.

For example, in contrast to the results presented in Example XI, by inserting multiple Syn5 promoters in plasmid pUC19, a 1 kb RNA ladder pattern could be achieved using Syn5 RNAP (FIG. 23).

Example XIV

References

The references below are hereby incorporated by reference herein in their entireties. These references may be referred to throughout the specification by author and date.

Suttle, C. A. (2005) Viruses in the sea. Nature, 437, 356-361.
Suttle, C. A. (2007) Marine viruses—major players in the global ecosystem. Nat. Rev. Microbio., 5, 801-812.
Lindell, D., Jaffe, J. D., Johnson, Z. I., Church, G. M. and Chisholm, S. W. (2005) Photosynthesis genes in marine viruses yield proteins during host infection. Nature, 438, 86-89.
Lindell, D., Jaffe, J. D., Coleman, M. L., Futschik, M. E., Axmann, I. M., Rector, T., Kettler, G., Sullivan, M. B., Steen, R., Hess, W. R. et al. (2007) Genome-wide expression dynamics of a marine virus and host reveal features of co-evolution. Nature, 449, 83-86.
Chen, F. and Lu, J. (2002) Genomic sequence and evolution of marine cyanophage P60: a new insight on lytic and lysogenic phages. Appl. Environ. Microbiol., 68, 2589-2594.
Liu, X., Kong, S., Shi, M., Fu, L., Gao, Y. and An, C. (2008) Genomic analysis of freshwater cyanophage Pf-WMP3 Infecting cyanobacterium Phormidium foveolarum: the conserved elements for a phage. Microbial Ecol., 56, 671-680.
Mann, N. H., Clokie, M. R., Millard, A., Cook, A., Wilson, W. H., Wheatley, P. J., Letarov, A. and Krisch, H. M. (2005) The genome of S-PM2, a "photosynthetic" T4-type bacteriophage that infects marine Synechococcus strains. J. Bacteriol., 187, 3188-3200.
Liu, X., Shi, M., Kong, S., Gao, Y. and An, C. (2007) Cyanophage Pf-WMP4, a T7-like phage infecting the freshwater cyanobacterium *Phormidium foveolarum*: complete genome sequence and DNA translocation. *Virology*, 366, 28-39.

Millard, A. D., Zwirglmaier, K., Downey, M. J., Mann, N. H. and Scanlan, D. J. (2009) Comparative genomics of marine cyanomyoviruses reveals the widespread occurrence of *Synechococcus* host genes localized to a hyperplastic region: implications for mechanisms of cyanophage evolution. *Environ. Microbiol.* 11, 2370-2387.

Sullivan, M. B., Coleman, M. L., Weigele, P., Rohwer, F. and Chisholm, S. W. (2005) Three *Prochlorococcus* cyanophage genomes: signature features and ecological interpretations. *PLoS Biol.*, 3, e144.

Sullivan, M. B., Krastins, B., Hughes, J. L., Kelly, L., Chase, M., Sarracino, D. and Chisholm, S. W. (2009) The genome and structural proteome of an ocean siphovirus: a new window into the cyanobacterial 'mobilome'. *Environ. Microbiol.*, 11, 2935-2951.

Weigele, P. R., Pope, W. H., Pedulla, M. L., Houtz, J. M., Smith, A. L., Conway, J. F., King, J., Hatfull, G. F., Lawrence, J. G. and Hendrix, R. W. (2007) Genomic and structural analysis of Syn9, a cyanophage infecting marine *Prochlorococcus* and *Synechococcus*. *Environ. Microbiol.*, 9, 1675-1695.

Pope, W. H., Weigele, P. R., Chang, J., Pedulla, M. L., Ford, M. E., Houtz, J. M., Jiang, W., Chiu, W., Hatfull, G. F., Hendrix, R. W. and King, J. (2007) Genome sequence, structural proteins, and capsid organization of the cyanophage Syn5: a "horned" bacteriophage of marine *synechococcus*. *J. Mol. Biol.*, 368, 966-981.

Lindell, D., Sullivan, M. B., Johnson, Z. I., Tolonen, A. C., Rohwer, F. and Chisholm, S. W. (2004) Transfer of photosynthesis genes to and from *Prochlorococcus* viruses. *Proc. Natl. Acad. Sci. USA.*, 101, 11013-11018.

Sharon, I., Alperovitch, A., Rohwer, F., Haynes, M., Glaser, F., Atamna-Ismaeel, N., Pinter, R. Y., Partensky, F., Koonin, E. V., Wolf, Y. I. et al. (2009) Photosystem I gene cassettes are present in marine virus genomes. *Nature*, 461, 258-262.

Sabehi, G., Shaulov, L., Silver, D. H., Yanai, I., Harel, A. and Lindell, D. (2012) A novel lineage of myoviruses infecting cyanobacteria is widespread in the oceans. *Proc. Natl. Acad. Sci. USA.*, 109, 2037-2042.

Raytcheva, D. A., Haase-Pettingell, C., Piret, J. M. and King, J. A. (2011) Intracellular assembly of cyanophage Syn5 proceeds through a scaffold-containing procapsid. *J. Virol.*, 85, 2406-2415.

Gao, E. B., Gui, J. F. and Zhang, Q. Y. (2012) A novel cyanophage with a cyanobacterial nonbleaching protein A gene in the genome. *J. Virol.*, 86, 236-245.

Thompson, L. R., Zeng, Q., Kelly, L., Huang, K. H., Singer, A. U., Stubbe, J. and Chisholm, S. W. (2011) Phage auxiliary metabolic genes and the redirection of cyanobacterial host carbon metabolism. *Proc. Natl. Acad. Sci. USA.*, 108, E757-764.

Waterbury, J. B. and Valois, F. W. (1993) Resistance to co-occurring phages enables marine *synechococcus* communities to coexist with cyanophages abundant in seawater. *Appl. Environ. Microbiol.*, 59, 3393-3399.

Sullivan, M. B., Waterbury, J. B. and Chisholm, S. W. (2003) Cyanophages infecting the oceanic cyanobacterium *Prochlorococcus*. *Nature*, 424, 1047-1051.

Zwirglmaier, K., Jardillier, L., Ostrowski, M., Mazard, S., Garczarek, L., Vaulot, D., Not, F., Massana, R., Ulloa, O. and Scanlan, D. J. (2008) Global phylogeography of marine *Synechococcus* and *Prochlorococcus* reveals a distinct partitioning of lineages among oceanic biomes. *Environ. Microbiol.*, 10, 147-161.

Cheetham, G. M. and Steitz, T. A. (2000) Insights into transcription: structure and function of single-subunit DNA-dependent RNA polymerases. *Curr. Opin Struct. Biol.*, 10, 117-123.

Davanloo, P., Rosenberg, A. H., Dunn, J. J. and Studier, F. W. (1984) Cloning and expression of the gene for bacteriophage T7 RNA polymerase. *Proc. Natl. Acad. Sci. USA.*, 81, 2035-2039.

Chen, Z. and Schneider, T. D. (2005) Information theory based T7-like promoter models: classification of bacteriophages and differential evolution of promoters and their polymerases. *Nucleic Acids Res.*, 33, 6172-6187.

Dunn, J. J. and Studier, F. W. (1983) Complete nucleotide sequence of bacteriophage T7 DNA and the locations of T7 genetic elements. *J. Mol. Biol.*, 166, 477-535.

Milligan, J. F., Groebe, D. R., Witherell, G. W. and Uhlenbeck, O. C. (1987) Oligoribonucleotide synthesis using T7 RNA polymerase and synthetic DNA templates. *Nucleic Acids Res.*, 15, 8783-8798.

Chamberlin, M. and Ring, J. (1973) Characterization of T7-specific ribonucleic acid polymerase. II. Inhibitors of the enzyme and their application to the study of the enzymatic reaction. *J. Biol. Chem.*, 248, 2245-2250.

Shcolnick, S. and Keren, N. (2006) Metal homeostasis in cyanobacteria and chloroplasts. Balancing benefits and risks to the photosynthetic apparatus. *Plant Physiol.*, 141, 805-810.

Imashimizu, M., Tanaka, K. and Shimamoto, N. (2011) Comparative Study of Cyanobacterial and *E. coli* RNA Polymerases: Misincorporation, Abortive Transcription, and Dependence on Divalent Cations. *Genet. Res. Int.*, 2011, 572689.

White, M. F. and Dillingham, M. S. (2012) Iron-sulphur clusters in nucleic acid processing enzymes. *Curr. Opin Struct. Biol.*, 22, 94-100.

Chamberlin, M. J. and Ryan, T. (1982) Bacteriophage DNA-dependent RNA polymerases. In Boyer, P. D. (ed.), *The Enzymes*. Academic Press, New York, Vol. 15B, pp. 87-109.

Tabor, S. and Richardson, C. C. (1985) A bacteriophage T7 RNA polymerase/promoter system for controlled exclusive expression of specific genes. Proc. Natl. Acad. Sci. USA, 82, 1074-1078.

Milligan, J. F., Groebe, D. R., Witherell, G. W. and Uhlenbeck, O. C. (1987) Oligoribonucleotide synthesis using T7 RNA polymerase and synthetic DNA templates. *Nucleic Acids Res.*, 15, 8783-8798.

Milligan, J. F. and Uhlenbeck, O. C. (1989) Synthesis of small RNAs using T7 RNA polymerase. *Methods Enzymol.*, 180, 51-62.

Melton, D. A., Krieg, P. A., Rebagliati, M. R., Maniatis, T., Zinn, K. and Green, M. R. (1984) Efficient in vitro synthesis of biologically active RNA and RNA hybridization probes from plasmids containing a bacteriophage SP6 promoter. *Nucleic Acids Res.*, 12, 7035-7056.

Krieg, P. A. and Melton, D. A. (1987) In vitro RNA synthesis with SP6 RNA polymerase. *Methods Enzymol.*, 155, 397-415.

Morris, C. E., Klement, J. F. and McAllister, W. T. (1986) Cloning and expression of the bacteriophage T3 RNA polymerase gene. *Gene*, 41, 193-200.

Chamberlin, M. and Ring, J. (1973) Characterization of T7-specific ribonucleic acid polymerase. II. Inhibitors of the enzyme and their application to the study of the enzymatic reaction. *J. Biol. Chem.*, 248, 2245-2250.

Lyakhov, D. L., He, B., Zhang, X., Studier, F. W., Dunn, J. J. and McAllister, W. T. (1998) Pausing and termination by bacteriophage T7 RNA polymerase. *J. Mol. Biol.*, 280, 201-113.

Krupp, G. (1988) RNA synthesis: strategies for the use of bacteriophage RNA polymerases. *Gene*, 72, 75-89.

Moran, S., Ren, R. X., Sheils, C. J., Rumney, S. 4$^{th}$ and Kool, E. T. (1996) Non-hydrogen bonding 'terminator' nucleotides increase the 3'-end homogeneity of enzymatic RNA and DNA synthesis. *Nucleic Acids Res.*, 24, 2044-2052.

Kao, C., Zheng, M. and Rüdisser, S. (1999) A simple and efficient method to reduce nontemplated nucleotide addition at the 3 terminus of RNAs transcribed by T7 RNA polymerase. *RNA*, 5, 1268-1272.

Schürer, H., Lang, K., Schuster, J. and Mörl, M. (2002) A universal method to produce in vitro transcripts with homogeneous 3' ends. *Nucleic Acids Res.*, 30, e56.

Wichlacz, A., Legiewicz, M. and Ciesiolka, J. (2004) Generating in vitro transcripts with homogenous 3' ends using trans-acting antigenomic delta ribozyme. *Nucleic Acids Res.*, 32, e39.

Salvail-Lacoste, A., Di Tomasso, G., Piette, B. L. and Legault, P. (2013) Affinity purification of T7 RNA transcripts with homogeneous ends using ARiBo and CRISPR tags. *RNA*, 19, 1003-1014.

Zhu, B., Tabor, S., Raytcheva, D. A., Hernandez, A., King, J. A., Richardson, C. C. (2013) The RNA polymerase of marine cyanophage Syn5. *J. Biol. Chem.*, 288, 3545-3552.

Zhu, B., Lee, S. J., Tan, M., Wang, E. D. and Richardson, C. C. (2012) Gene 5.5 protein of bacteriophage T7 in complex with *Escherichia coli* nucleoid protein H-NS and transfer RNA masks transfer RNA priming in T7 DNA replication. *Proc. Natl. Acad. Sci. USA*, 109, 8050-8055.

Tan, M., Zhu, B., Zhou, X. L., He, R., Chen, X., Eriani, G. and Wang, E. D. (2010) tRNA-dependent pre-transfer editing by prokaryotic leucyl-tRNA synthetase. *J. Biol. Chem.*, 285, 3235-3244.

Mandal, P. K. and Rossi, D. J. (2013) Reprogramming human fibroblasts to pluripotency using modified mRNA. *Nat. Protoc.*, 8, 568-582.

Example XV

Incorporation of 2'-Modified dNTPs by Syn5 RNA Polymerase

According to certain aspects of the invention, methods are presented wherein 2'-modified-dNTPs are incorporated into RNA using Syn5 RNA polymerase. According to one aspect, the 2'-modified dNTP is 2'-fluoro-dNTP. According to one aspect, the 2'-modified dNTP is 2'-F-dCMP and 2'-F-dUMP. According to one aspect, the replacement of rCMP and rUMP by 2'-F-dCMP and 2'-F-dUMP in RNA improves resistance of RNA to RNase A (the most common RNase contaminant) and greatly improves the stability of RNA, which is a major issue for RNA research and applications. T7 RNA polymerase Y639F mutant is a commercially available polymerase to incorporate 2'-F-RNA into RNA available from Epicentre as T7 R & DNA™ Polymerase and The DuraScribe® T7 Transcription Kit. See Sousa et al., *EMBO J.* 14: 4609-4621 (1995) and U.S. Pat. No. 5,849, 546. One of skill will be able to readily envision other 2'-modified nucleoside triphosphates such as 2'-NH$_2$-dNTP and 2'-OMe-dNTP.

Example XVI

Materials and Methods for Incorporation of 2'-Modified dNTPs by Syn5 RNA Polymerase According to certain aspects of the invention, the following materials and methods are described for incorporation of 2'-modified dNTPs by Syn5 RNA polymerase into RNA.

Materials

5× Mg Buffer:
200 mM Tris-HCl, pH 8.0
10 mM spermidine
100 mM DTT
100 mM MgCl$_2$ (final 20 mM)

5×Mg/Mn Buffer:
200 mM Tris-HCl, pH 8.0
10 mM spermidine
100 mM DTT
50 mM MgCl$_2$ (final 10 mM)
25 mM MnCl$_2$ (final 5 mM)

Enzyme Dilution Buffer:
50 mM Tris-HCl pH 8.0
100 mM NaCl
20 mM β-ME
1 mM EDTA
50% glycerol
0.1% Triton® X-100
100 mM ATP, GTP, CTP and UTP
100 mM 2'F-ATP, 2'F-GTP, 2'F-CTP and 2'F-UTP
Inorganic Pyrophosphatase
RNase inhibitor Template:
Transcription templates can either be synthetic DNA, PCR products, or linearized vectors with 5'-ATTGGGCACCCGTAA-3' promoter sequence attached at 5' end. Synthetic templates purified with Urea-PAGE are useful.

Wild-Type and Y564F Syn5 RNA Polymerases

The Y564F mutant was prepared as the wild-type enzyme from a modified expression vector. Stock solution (1 mM) was kept at −20° C. A working solution (40 □M, 2 □M) in enzyme dilution buffer was prepared from the stock solution.

Example XVII

Incorporation of 2'-Modified dNTPs by Syn5 RNA Polymerase

According to certain aspects of the invention, wild-type Syn5 RNA polymerase was used in methods described herein for high yield 2'-F RNA synthesis, with DNA templates that allow incorporation of fewer than three 2'-F-dNTP into the first 12 nt of a full-length transcript and in a non-consecutive manner. Transcription initiation (synthesis of 2-12 nt RNA) can be the most unstable stage for an RNA polymerase. Once transcripts are extended over 12 nt, transcription elongation is robust and stable. To determine whether the incorporation of 2'-F-dNTP during the transcription initiation stage is a rate-limiting step of Syn5 RNA polymerase, Syn5 RNA polymerase transcription in the presence of 2'-F-dNTPs on DNA templates that allow various amounts of 2'-F-dNTP incorporation into the first 12 nt of the RNA products was compared. The following conditions were used.

For 20 μl reaction

| | |
|---|---|
| 5X Mg Buffer | 4 μl |
| 10 μM dsDNA template (1, 2 or 3)* | 9.8 μl |
| 40 U/μl RNaseOUT RNase inhibitor | 0.8 μl |
| 1 U/μL Inorganic Pyrophosphatase | 0.4 μl |
| 100 mM ATP or 2'-F-dATP | 1 μl |
| 100 mM GTP or 2'-F-dGTP | 1 μl |
| 100 mM CTP or 2'-F-dCTP | 1 μl |
| 100 mM UTP or 2'-F-dUTP | 1 μl |
| 40 μM Syn5 RNA Polymerase | 2 μl |

*Sequences of DNA templates (plus strands are shown; Syn5 promoter in italics; first 12 nt of transcript underlined):

1. Template for a 37 nt RNA:
5'-GGT*ATTGGGCACCCGTAA*GGAGAACCTTAAGGTTTAACTTTAAGACCCTTAAGTG-3'

2. Template for a 32 nt RNA:
5'-GCC*ATTGGGCACCCGTAA*GGGAGAGAGCATCGCTTGGTGCAGATCGGGAC-3'

3. Template for human mitochondrial tRNA$^{Pro}_{UGG}$:
5'-GCC*ATTGGGCACCCGTAA*CAGAGAATAGTTTAAATTAGAATCTTAGCTTTGGGTGCTAATGGTGGAGTTAAAGACTTTTTCTCTGACCA-3'

Figure 24:
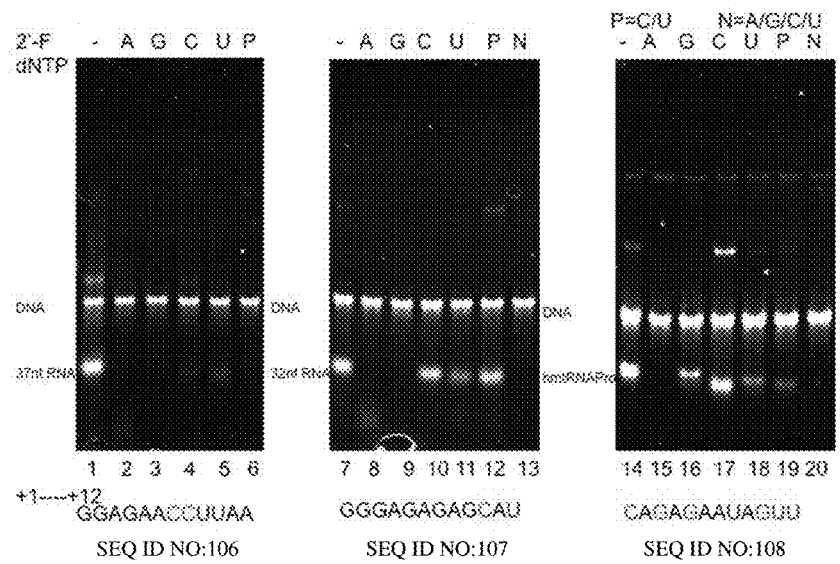
FIG. 24 depicts gels showing incorporation of 2'-F-dNTP into RNA using WT Syn5 RNA polymerase.

The reaction components were incubated at 37° C. for 4 hrs. Then 0.4 μl of the reaction mixture were loaded onto 10% TBE gel and stained with ethidium bromide. Results are shown in FIG. 24. As there are more 3 As in the 1-12 nt region of all three templates, none of them produces full-length transcript when ATP was replaced by 2'-F-dATP. See FIG. 1. lane 1 vs 2; 8 vs 7; 15 vs 14. Substantial yield for product containing 2'-F-dGMP was only observed for template 3, which has 3 non-consecutive Gs in the 1-12 region. See FIG. 1. lane 16 vs 14). Template 1 has also 3Gs but two of them are consecutive. 2'-F-dCTP was incorporated very well with template 2 and 3. See FIG. 1. lane 10 vs 7; lane 17 vs 14). Each has only one C in the 1-12 nt region, indicating that the Syn5 RNA polymerase has no intrinsic discrimination against 2'-F-dCTP during transcription elongation. Although there are only 2 Cs in the 1-12 nt region of template 1, two consecutive incorporations during the initiation stage prevented the efficient synthesis of RNA products containing 2'-F-dCMP. See FIG. 1. lane 4. With template 3 starting with C, 2'-F-dCTP was still efficiently incorporated.

T7 RNA polymerase, in contrast has very strict recognition of GTP as initiating nucleotide and strongly discriminate 2'-modified dGTP. For 2'-F-dUTP, template 2 shows an efficient incorporation due to the only one U in the 1-12 nt region. See FIG. 1. lane 11 vs 7. Although both template 1 and 3 have consecutive Us in the 1-12 region, they are distal in this region and presumably have less impact on the stability of the initiation complex, as a result they both allow low yield of the full-length products containing 2'-F-dUMP. See FIG. 1. lane 5 and 18. Accordingly, as supported by FIG. 1. lane 12 vs 7, the method described in this example can be successfully used to incorporate one or two different species of 2'-F-dNTP (such as the most common application of 2'-F-dCTP and 2'-F-dUTP incorporation).

Example XVII

Reducing Discrimination Against 2'-F-dNTP of Wild Type Syn5 RNA Polymerase

According to certain aspects of the invention, co-factors such as $Mg^{+2}$ and $Mn^{+2}$ are used to reduce discrimination against 2'-F-dNTP of wild-type Syn5 RNA polymerase. The optimum cofactor concentration of $Mg^{2+}$ or $Mn^{2+}$ is similar for Syn5 RNA polymerase, and $Mg^{2+}$ and $Mn^{2+}$ are provided as mixed cofactors for the Syn5 RNA polymerase. Without wishing to be bound by scientific theory, a substantial proportion of Syn5 RNA polymerase in the reaction may utilize one $Mg^{2+}$ and one $Mn^{2+}$ in their active sites for catalysis (based on the two-metal-ion mechanism for polymerase catalysis) so that both high overall yield and low discrimination against 2'-F-dNTP can be achieved with the methods described herein.

For 20 μl reaction

| | |
|---|---|
| 5X Mg Buffer or 5X Mg/Mn Buffer | 4 μl |
| 10 μM template 1 or 100 nM template 2* | 9.8 μl |
| 40 U/μl RNaseOUT RNase inhibitor | 0.8 μl |
| 1 U/μL Inorganic Pyrophosphatase | 0.4 μl |
| 100 mM ATP or 2'-F-dATP | 1 μl |
| 100 mM GTP or 2'-F-dGTP | 1 μl |
| 100 mM CTP or 2'-F-dCTP | 1 μl |
| 100 mM UTP or 2'-F-dUTP | 1 μl |
| 40 μM Syn5 RNA Polymerase | 2 μl |

*Sequences of DNA templates (plus strands are shown; Syn5 promoter in bold; first 12 nt of transcript underlined):

1. Template for a 37 nt RNA:
5'-GGT*ATTGGGCACCCGTAA*GGAGAACCTTAAGGTTTAACTTTAAGACCCTTAAGTG-3'

2. Template for a 2.7 knt RNA:
An NdeI linearized plasmid pUC19 containing a Syn5 promoter as described in Zhu et al., Nucleic Acids Res. 42: e33 (2014) hereby incorporated by reference in its entirety.

Figure 25A:
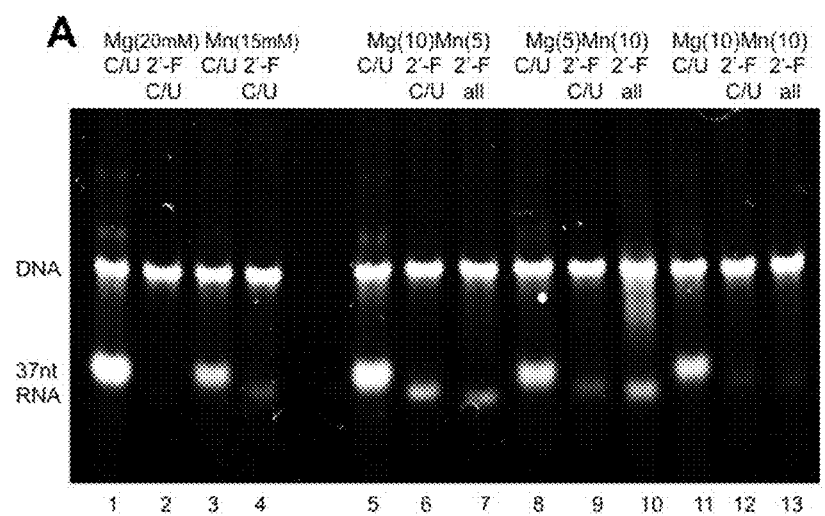
FIG. 25A depicts a gel showing that WT Syn5 polymerase incorporates 2'-F-C/UTP and all four 2'-F'dNTP in the presence of mixed cofactor $Mg^{2+}/Mn^{2+}$.
Figure 25B:
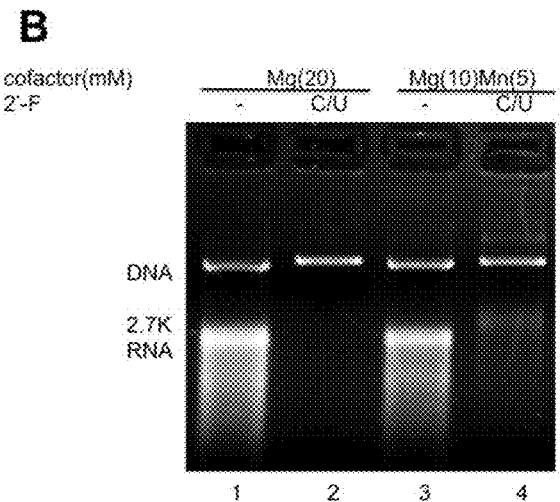
FIG. 25B depicts a gel comparing 2'-F'dNTP incorporation using $Mg^{2+}$ versus the mixed cofactor.

The reaction components were incubated at 37° C. for 4 hrs. 0.4 μl of the reaction mixture were loaded onto 10% TBE gel or 2% agarose gel and stained with ethidium bromide. Results are shown in FIG. 25A and FIG. 25B. As shown in FIG. 25A, at certain Mg2+/Mn2+ ratio (10 mM/5 mM, FIG. 2A lane 5-7), a desirable balance between high yield and low discrimination was achieved. At this condition, the maximum yield of non-modified RNA was similar to that at the optimum condition (Mg2+ only). See FIG. 25A lane 5 vs lane 1; FIG. 25B lane 3 vs lane 1). While the discrimination against 2'-F-dCTP/2'-F-dUTP at this condition is as low as that with Mn2+ only (compare FIG. 25A lane 3-6), the mixed cofactors provide a better yield of 2'-F-dCMP/2'-F-dUMP incorporated RNA compared to each single cofactor (FIG. 25A lane 6 vs lane 4 and lane 2; FIG. 25B lane 4 vs lane 2). The reduced discrimination also applies to 2'-F-dATP and 2'-F-dGTP, as a substantial yield of 2-F-RNA with all four 2'-F-dNMPs replacements was observed (FIG. 25A lane 7).

Example XVIII

Syn5 RNA Polymerase Y564F Mutant for the Incorporation of 2'-F-dNTPs

Figure 26:
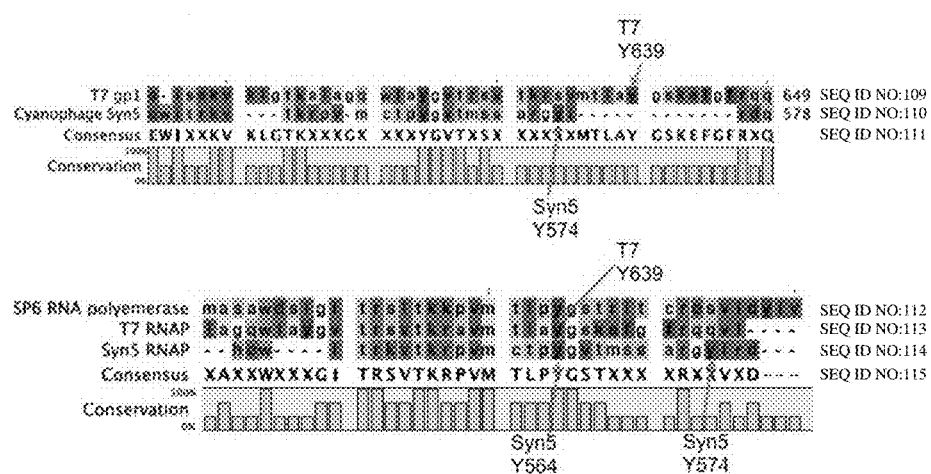
FIG. 26 depicts possible Syn5 RNAP mutants with improved 2' flexibility.

According to certain aspects of the invention, a Syn5 RNA polymerase Y564F mutant is provided for the incorporation of 2'-F-dNTPs. According to certain aspects, Syn5 RNA polymerase shares <30% sequence identity to T7 RNA polymerase while alignment analysis suggests that one of the two tyrosines (Y564 and Y574) in Syn5 RNA polymerase may be homologous to T7 Y639. See FIG. 26.

Figure 27:
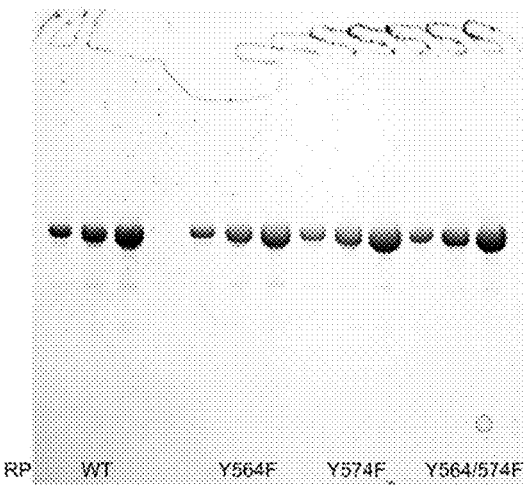
FIG. 27 depicts a gel showing purification of Syn5 RNAP mutants.

Syn5 RNA polymerases containing Y564F and/or Y574F mutation were constructed using a known PCR mutagenesis method (see Higuchi et al., Nucleic Acids Res. 16:7351-7367 (1988) hereby incorporated by reference in its entirety), expressed and purified using known methods. The wild type gene background for the mutants was also modified, with the internal Syn5 promoter removed to reduce toxicity and increase the yield of the protein when expressed in *E. coli*. Purified proteins were analyzed by SDS-PAGE. See FIG. 27. The mutants were used to incorporate 2'-F-dNTPs as described below.

For 20 □l reaction

| | |
|---|---|
| 5X Mg Buffer | 4 □l |
| 100 nM template 1 or 10 □M template 2* | 9.8 □l |
| 40 U/□l RNaseOUT RNase inhibitor | 0.8 □l |
| 1 U/□L Inorganic Pyrophosphatase | 0.4 □l |
| 100 mM ATP or 2'-F-dATP | 1 □l |
| 100 mM GTP or 2'-F-dGTP | 1 □l |
| 100 mM CTP or 2'-F-dCTP | 1 □l |
| 100 mM UTP or 2'-F-dUTP | 1 □l |
| 40 □M or 2 □M WT or Y564F Syn5 RNA Polymerase | 2 □l |

*Sequences of DNA templates (plus strands are shown; Syn5 promoter in bold; first 12 nt of transcript underlined):

1. Template for a 2.7 knt RNA:

An NdeI linearlized plasmid pUC19 containing a Syn5 promoter as described in Zhu et al., Nucleic Acids Res. 42: e33.

2. Template for human mitochondirial tRNA$^{Pro}_{UGG}$:

5'-GCCATTGGGCACCCGTAA<u>CAGAGAATAGTTT</u>AAATTAGAATCTTA
GCTTTGGGTGCTAATGGTGGAGTTAAAGACTTTTTCTCTGACCA-3'

Figure 28A:
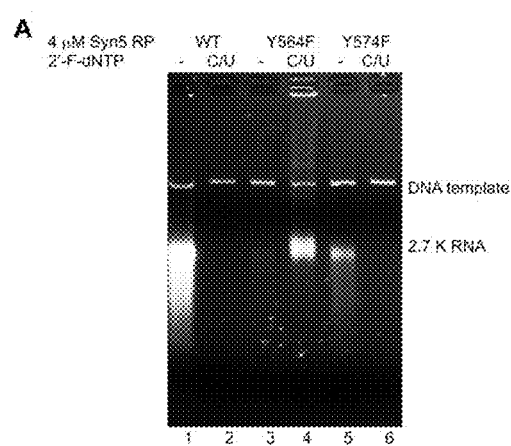
FIGS. 28A, 28B, 28C and 28D depict gels showing a preference for 2'-F-dC/UTP over rC/UTP by Syn5 RNAP-Y564F.
Figure 28B:
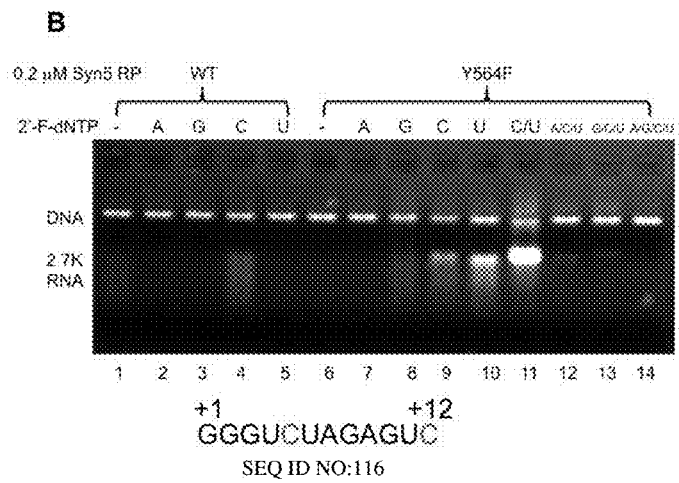
Figure 28C:
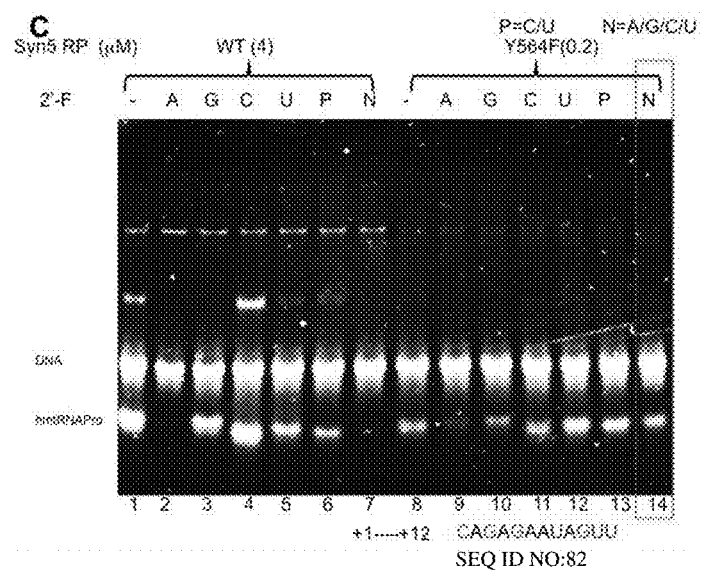
Figure 28D:
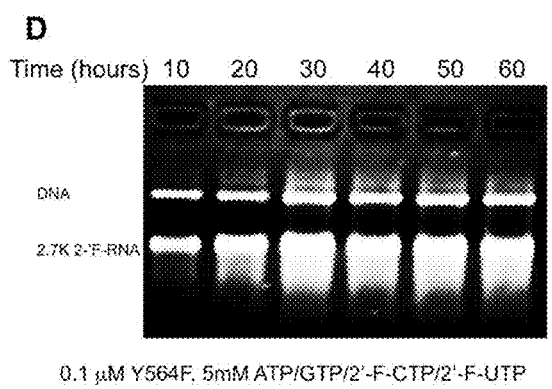

The reaction components were incubated at 37° C. for 4 hrs. 0.4 □l of the reaction mixture was loaded onto 2% agarose gel or 10% TBE gel and stained with ethidium bromide. Results are shown in FIG. 28A, FIG. 28B, FIG. 28C and FIG. 28D. The Y564F mutation does change the recognition of the 2'-group in the nucleotide substrates by Syn5 RNA polymerase. But, unlike T7 RNA polymerase, Y639F discriminates against 2'-F-dNTPs several fold. The Syn5 RNA polymerase Y564F prefers 2'-F-dCTP and 2'-F-dUTP to canonical rCTP and rUTP. See FIG. 28A lane 4 vs 3; FIG. 28B lane 9-11 vs 6; FIG. 28C lane 11-13 vs 8). The discrimination to 2'-F-dATP and 2'-F-dGTP was also reduced by the Y564F mutation (FIG. 28B lane 8 vs 3; FIG. 28C lane 9 vs 2). Full-length transcript including all four 2'-F-dNMPs was synthesized by Syn5 RNA polymerase Y564F on a template starting with C. See FIG. 28C lane 14. At a low concentration, Syn5 RNA polymerase Y564F stably synthesizes long RNA containing 2'-F-dCMP and 2'-F-dUMP. See FIG. 28D.

EQUIVALENTS

Other embodiments will be evident to those of skill in the art. It should be understood that the foregoing description is provided for clarity only and is merely exemplary. The spirit and scope of the present invention are not limited to the above example, but are encompassed by the claims.

All publications, patents and patent applications cited above are incorporated by reference herein in their entirety for all purposes to the same extent as if each individual publication or patent application were specifically indicated to be so incorporated by reference.

What is claimed is:

1. A method of performing in vitro transcription comprising the steps of:
providing a cDNA comprising a cyanophage Syn5 RNA polymerase (RNAP) promoter sequence and a nucleic acid template sequence, nucleotides and a Y564F mutant cyanophage Syn5 RNAP, wherein said Syn5 RNA Polymerase (RNAP) has at least 90% sequence identity to the amino acid sequence of SEQ ID NO:23; and
incubating the cDNA comprising the cyanophage Syn5 RNA polymerase (RNAP) promoter sequence and the nucleic acid template sequence, the nucleotides and the Y564F mutant cyanophage Syn5 RNAP together for a sufficient time to produce transcripts.

2. The method of claim 1, wherein the incubating step is performed in the presence of salt at a concentration of at least about 100 mM.

3. The method of claim 2, wherein the salt is KCl or NaCl.

4. The method of claim 1, wherein the incubating step is performed at between about 4° C. and about 37° C.

5. The method of claim 1, wherein the nucleotides are modified nucleotides.

6. The method of claim 1, wherein the Y564F mutant cyanophage Syn5 RNAP includes a protein tag.

7. The method of claim 1, wherein the transcripts are greater than about 10,000 nucleotides in length.

8. The method of claim 1, wherein the nucleic acid template sequence comprises one or more T7 terminator-like sequences and the transcripts produced are full-length.

9. The method of claim 1, wherein the in vitro transcription is performed in the presence of one or any combination of $Mg^{2+}$, $Mn^{2+}$ and $Fe^{2+}$.

10. The method of claim 1, wherein greater than about 90% of the transcripts lack a nucleotide overhang at the 3' ends.

11. A method of performing in vitro transcription comprising the steps of:
providing a reaction mixture of a cDNA comprising a cyanophage Syn5 RNA polymerase (RNAP) promoter sequence and a nucleic acid template sequence, nucleotides, one or more 2'-modified nucleotides, $Mg^{2+}$ and $Mn^{2+}$r and a Y564F mutant cyanophage Syn5 RNAP, wherein said Syn5 RNA Polymerase (RNAP) has at least 90% sequence identity to the amino acid sequence of SEQ ID NO:23 and
incubating the reaction mixture for a sufficient time to produce a transcript including the one or more 2'-modified nucleotides.

12. The method of claim 11 wherein the $Mg^{2+}$ and $Mn^{2+}$ are present in a ratio of between about 2 to 1 to about 1 to 2.

13. The method of claim 11 wherein the $Mg^{2+}$ and $Mn^{2+}$ are each present in the reaction mixture at a concentration of about 5 mM or higher.

14. The method of claim 11 wherein the one or more 2'-modified nucleotides is 2'-F-dATP, 2'-F-dGTP, 2'-F-dCTP, 2'-F-dUTP, 2'-$NH_2$-dATP, 2'-$NH_2$-dGTP, 2'-$NH_2$-dCTP, 2'-$NH_2$-dUTP, 2'-OMe-dATP, 2'-OMe-dGTP, 2'-OMe-dCTP, or 2'-OMe-dUTP.

15. The method of claim 11 wherein the nucleic acid template sequence is a DNA template sequence and the transcript includes fewer than three 2'-modified nucleotides within the first 12 nucleotides of the transcript and wherein the three 2'-modified nucleotides within the first 12 nucleotides are non-consecutive.

16. The method of claim 11 wherein the nucleic acid template sequence includes a sequence which when transcribed by the cyanophage Syn5 RNAP produces a transcript including fewer than three 2'-modified nucleotides within the first 12 nucleotides of the transcript.

17. The method of claim 11 wherein discrimination between the modified nucleotides is reduced.

* * * * *

SEQUENCE LISTING

<160> NUMBER OF SEQ ID NOS: 116

<210> SEQ ID NO 1
<211> LENGTH: 15
<212> TYPE: DNA
<213> ORGANISM: Artificial
<220> FEATURE:
<223> OTHER INFORMATION: Syn5 RNAP Promoter

<400> SEQUENCE: 1
attgggcacc cgtaa                                              15

```
<210> SEQ ID NO 2
<211> LENGTH: 20
<212> TYPE: DNA
<213> ORGANISM: Artificial
<220> FEATURE:
<223> OTHER INFORMATION: T7 RNAP promoter

<400> SEQUENCE: 2
taatacgact cactataggg                                               20

<210> SEQ ID NO 3
<211> LENGTH: 95
<212> TYPE: DNA
<213> ORGANISM: Artificial
<220> FEATURE:
<223> OTHER INFORMATION: S5P-tDNAR

<400> SEQUENCE: 3
gccattgggc acccgtaagc atccgtagtt cagctggata gagtactcgg ctacgaaccg   60
agcggtcgga ggttcgaatc ctcccggatg cacca                              95

<210> SEQ ID NO 4
<211> LENGTH: 97
<212> TYPE: DNA
<213> ORGANISM: Artificial
<220> FEATURE:
<223> OTHER INFORMATION: T7P-tDNAR

<400> SEQUENCE: 4
gcctaatacg actcactata gcatccgtag ttcagctgga tagagtactc ggctacgaac   60
cgagcggtcg gaggttcgaa tcctcccgga tgcacca                            97

<210> SEQ ID NO 5
<211> LENGTH: 12
<212> TYPE: DNA
<213> ORGANISM: Artificial
<220> FEATURE:
<223> OTHER INFORMATION: 12 bp sequence in the Syn5 phage genome,
      repeated several times.

<400> SEQUENCE: 5
ccttaattaa ct                                                       12

<210> SEQ ID NO 6
<211> LENGTH: 16
<212> TYPE: DNA
<213> ORGANISM: Artificial
<220> FEATURE:
<223> OTHER INFORMATION: 1 kb fragment of the P-SSP7

<400> SEQUENCE: 6
aacccctacg tataca                                                   16

<210> SEQ ID NO 7
<211> LENGTH: 8
<212> TYPE: PRT
<213> ORGANISM: Artificial
<220> FEATURE:
<223> OTHER INFORMATION: Strep-tag II

<400> SEQUENCE: 7

Trp Ser His Pro Gln Phe Glu Lys
1               5

<210> SEQ ID NO 8
```

```
<211> LENGTH: 15
<212> TYPE: PRT
<213> ORGANISM: Artificial
<220> FEATURE:
<223> OTHER INFORMATION: Avi tag

<400> SEQUENCE: 8

Gly Leu Asn Asp Ile Phe Glu Ala Gln Lys Ile Glu Trp His Glu
1               5                   10                  15

<210> SEQ ID NO 9
<211> LENGTH: 26
<212> TYPE: PRT
<213> ORGANISM: Artificial
<220> FEATURE:
<223> OTHER INFORMATION: Calmodulin tag

<400> SEQUENCE: 9

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 10
<211> LENGTH: 8
<212> TYPE: PRT
<213> ORGANISM: Artificial
<220> FEATURE:
<223> OTHER INFORMATION: FLAG tag

<400> SEQUENCE: 10

Asp Tyr Lys Asp Asp Asp Asp Lys
1               5

<210> SEQ ID NO 11
<211> LENGTH: 9
<212> TYPE: PRT
<213> ORGANISM: Artificial
<220> FEATURE:
<223> OTHER INFORMATION: HA tag

<400> SEQUENCE: 11

Tyr Pro Tyr Asp Val Pro Asp Tyr Ala
1               5

<210> SEQ ID NO 12
<211> LENGTH: 6
<212> TYPE: PRT
<213> ORGANISM: Artificial
<220> FEATURE:
<223> OTHER INFORMATION: His tag

<400> SEQUENCE: 12

His His His His His His
1               5

<210> SEQ ID NO 13
<211> LENGTH: 10
<212> TYPE: PRT
<213> ORGANISM: Artificial
<220> FEATURE:
<223> OTHER INFORMATION: Myc tag

<400> SEQUENCE: 13

Glu Gln Lys Leu Ile Ser Glu Glu Asp Leu
1               5                   10
```

<210> SEQ ID NO 14
<211> LENGTH: 15
<212> TYPE: PRT
<213> ORGANISM: Artificial
<220> FEATURE:
<223> OTHER INFORMATION: S tag

<400> SEQUENCE: 14

Lys Glu Thr Ala Ala Ala Lys Phe Glu Arg Gln His Met Asp Ser
1               5                   10                  15

<210> SEQ ID NO 15
<211> LENGTH: 38
<212> TYPE: PRT
<213> ORGANISM: ARTIFICIAL
<220> FEATURE:
<223> OTHER INFORMATION: SBP tag

<400> SEQUENCE: 15

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 16
<211> LENGTH: 13
<212> TYPE: PRT
<213> ORGANISM: ARTIFICIAL
<220> FEATURE:
<223> OTHER INFORMATION: Softag 1

<400> SEQUENCE: 16

Ser Leu Ala Glu Leu Leu Asn Ala Gly Leu Gly Gly Ser
1               5                   10

<210> SEQ ID NO 17
<211> LENGTH: 8
<212> TYPE: PRT
<213> ORGANISM: ARTIFICIAL
<220> FEATURE:
<223> OTHER INFORMATION: Softag 3

<400> SEQUENCE: 17

Thr Gln Asp Pro Ser Arg Val Gly
1               5

<210> SEQ ID NO 18
<211> LENGTH: 14
<212> TYPE: PRT
<213> ORGANISM: ARTIFICIAL
<220> FEATURE:
<223> OTHER INFORMATION: V5 tag

<400> SEQUENCE: 18

Gly Lys Pro Ile Pro Asn Pro Leu Leu Gly Leu Asp Ser Thr
1               5                   10

<210> SEQ ID NO 19
<211> LENGTH: 8
<212> TYPE: PRT
<213> ORGANISM: ARTIFICIAL
<220> FEATURE:
<223> OTHER INFORMATION: Xpress tag

<400> SEQUENCE: 19

Asp Leu Tyr Asp Asp Asp Asp Lys
1               5

<210> SEQ ID NO 20
<211> LENGTH: 16
<212> TYPE: PRT
<213> ORGANISM: ARTIFICIAL
<220> FEATURE:
<223> OTHER INFORMATION: Isopeptag

<400> SEQUENCE: 20

Thr Asp Lys Asp Met Thr Ile Thr Phe Thr Asn Lys Lys Asp Ala Glu
1               5                   10                  15

<210> SEQ ID NO 21
<211> LENGTH: 13
<212> TYPE: PRT
<213> ORGANISM: ARTIFICIAL
<220> FEATURE:
<223> OTHER INFORMATION: SpyTag

<400> SEQUENCE: 21

Ala His Ile Val Met Val Asp Ala Tyr Lys Pro Thr Lys
1               5                   10

<210> SEQ ID NO 22
<211> LENGTH: 2340
<212> TYPE: DNA
<213> ORGANISM: ARTIFICIAL
<220> FEATURE:
<223> OTHER INFORMATION: cDNA sequence encoding a cyanophage Syn5 RNAP

<400> SEQUENCE: 22

```
atgtccttcg atctcatcgc tcgccagctt cagcgtgaga ccgaggccgc ggagctggcc      60
cgcaagcgtc tacaagacgc ccgacgcgag gccaatgaac gctcctatgc ctcaagcaac     120
atcgagagcc gcaaggccat cgcgacgttc ctggatccca tcgcccaacg catcggcgaa     180
cgcctgttca cgctacggcg tggtactggt gcagttgatg ccgccgaggt ctacaagcat     240
ctgaagaacg ccgatcacca tcatctggcg ctcatcacga tgaagacagc cctggacgtc     300
ctgggcaaag atcccgagcc acagatccaa cagctgacca cagccattgg ccgcaacatc     360
cagctggagc tccgcctcac gtactacgcc gaggaaaacc cggagctcta caaacaggcc     420
tcccgcttct ccacgcagg cactggcacc cgccagaaag ccacggtgat caaactcaag     480
ttcaaccgcg agggcattga gtgggaccaa tggtcccgcg tcacctgtca aggttggc      540 caatggctca tgttggctat ggccgacgtc accggctgga ttgaacgggc aaccgaccga     600
accagtggag gacgcaaaac caagacccgc atctgctact cccgcgagtt cttgcagcat     660
cgggacacaa tcctcgcagc agctgagcag ttggccttct gccagtggcc catgctttgc     720
cctcccattg agtggtccaa cgaccacaac ggtgggtacc tgagcgaaca gatccggcgg     780
gtcaatccgc tgattcgtaa aacgggtcca ttgggcaccc gtaagcaagg agacatacccc    840 cttgcgatgc tcaacaacct gcagggtcag gcctacaagg tcaaccctga agttctcgac    900
atagcgaacc actgctacga gtccaacgtg accgtaggca agttcatacg ccacgctccc    960
ctacctgttc caccatcacc cggtgaggac tgtacagagg accagctcac agcctataaa   1020
cgggcacgac gtgaggccga ggacttcaac gcacagatca gtcagaagaa ctggcgcacg   1080
accgaggtca tgtatgtggc ccgcaagtac gccgacgagg cctccttctg gatgcccgcc   1140
```

```
agcttcgact atcgcggccg tgtttacttt ctgaacactg ccctcaaccc gcagggact     1200 gacttcgaca aggcgctcct ttacttcgct gaggagggtc cggtcaacga atggtggcta    1260
tccttccacg tcgcgaccac ctacggcctc gacaaggaga ccatggtcaa ccgggtccaa    1320
tgggctcggg acaaccacga gctcatcgat cgcatcgcct ctgacccgt ccgccatacc    1380 gagtggcacg acgctgacga gccctggtgc ttcctggctg cctgcctcga gtacaaggcc    1440
tgcgtgatcg atggcaccaa acagaccagc ggcctccta tcgggatcga cgccacctgt    1500
tcaggcctgc agcacctcgc tgctatgacc cgctgcggac gcacagccgc cctggtcaac    1560
gtgacaccga ccgacaagcc ggccgatgct acaagaccg tggcgcaagc atccctcaag    1620
catctcccca aggagcagca cgagtggatc acccgcaagg tcaccaaaag gcccgtcatg    1680
tgcacaccct acggggtgac catgtcatcg gcccgcggct acatccgcga tcagctggtg    1740
aaggacggcc acaaggagga cctccgatct cctggcgtgc tcaacggcat cgtcaaggcg    1800
atctttaatg aggccatccc tgaggtcatc cccggccccg tgcaggtcat ggcctggctc    1860
aagcgttcag ctggtcagat catcgaccgg ggtgattcca ccatcacgtg gaccacgccc    1920
tcaggcttcg aggttgttca agacctcaaa aagtccaaga cctacgaggt caagacccgc    1980
atcatgggcg gagcacggat caagctccaa gtgggcgacg ggttcaccga cgagcccgac    2040
cgtgaccacc acaaaagcgc actggctccc aacgtggtgc acagcaacga tgcgtctctc    2100
ctccacctga ccttcgcctt ctgggacaag cccttcacgg tcatccatga ctgtgtcctg    2160
ggccgttcct gcgacatgga tcagatgggc tccgacatcc ggcttcattt cgccgagatg    2220
tacaaggccg acgtgatgca agactgggcc gaccaggtgg gcgttgagct ccctgtcgac    2280
ctgatcaaaa acacgctcga catcgacagc gtcaaccagt cccttactt cttctcctga    2340
```

<210> SEQ ID NO 23
<211> LENGTH: 779
<212> TYPE: PRT
<213> ORGANISM: ARTIFICIAL
<220> FEATURE:
<223> OTHER INFORMATION: Amino acid sequence of a cyanophage Syn5 RNAP

<400> SEQUENCE: 23

```
Met Ser Phe Asp Leu Ile Ala Arg Gln Leu Gln Arg Glu Thr Glu Ala
1               5                   10                  15

Ala Glu Leu Ala Arg Lys Arg Leu Gln Asp Ala Arg Arg Glu Ala Asn
            20                  25                  30

Glu Arg Ser Tyr Ala Ser Ser Asn Ile Glu Ser Arg Lys Ala Ile Ala
        35                  40                  45

Thr Phe Leu Asp Pro Ile Ala Gln Arg Ile Gly Glu Arg Leu Phe Thr
    50                  55                  60

Leu Arg Arg Gly Thr Gly Ala Val Asp Ala Glu Val Tyr Lys His
65                  70                  75                  80

Leu Lys Asn Ala Asp His His His Leu Ala Leu Ile Thr Met Lys Thr
                85                  90                  95

Ala Leu Asp Val Leu Gly Lys Asp Pro Glu Pro Gln Ile Gln Gln Leu
            100                 105                 110

Thr Thr Ala Ile Gly Arg Asn Ile Gln Leu Glu Leu Arg Leu Thr Tyr
        115                 120                 125

Tyr Ala Glu Glu Asn Pro Glu Leu Tyr Lys Gln Ala Ser Arg Phe Phe
    130                 135                 140

His Ala Gly Thr Gly Thr Arg Gln Lys Ala Thr Val Ile Lys Leu Lys
145                 150                 155                 160
```

```
Phe Asn Arg Glu Gly Ile Glu Trp Asp Gln Trp Ser Arg Val Thr Cys
                165                 170                 175

His Lys Val Gly Gln Trp Leu Met Leu Ala Met Ala Asp Val Thr Gly
            180                 185                 190

Trp Ile Glu Arg Ala Thr Asp Arg Thr Ser Gly Gly Arg Lys Thr Lys
        195                 200                 205

Thr Arg Ile Cys Tyr Ser Arg Glu Phe Leu Gln His Arg Asp Thr Ile
    210                 215                 220

Leu Ala Ala Ala Glu Gln Leu Ala Phe Cys Gln Trp Pro Met Leu Cys
225                 230                 235                 240

Pro Pro Ile Glu Trp Ser Asn Asp His Asn Gly Gly Tyr Leu Ser Glu
                245                 250                 255

Gln Ile Arg Arg Val Asn Pro Leu Ile Arg Lys Thr Gly Pro Leu Gly
            260                 265                 270

Thr Arg Lys Gln Gly Asp Ile Pro Leu Ala Met Leu Asn Asn Leu Gln
        275                 280                 285

Gly Gln Ala Tyr Lys Val Asn Pro Glu Val Leu Asp Ile Ala Asn His
    290                 295                 300

Cys Tyr Glu Ser Asn Val Thr Val Gly Lys Phe Ile Arg His Ala Pro
305                 310                 315                 320

Leu Pro Val Pro Pro Ser Pro Gly Glu Asp Cys Thr Glu Asp Gln Leu
                325                 330                 335

Thr Ala Tyr Lys Arg Ala Arg Arg Glu Ala Glu Asp Phe Asn Ala Gln
            340                 345                 350

Ile Ser Gln Lys Asn Trp Arg Thr Thr Glu Val Met Tyr Val Ala Arg
        355                 360                 365

Lys Tyr Ala Asp Glu Ala Ser Phe Trp Met Pro Ala Ser Phe Asp Tyr
    370                 375                 380

Arg Gly Arg Val Tyr Phe Leu Asn Thr Ala Leu Asn Pro Gln Gly Thr
385                 390                 395                 400

Asp Phe Asp Lys Ala Leu Leu Tyr Phe Ala Glu Gly Pro Val Asn
                405                 410                 415

Glu Trp Trp Leu Ser Phe His Val Ala Thr Thr Tyr Gly Leu Asp Lys
            420                 425                 430

Glu Thr Met Val Asn Arg Val Gln Trp Ala Arg Asp Asn His Glu Leu
        435                 440                 445

Ile Asp Arg Ile Ala Ser Asp Pro Val Arg His Thr Glu Trp His Asp
    450                 455                 460

Ala Asp Glu Pro Trp Cys Phe Leu Ala Ala Cys Leu Glu Tyr Lys Ala
465                 470                 475                 480

Cys Val Ile Asp Gly Thr Lys Gln Thr Ser Gly Leu Pro Ile Gly Ile
                485                 490                 495

Asp Ala Thr Cys Ser Gly Leu Gln His Leu Ala Ala Met Thr Arg Cys
            500                 505                 510

Gly Arg Thr Ala Ala Leu Val Asn Val Thr Pro Thr Asp Lys Pro Ala
        515                 520                 525

Asp Ala Tyr Lys Thr Val Ala Gln Ala Ser Leu Lys His Leu Pro Lys
    530                 535                 540

Glu Gln His Glu Trp Ile Thr Arg Lys Val Thr Lys Arg Pro Val Met
545                 550                 555                 560

Cys Thr Pro Tyr Gly Val Thr Met Ser Ser Ala Arg Gly Tyr Ile Arg
                565                 570                 575
```

Asp Gln Leu Val Lys Asp Gly His Lys Glu Asp Leu Arg Ser Pro Gly
            580                 585                 590

Val Leu Asn Gly Ile Val Lys Ala Ile Phe Asn Glu Ala Ile Pro Glu
        595                 600                 605

Val Ile Pro Gly Pro Val Gln Val Met Ala Trp Leu Lys Arg Ser Ala
        610                 615                 620

Gly Gln Ile Ile Asp Arg Gly Asp Ser Thr Ile Thr Trp Thr Thr Pro
625                 630                 635                 640

Ser Gly Phe Glu Val Gln Asp Leu Lys Lys Ser Lys Thr Tyr Glu
            645                 650                 655

Val Lys Thr Arg Ile Met Gly Ala Arg Ile Lys Leu Gln Val Gly
        660                 665                 670

Asp Gly Phe Thr Asp Glu Pro Asp Arg Asp His His Lys Ser Ala Leu
            675                 680                 685

Ala Pro Asn Val Val His Ser Asn Asp Ala Ser Leu Leu His Leu Thr
        690                 695                 700

Phe Ala Phe Trp Asp Lys Pro Phe Thr Val Ile His Asp Cys Val Leu
705                 710                 715                 720

Gly Arg Ser Cys Asp Met Asp Gln Met Gly Ser Asp Ile Arg Leu His
                725                 730                 735

Phe Ala Glu Met Tyr Lys Ala Asp Val Met Gln Asp Trp Ala Asp Gln
            740                 745                 750

Val Gly Val Glu Leu Pro Val Asp Leu Ile Lys Asn Thr Leu Asp Ile
        755                 760                 765

Asp Ser Val Asn Gln Ser Leu Tyr Phe Phe Ser
770                 775

<210> SEQ ID NO 24
<211> LENGTH: 35
<212> TYPE: DNA
<213> ORGANISM: ARTIFICIAL
<220> FEATURE:
<223> OTHER INFORMATION: PCR primer

<400> SEQUENCE: 24
ggaattccat atgtccttcg atctcatcgc tcgcc                               35

<210> SEQ ID NO 25
<211> LENGTH: 40
<212> TYPE: DNA
<213> ORGANISM: ARTIFICIAL
<220> FEATURE:
<223> OTHER INFORMATION: PCR primer

<400> SEQUENCE: 25
actggcggcc gctcaggaga agaagtaaag ggactggttg                          40

<210> SEQ ID NO 26
<211> LENGTH: 78
<212> TYPE: DNA
<213> ORGANISM: ARTIFICIAL
<220> FEATURE:
<223> OTHER INFORMATION: PCR primer

<400> SEQUENCE: 26
ggaattccat atgcatcacc atcaccatca cggcggaggt ggaggctcct tcgatctcat    60
cgctcgccag cttcagcg                                                  78

<210> SEQ ID NO 27

```
<211> LENGTH: 23
<212> TYPE: DNA
<213> ORGANISM: ARTIFICIAL
<220> FEATURE:
<223> OTHER INFORMATION: PCR primer

<400> SEQUENCE: 27
ctgcggacgc acagccgccc tgg                                              23

<210> SEQ ID NO 28
<211> LENGTH: 25
<212> TYPE: DNA
<213> ORGANISM: ARTIFICIAL
<220> FEATURE:
<223> OTHER INFORMATION: PCR primer

<400> SEQUENCE: 28
gccttctggg acaagccctt cacgg                                            25

<210> SEQ ID NO 29
<211> LENGTH: 40
<212> TYPE: DNA
<213> ORGANISM: ARTIFICIAL
<220> FEATURE:
<223> OTHER INFORMATION: PCR primer

<400> SEQUENCE: 29
actggcggcc gcctagggtt tgagccatga ttcggggatg                            40

<210> SEQ ID NO 30
<211> LENGTH: 46
<212> TYPE: DNA
<213> ORGANISM: ARTIFICIAL
<220> FEATURE:
<223> OTHER INFORMATION: PCR primer

<400> SEQUENCE: 30
cgatgcggcc gctcagtaag gataatcagc atcccgacca tggagg                     46

<210> SEQ ID NO 31
<211> LENGTH: 35
<212> TYPE: DNA
<213> ORGANISM: ARTIFICIAL
<220> FEATURE:
<223> OTHER INFORMATION: PCR primer

<400> SEQUENCE: 31
ggaattccat atgcctgcct tccgatctgg tctgg                                 35

<210> SEQ ID NO 32
<211> LENGTH: 40
<212> TYPE: DNA
<213> ORGANISM: ARTIFICIAL
<220> FEATURE:
<223> OTHER INFORMATION: PCR primer

<400> SEQUENCE: 32
actggcggcc gctcatgtgt tgcggttgta tcggatggtg                            40

<210> SEQ ID NO 33
<211> LENGTH: 35
<212> TYPE: DNA
<213> ORGANISM: ARTIFICIAL
<220> FEATURE:
<223> OTHER INFORMATION: PCR primer

<400> SEQUENCE: 33
```

```
ggaattccat atgacgactt ctgacgttgc ccacc                              35
```

<210> SEQ ID NO 34
<211> LENGTH: 41
<212> TYPE: DNA
<213> ORGANISM: ARTIFICIAL
<220> FEATURE:
<223> OTHER INFORMATION: PCR primer

<400> SEQUENCE: 34

```
actggcggcc gcttagtggc aatccgccca ggagttacct g                       41
```

<210> SEQ ID NO 35
<211> LENGTH: 23
<212> TYPE: DNA
<213> ORGANISM: ARTIFICIAL
<220> FEATURE:
<223> OTHER INFORMATION: PCR primer

<400> SEQUENCE: 35

```
cgattcaggt aagcccaaga ttg                                           23
```

<210> SEQ ID NO 36
<211> LENGTH: 39
<212> TYPE: DNA
<213> ORGANISM: ARTIFICIAL
<220> FEATURE:
<223> OTHER INFORMATION: PCR primer

<400> SEQUENCE: 36

```
actggcggcc gctcattgcg gggtaataag tatgggtac                          39
```

<210> SEQ ID NO 37
<211> LENGTH: 35
<212> TYPE: DNA
<213> ORGANISM: ARTIFICIAL
<220> FEATURE:
<223> OTHER INFORMATION: PCR primer

<400> SEQUENCE: 37

```
ggaattccat atgacctttg agcctcccac ccttc                              35
```

<210> SEQ ID NO 38
<211> LENGTH: 40
<212> TYPE: DNA
<213> ORGANISM: ARTIFICIAL
<220> FEATURE:
<223> OTHER INFORMATION: PCR primer

<400> SEQUENCE: 38

```
cccaagcttt tactcggcgc aggatgaaca gaattggtcg                         40
```

<210> SEQ ID NO 39
<211> LENGTH: 25
<212> TYPE: DNA
<213> ORGANISM: ARTIFICIAL
<220> FEATURE:
<223> OTHER INFORMATION: PCR primer

<400> SEQUENCE: 39

```
cccggtgagg actgtacaga ggacc                                         25
```

<210> SEQ ID NO 40
<211> LENGTH: 25
<212> TYPE: DNA

```
<213> ORGANISM: ARTIFICIAL
<220> FEATURE:
<223> OTHER INFORMATION: PCR primer

<400> SEQUENCE: 40
gggactgact tcgacaaggc gctcc                                              25

<210> SEQ ID NO 41
<211> LENGTH: 25
<212> TYPE: DNA
<213> ORGANISM: ARTIFICIAL
<220> FEATURE:
<223> OTHER INFORMATION: PCR primer

<400> SEQUENCE: 41
ccctggtgct tcctggctgc ctgcc                                              25

<210> SEQ ID NO 42
<211> LENGTH: 25
<212> TYPE: DNA
<213> ORGANISM: ARTIFICIAL
<220> FEATURE:
<223> OTHER INFORMATION: PCR primer

<400> SEQUENCE: 42
gccttctggg acaagccctt cacgg                                              25

<210> SEQ ID NO 43
<211> LENGTH: 25
<212> TYPE: DNA
<213> ORGANISM: ARTIFICIAL
<220> FEATURE:
<223> OTHER INFORMATION: PCR primer

<400> SEQUENCE: 43
cacggggccg gggatgacct caggg                                              25

<210> SEQ ID NO 44
<211> LENGTH: 25
<212> TYPE: DNA
<213> ORGANISM: ARTIFICIAL
<220> FEATURE:
<223> OTHER INFORMATION: PCR primer

<400> SEQUENCE: 44
gagatgcttg agggatgctt gcgcc                                              25

<210> SEQ ID NO 45
<211> LENGTH: 24
<212> TYPE: DNA
<213> ORGANISM: ARTIFICIAL
<220> FEATURE:
<223> OTHER INFORMATION: PCR primer

<400> SEQUENCE: 45
accacaacgg tgggtacctg agcg                                               24

<210> SEQ ID NO 46
<211> LENGTH: 25
<212> TYPE: DNA
<213> ORGANISM: ARTIFICIAL
<220> FEATURE:
<223> OTHER INFORMATION: PCR primer

<400> SEQUENCE: 46
gtaaaacggg tccattgggc acccg                                              25
```

```
<210> SEQ ID NO 47
<211> LENGTH: 25
<212> TYPE: DNA
<213> ORGANISM: ARTIFICIAL
<220> FEATURE:
<223> OTHER INFORMATION: PCR primer

<400> SEQUENCE: 47
ttgcgatgct caacaacctg caggg                                            25

<210> SEQ ID NO 48
<211> LENGTH: 25
<212> TYPE: DNA
<213> ORGANISM: ARTIFICIAL
<220> FEATURE:
<223> OTHER INFORMATION: PCR primer

<400> SEQUENCE: 48
agttctcgac atagcgaacc actgc                                            25

<210> SEQ ID NO 49
<211> LENGTH: 25
<212> TYPE: DNA
<213> ORGANISM: ARTIFICIAL
<220> FEATURE:
<223> OTHER INFORMATION: PCR primer

<400> SEQUENCE: 49
ggcaagttca tacgccacgc tcccc                                            25

<210> SEQ ID NO 50
<211> LENGTH: 25
<212> TYPE: DNA
<213> ORGANISM: ARTIFICIAL
<220> FEATURE:
<223> OTHER INFORMATION: PCR primer

<400> SEQUENCE: 50
cccggtgagg actgtacaga ggacc                                            25

<210> SEQ ID NO 51
<211> LENGTH: 25
<212> TYPE: DNA
<213> ORGANISM: ARTIFICIAL
<220> FEATURE:
<223> OTHER INFORMATION: PCR primer

<400> SEQUENCE: 51
gagatgcttg agggatgctt gcgcc                                            25

<210> SEQ ID NO 52
<211> LENGTH: 25
<212> TYPE: DNA
<213> ORGANISM: ARTIFICIAL
<220> FEATURE:
<223> OTHER INFORMATION: PCR primer

<400> SEQUENCE: 52
aggatagcca ccattcgttg accgg                                            25

<210> SEQ ID NO 53
<211> LENGTH: 24
<212> TYPE: DNA
<213> ORGANISM: ARTIFICIAL
<220> FEATURE:
```

<223> OTHER INFORMATION: PCR primer

<400> SEQUENCE: 53
ctcagaccag cctgtattac gcgc                                            24

<210> SEQ ID NO 54
<211> LENGTH: 24
<212> TYPE: DNA
<213> ORGANISM: ARTIFICIAL
<220> FEATURE:
<223> OTHER INFORMATION: PCR primer

<400> SEQUENCE: 54
gcgactgcgt aacgctcacc agcg                                            24

<210> SEQ ID NO 55
<211> LENGTH: 24
<212> TYPE: DNA
<213> ORGANISM: ARTIFICIAL
<220> FEATURE:
<223> OTHER INFORMATION: PCR primer

<400> SEQUENCE: 55
gccggcactc ttactcatga cccg                                            24

<210> SEQ ID NO 56
<211> LENGTH: 24
<212> TYPE: DNA
<213> ORGANISM: ARTIFICIAL
<220> FEATURE:
<223> OTHER INFORMATION: PCR primer

<400> SEQUENCE: 56
gggtcgactg gtgtctcccc tacg                                            24

<210> SEQ ID NO 57
<211> LENGTH: 99
<212> TYPE: DNA
<213> ORGANISM: ARTIFICIAL
<220> FEATURE:
<223> OTHER INFORMATION: DNA oligo

<400> SEQUENCE: 57
gtaaaacggg tccattgggc acccgtaagc aaggagacat accccttgcg atgctcaaca     60
acctgcaggg tcaggcctac aaggtcaacc ctgaagttc                            99

<210> SEQ ID NO 58
<211> LENGTH: 89
<212> TYPE: DNA
<213> ORGANISM: ARTIFICIAL
<220> FEATURE:
<223> OTHER INFORMATION: DNA oligo

<400> SEQUENCE: 58
tccattgggc acccgtaagc aaggagacat accccttgcg atgctcaaca acctgcaggg     60
tcaggcctac aaggtcaacc ctgaagttc                                       89

<210> SEQ ID NO 59
<211> LENGTH: 79
<212> TYPE: DNA
<213> ORGANISM: ARTIFICIAL
<220> FEATURE:
<223> OTHER INFORMATION: DNA oligo

<400> SEQUENCE: 59

```
acccgtaagc aaggagacat accccttgcg atgctcaaca acctgcaggg tcaggcctac      60
aaggtcaacc ctgaagttc                                                  79
```

<210> SEQ ID NO 60
<211> LENGTH: 69
<212> TYPE: DNA
<213> ORGANISM: ARTIFICIAL
<220> FEATURE:
<223> OTHER INFORMATION: DNA oligo

<400> SEQUENCE: 60

```
aaggagacat accccttgcg atgctcaaca acctgcaggg tcaggcctac aaggtcaacc      60
ctgaagttc                                                             69
```

<210> SEQ ID NO 61
<211> LENGTH: 59
<212> TYPE: DNA
<213> ORGANISM: ARTIFICIAL
<220> FEATURE:
<223> OTHER INFORMATION: DNA oligo

<400> SEQUENCE: 61

```
accccttgcg atgctcaaca acctgcaggg tcaggcctac aaggtcaacc ctgaagttc       59
```

<210> SEQ ID NO 62
<211> LENGTH: 99
<212> TYPE: DNA
<213> ORGANISM: ARTIFICIAL
<220> FEATURE:
<223> OTHER INFORMATION: DNA oligo

<400> SEQUENCE: 62

```
gaacttcagg gttgaccttg taggcctgac cctgcaggtt gttgagcatc gcaaggggta      60
tgtctccttg cttacgggtg cccaatggac ccgttttac                            99
```

<210> SEQ ID NO 63
<211> LENGTH: 53
<212> TYPE: DNA
<213> ORGANISM: ARTIFICIAL
<220> FEATURE:
<223> OTHER INFORMATION: DNA oligo

<400> SEQUENCE: 63

```
ccattgggca cccgtaagca aggagacata ccccttgcga tgctcaacaa cct             53
```

<210> SEQ ID NO 64
<211> LENGTH: 52
<212> TYPE: DNA
<213> ORGANISM: ARTIFICIAL
<220> FEATURE:
<223> OTHER INFORMATION: DNA oligo

<400> SEQUENCE: 64

```
cattgggcac ccgtaagcaa ggagacatac cccttgcgat gctcaacaac ct              52
```

<210> SEQ ID NO 65
<211> LENGTH: 51
<212> TYPE: DNA
<213> ORGANISM: ARTIFICIAL
<220> FEATURE:
<223> OTHER INFORMATION: DNA oligo

<400> SEQUENCE: 65
attgggcacc cgtaagcaag gagacatacc ccttgcgatg ctcaacaacc t        51

<210> SEQ ID NO 66
<211> LENGTH: 50
<212> TYPE: DNA
<213> ORGANISM: ARTIFICIAL
<220> FEATURE:
<223> OTHER INFORMATION: DNA oligo

<400> SEQUENCE: 66
ttgggcaccc gtaagcaagg agacataccc cttgcgatgc tcaacaacct           50

<210> SEQ ID NO 67
<211> LENGTH: 49
<212> TYPE: DNA
<213> ORGANISM: ARTIFICIAL
<220> FEATURE:
<223> OTHER INFORMATION: DNA oligo

<400> SEQUENCE: 67
tgggcacccg taagcaagga gacataccccc ttgcgatgct caacaacct            49

<210> SEQ ID NO 68
<211> LENGTH: 48
<212> TYPE: DNA
<213> ORGANISM: ARTIFICIAL
<220> FEATURE:
<223> OTHER INFORMATION: DNA OLIGO

<400> SEQUENCE: 68
gggcacccgt aagcaaggag atacccct tgcgatgctc aacaacct                48

<210> SEQ ID NO 69
<211> LENGTH: 47
<212> TYPE: DNA
<213> ORGANISM: ARTIFICIAL
<220> FEATURE:
<223> OTHER INFORMATION: DNA oligo

<400> SEQUENCE: 69
ggcacccgta agcaaggaga catacccctt gcgatgctca acaacct                47

<210> SEQ ID NO 70
<211> LENGTH: 54
<212> TYPE: DNA
<213> ORGANISM: ARTIFICIAL
<220> FEATURE:
<223> OTHER INFORMATION: DNA oligo

<400> SEQUENCE: 70
aggttgttga gcatcgcaag gggtatgtct ccttgcttac gggtgcccaa tgga        54

<210> SEQ ID NO 71
<211> LENGTH: 55
<212> TYPE: DNA
<213> ORGANISM: ARTIFICIAL
<220> FEATURE:
<223> OTHER INFORMATION: DNA oligo

<400> SEQUENCE: 71
ggtattgggc acccgtaagg agaaccttaa ggtttaactt taagacccctt aagtg        55

<210> SEQ ID NO 72
<211> LENGTH: 55
<212> TYPE: DNA
<213> ORGANISM: ARTIFICIAL

<220> FEATURE:
<223> OTHER INFORMATION: DNA oligo

<400> SEQUENCE: 72
cacttaaggg tcttaaagtt aaaccttaag gttctcctta cgggtgccca atacc    55

<210> SEQ ID NO 73
<211> LENGTH: 55
<212> TYPE: DNA
<213> ORGANISM: ARTIFICIAL
<220> FEATURE:
<223> OTHER INFORMATION: DNA oligo

<400> SEQUENCE: 73
ggtattgggc acccgtaatg agaaccttaa ggtttaactt taagacccct aagtg    55

<210> SEQ ID NO 74
<211> LENGTH: 55
<212> TYPE: DNA
<213> ORGANISM: ARTIFICIAL
<220> FEATURE:
<223> OTHER INFORMATION: DNA oligo

<400> SEQUENCE: 74
cacttaaggg tcttaaagtt aaaccttaag gttctcatta cgggtgccca atacc    55

<210> SEQ ID NO 75
<211> LENGTH: 57
<212> TYPE: DNA
<213> ORGANISM: ARTIFICIAL
<220> FEATURE:
<223> OTHER INFORMATION: DNA oligo

<400> SEQUENCE: 75
ggttaatacg actcactata ggagaacctt aaggtttaac tttaagaccc ttaagtg    57

<210> SEQ ID NO 76
<211> LENGTH: 57
<212> TYPE: DNA
<213> ORGANISM: ARTIFICIAL
<220> FEATURE:
<223> OTHER INFORMATION: DNA oligo

<400> SEQUENCE: 76
cacttaaggg tcttaaagtt aaaccttaag gttctcctat agtgagtcgt attaacc    57

<210> SEQ ID NO 77
<211> LENGTH: 18
<212> TYPE: DNA
<213> ORGANISM: ARTIFICIAL
<220> FEATURE:
<223> OTHER INFORMATION: Transcription template

<400> SEQUENCE: 77
gccattgggc acccgtaa    18

<210> SEQ ID NO 78
<211> LENGTH: 18
<212> TYPE: DNA
<213> ORGANISM: ARTIFICIAL
<220> FEATURE:
<223> OTHER INFORMATION: Nucleotides in Syn5 RNA polymerase gene
      (No.808-825)

<400> SEQUENCE: 78
ccattgggca cccgtaag    18

<210> SEQ ID NO 79
<211> LENGTH: 6
<212> TYPE: PRT
<213> ORGANISM: ARTIFICIAL
<220> FEATURE:
<223> OTHER INFORMATION: Syn5 RNA polymerase gene PROTEINS

<400> SEQUENCE: 79

Pro Leu Gly Thr Arg Lys
1               5

<210> SEQ ID NO 80
<211> LENGTH: 18
<212> TYPE: DNA
<213> ORGANISM: ARTIFICIAL
<220> FEATURE:
<223> OTHER INFORMATION: Syn5 RNA polymerase gene mutated

<400> SEQUENCE: 80
cctcttggta cgcgcaag                                                     18

<210> SEQ ID NO 81
<211> LENGTH: 15
<212> TYPE: DNA
<213> ORGANISM: ARTIFICIAL
<220> FEATURE:
<223> OTHER INFORMATION: Syn5 promoter

<400> SEQUENCE: 81
attgggcacc cgtaa                                                        15

<210> SEQ ID NO 82
<211> LENGTH: 12
<212> TYPE: RNA
<213> ORGANISM: Artificial
<220> FEATURE:
<223> OTHER INFORMATION: Syn5 RP Figure 28C.

<400> SEQUENCE: 82
cagagaauag uu                                                           12

<210> SEQ ID NO 83
<211> LENGTH: 2340
<212> TYPE: DNA
<213> ORGANISM: ARTIFICIAL
<220> FEATURE:
<223> OTHER INFORMATION: Syn5 RNAP-NP

<400> SEQUENCE: 83
atgtccttcg atctcatcgc tcgccagctt cagcgtgaga ccgaggccgc ggagctggcc        60
cgcaagcgtc tacaagacgc ccgacgcgag gccaatgaac gctcctatgc ctcaagcaac       120
atcgagagcc gcaaggccat cgcgacgttc ctggatccca tcgcccaacg catcggcgaa       180
cgcctgttca cgctacggcg tggtactggt gcagttgatg ccgccgaggt ctacaagcat       240
ctgaagaacg ccgatcacca tcatctggcg ctcatcacga tgaagacagc cctggacgtc       300
ctgggcaaag atcccgagcc acagatccaa cagctgacca cagccattgg ccgcaacatc       360
cagctggagc tccgcctcac gtactacgcc gaggaaaacc cggagctcta caaacaggcc       420
tcccgcttct tccacgcagg cactggcacc cgccagaaag ccacggtgat caaactcaag       480
ttcaaccgcg agggcattga gtgggaccaa tggtcccgcg tcacctgtca caggttggc        540 caatggctca tgttggctat ggccgacgtc accggctgga ttgaacgggc aaccgaccga       600

-continued

```
accagtggag gacgcaaaac caagacccgc atctgctact cccgcgagtt cttgcagcat    660
cgggacacaa tcctcgcagc agctgagcag ttggccttct gccagtggcc catgctttgc    720
cctcccattg agtggtccaa cgaccacaac ggtgggtacc tgagcgaaca gatccggcgg    780
gtcaatccgc tgattcgtaa aacgggtcct cttggtacgc gcaagcaagg agacataccc    840
cttgcgatgc tcaacaacct gcagggtcag gcctacaagg tcaaccctga agttctcgac    900
atagcgaacc actgctacga gtccaacgtg accgtaggca agttcatacg ccacgctccc    960
ctacctgttc caccatcacc cggtgaggac tgtacagagg accagctcac agcctataaa   1020
cgggcacgac gtgaggccga ggacttcaac gcacagatca gtcagaagaa ctggcgcacg   1080
accgaggtca tgtatgtggc ccgcaagtac gccgacgagg cctccttctg gatgcccgcc   1140
agcttcgact atcgcggccg tgtttacttt ctgaacactg ccctcaaccc gcaggggact   1200
gacttcgaca aggcgctcct ttacttcgct gaggagggtc cggtcaacga atggtggcta   1260
tccttccacg tcgcgaccac ctacggcctc gacaaggaga ccatggtcaa ccgggtccaa   1320
tgggctcggg acaaccacga gctcatcgat cgcatcgcct ctgaccccgt ccgccatacc   1380
gagtggcacg acgctgacga gccctggtgc ttcctggctg cctgcctcga gtacaaggcc   1440
tgcgtgatcg atggcaccaa acagaccagc ggcctcccta tcgggatcga cgccacctgt   1500
tcaggcctgc agcacctcgc tgctatgacc cgctgcggac gcacagccgc cctggtcaac   1560
gtgacaccga ccgacaagcc ggccgatgct acaagaccg tggcgcaagc atccctcaag   1620
catctcccca aggagcagca cgagtggatc acccgcaagg tcaccaaaag gcccgtcatg   1680
tgcacaccct acggggtgac catgtcatcg gcccgcggct acatccgcga tcagctggtg   1740
aaggacggcc acaaggagga cctccgatct cctggcgtgc tcaacggcat cgtcaaggcg   1800
atctttaatg aggccatccc tgaggtcatc cccgccccg tgcaggtcat ggcctggctc   1860
aagcgttcag ctggtcagat catcgaccgg ggtgattcca ccatcacgtg gaccacgccc   1920
tcaggcttcg aggttgttca agacctcaaa aagtccaaga cctacgaggt caagacccgc   1980
atcatgggcg agcacggat caagctccaa gtgggcgacg ggttcaccga cgagcccgac   2040
cgtgaccacc acaaaagcgc actggctccc aacgtggtgc acagcaacga tgcgtctctc   2100
ctccacctga ccttcgcctt ctgggacaag cccttcacgg tcatccatga ctgtgtcctg   2160
ggccgttcct gcgacatgga tcagatgggc tccgacatcc ggcttcattt cgccgagatg   2220
tacaaggccg acgtgatgca agactgggcc gaccaggtgg gcgttgagct ccctgtcgac   2280
ctgatcaaaa acacgctcga catcgacagc gtcaaccagt cccttactt cttctcctga   2340
```

<210> SEQ ID NO 84
<211> LENGTH: 17
<212> TYPE: DNA
<213> ORGANISM: Artificial
<220> FEATURE:
<223> OTHER INFORMATION: chain terminator to sequence the 5 prime end of Syn5 RNAP transcript on a template same as template 1 in Figure 2B lane 4

<400> SEQUENCE: 84
aaggagacat acccctt                                                    17

<210> SEQ ID NO 85
<211> LENGTH: 27
<212> TYPE: DNA
<213> ORGANISM: Artificial
<220> FEATURE:

<223> OTHER INFORMATION: chain terminator to sequence the 5 prime end of
     Syn5 RNAP transcript on a template same as template 1 in Figure 2B
     lane 3

<400> SEQUENCE: 85
acccgtaagc aaggagacat acccctt                                          27

<210> SEQ ID NO 86
<211> LENGTH: 37
<212> TYPE: DNA
<213> ORGANISM: Artificial
<220> FEATURE:
<223> OTHER INFORMATION: chain terminator to sequence the 5 prime end of
     Syn5 RNAP transcript on a template same as template 1 in Figure 2B
     lane 2

<400> SEQUENCE: 86
tccattgggc acccgtaagc aaggagacat acccctt                               37

<210> SEQ ID NO 87
<211> LENGTH: 47
<212> TYPE: DNA
<213> ORGANISM: Artificial
<220> FEATURE:
<223> OTHER INFORMATION: chain terminator to sequence the 5 prime end of
     Syn5 RNAP transcript on a template same as template 1 in Figure 2B
     lane 1

<400> SEQUENCE: 87
gtaaaacggg tccattgggc acccgtaagc aaggagacat acccctt                    47

<210> SEQ ID NO 88
<211> LENGTH: 47
<212> TYPE: DNA
<213> ORGANISM: Artificial
<220> FEATURE:
<223> OTHER INFORMATION: Drawing 2B lane 1 gray complimentary gray
     sequence 5 prime to 3 prime reverse

<400> SEQUENCE: 88
aaggggtatg tctccttgct tacgggtgcc caatggaccc gttttac                    47

<210> SEQ ID NO 89
<211> LENGTH: 47
<212> TYPE: DNA
<213> ORGANISM: Artificial
<220> FEATURE:
<223> OTHER INFORMATION: Determination of the 5 prime end of the Syn5
     Promoter lane 7

<400> SEQUENCE: 89
ggcacccgta agcaaggaga catacccctt gcgatgctca acaacct                    47

<210> SEQ ID NO 90
<211> LENGTH: 48
<212> TYPE: DNA
<213> ORGANISM: Artificial
<220> FEATURE:
<223> OTHER INFORMATION: Determination of the 5 prime end of the Syn5
     Promoter LANE 6

<400> SEQUENCE: 90
gggcacccgt aagcaaggag acatacccct tgcgatgctc aacaacct                   48

<210> SEQ ID NO 91
<211> LENGTH: 49
<212> TYPE: DNA

```
<213> ORGANISM: Artificial
<220> FEATURE:
<223> OTHER INFORMATION: FIGURE 2C LANE 5 Determination of the 5 prime
      end of the Syn5 Promoter

<400> SEQUENCE: 91
tgggcacccg taagcaagga gacatacccc ttgcgatgct caacaacct            49

<210> SEQ ID NO 92
<211> LENGTH: 50
<212> TYPE: DNA
<213> ORGANISM: Artificial
<220> FEATURE:
<223> OTHER INFORMATION: Determination of the 5 prime end of the Syn5
      Promoter figure 2C lane 4

<400> SEQUENCE: 92
ttgggcaccc gtaagcaagg agacatacce cttgcgatgc tcaacaacct           50

<210> SEQ ID NO 93
<211> LENGTH: 51
<212> TYPE: DNA
<213> ORGANISM: Artificial
<220> FEATURE:
<223> OTHER INFORMATION: Determination of the 5 prime end of the Syn5
      Promoter lane 3

<400> SEQUENCE: 93
attgggcacc cgtaagcaag gagacatacc ccttgcgatg ctcaacaacc t         51

<210> SEQ ID NO 94
<211> LENGTH: 52
<212> TYPE: DNA
<213> ORGANISM: Artificial
<220> FEATURE:
<223> OTHER INFORMATION: Determination of the 5 prime end of the Syn5
      Promoter lane 2

<400> SEQUENCE: 94
cattgggcac ccgtaagcaa ggagacatac cccttgcgat gctcaacaac ct        52

<210> SEQ ID NO 95
<211> LENGTH: 53
<212> TYPE: DNA
<213> ORGANISM: Artificial
<220> FEATURE:
<223> OTHER INFORMATION: Determination of the 5 prime end of the Syn5
      Promoter lane 1

<400> SEQUENCE: 95
ccattgggca cccgtaagca aggagacata ccccttgcga tgctcaacaa cct       53

<210> SEQ ID NO 96
<211> LENGTH: 54
<212> TYPE: DNA
<213> ORGANISM: ARTIFICIAL
<220> FEATURE:
<223> OTHER INFORMATION: COMPLIMENTARY 5 PRIME nucleotide of the
      promoter in this 46 nt region FIGURE 2C LANE 1

<400> SEQUENCE: 96
aggttgttga gcatcgcaag gggtatgtct ccttgcttac gggtgcccaa tgga      54

<210> SEQ ID NO 97
<211> LENGTH: 11
<212> TYPE: DNA
<213> ORGANISM: Artificial
```

```
<220> FEATURE:
<223> OTHER INFORMATION: Syn5 RNAP figure 3A

<400> SEQUENCE: 97
gcaaggagac a                                                              11

<210> SEQ ID NO 98
<211> LENGTH: 47
<212> TYPE: DNA
<213> ORGANISM: Artificial
<220> FEATURE:
<223> OTHER INFORMATION: Syn5 RNAP figure 3A

<400> SEQUENCE: 98
gtaaaacggg tccattgggc acccgtaagc aaggagacat acccctt                       47

<210> SEQ ID NO 99
<211> LENGTH: 47
<212> TYPE: DNA
<213> ORGANISM: Artificial
<220> FEATURE:
<223> OTHER INFORMATION: Complimentary strand Syn5 RNAP figure 3A

<400> SEQUENCE: 99
aaggggtatg tctccttgct tacgggtgcc caatggaccc gttttac                       47

<210> SEQ ID NO 100
<211> LENGTH: 16
<212> TYPE: DNA
<213> ORGANISM: Artificial
<220> FEATURE:
<223> OTHER INFORMATION: G follows Syn5 promoter

<400> SEQUENCE: 100
attgggcacc cgtaag                                                         16

<210> SEQ ID NO 101
<211> LENGTH: 16
<212> TYPE: DNA
<213> ORGANISM: Artificial
<220> FEATURE:
<223> OTHER INFORMATION: T follows Syn5 promoter

<400> SEQUENCE: 101
attgggcacc cgtaat                                                         16

<210> SEQ ID NO 102
<211> LENGTH: 18
<212> TYPE: DNA
<213> ORGANISM: Artificial
<220> FEATURE:
<223> OTHER INFORMATION: T7 Promoter 1.1B

<400> SEQUENCE: 102
taatacgact cactatag                                                       18

<210> SEQ ID NO 103
<211> LENGTH: 18
<212> TYPE: DNA
<213> ORGANISM: Artificial
<220> FEATURE:
<223> OTHER INFORMATION: Original sequence Figure 16

<400> SEQUENCE: 103
ccattgggca cccgtaag                                                       18
```

```
<210> SEQ ID NO 104
<211> LENGTH: 18
<212> TYPE: DNA
<213> ORGANISM: Artificial
<220> FEATURE:
<223> OTHER INFORMATION: Modified sequence Figure 16

<400> SEQUENCE: 104
cctcttggta cgcgcaag                                                 18

<210> SEQ ID NO 105
<211> LENGTH: 6
<212> TYPE: PRT
<213> ORGANISM: Artificial
<220> FEATURE:
<223> OTHER INFORMATION: AA Encoded Figure 16

<400> SEQUENCE: 105

Pro Leu Gly Thr Arg Lys
1               5

<210> SEQ ID NO 106
<211> LENGTH: 12
<212> TYPE: RNA
<213> ORGANISM: Artificial
<220> FEATURE:
<223> OTHER INFORMATION: Incorporation of 2 prime-F-dNTP into RNA using
      WT Syn5 RNA polymerase Figure 24

<400> SEQUENCE: 106
ggagaaccuu aa                                                       12

<210> SEQ ID NO 107
<211> LENGTH: 12
<212> TYPE: RNA
<213> ORGANISM: Artificial
<220> FEATURE:
<223> OTHER INFORMATION: Incorporation of 2 prime-F-dNTP into RNA using
      WT Syn5 RNA polymerase Figure 24

<400> SEQUENCE: 107
gggagagagc au                                                       12

<210> SEQ ID NO 108
<211> LENGTH: 12
<212> TYPE: RNA
<213> ORGANISM: Artificial
<220> FEATURE:
<223> OTHER INFORMATION: Incorporation of 2 prime-F-dNTP into RNA using
      WT Syn5 RNA polymerase Figure 24

<400> SEQUENCE: 108
cagagaauag uu                                                       12

<210> SEQ ID NO 109
<211> LENGTH: 46
<212> TYPE: PRT
<213> ORGANISM: Artificial
<220> FEATURE:
<223> OTHER INFORMATION: T7 figure 26

<400> SEQUENCE: 109

Glu Ile Ser Glu Lys Val Lys Leu Gly Thr Lys Ala Leu Ala Gly Gln
1               5                   10                  15

Trp Leu Ala Tyr Gly Val Thr Arg Ser Val Thr Lys Arg Ser Val Met
                20                  25                  30
```

Thr Leu Ala Tyr Gly Ser Lys Glu Phe Gly Phe Arg Gln Gln
         35                  40                  45

<210> SEQ ID NO 110
<211> LENGTH: 31
<212> TYPE: PRT
<213> ORGANISM: Artificial
<220> FEATURE:
<223> OTHER INFORMATION: Cyanophage Syn5 Figure 25B.

<400> SEQUENCE: 110

Glu Trp Ile Thr Arg Lys Val Thr Lys Arg Pro Val Met Cys Thr Pro
1               5                   10                  15

Tyr Gly Val Thr Met Ser Ser Ala Arg Gly Tyr Ile Arg Asp Gln
            20                  25                  30

<210> SEQ ID NO 111
<211> LENGTH: 47
<212> TYPE: PRT
<213> ORGANISM: Artificial
<220> FEATURE:
<223> OTHER INFORMATION: Concensus figure 25B.
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (17)..(20)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (27)..(32)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid

<400> SEQUENCE: 111

Glu Trp Ile Xaa Xaa Lys Val Lys Leu Gly Thr Lys Xaa Xaa Xaa Gly
1               5                   10                  15

Xaa Xaa Xaa Xaa Tyr Gly Val Thr Xaa Ser Xaa Ala Xaa Xaa Xaa Xaa
            20                  25                  30

Met Thr Leu Ala Tyr Gly Ser Lys Glu Phe Gly Phe Arg Xaa Gln
         35                  40                  45

<210> SEQ ID NO 112
<211> LENGTH: 40
<212> TYPE: PRT
<213> ORGANISM: Artificial
<220> FEATURE:
<223> OTHER INFORMATION: SP6 RNA polymerase figure 25B.

<400> SEQUENCE: 112

Met Ala Ser Ala Trp Asp Ser Ile Gly Ile Thr Arg Ser Leu Thr Lys
1               5                   10                  15

Lys Pro Val Met Thr Leu Pro Tyr Gly Ser Thr Arg Leu Thr Cys Arg
            20                  25                  30

```
Glu Ser Val Ile Asp Tyr Ile Val
        35              40

<210> SEQ ID NO 113
<211> LENGTH: 36
<212> TYPE: PRT
<213> ORGANISM: Artificial
<220> FEATURE:
<223> OTHER INFORMATION: T7 RNAP figure 26

<400> SEQUENCE: 113

Leu Ala Gly Gln Trp Leu Ala Tyr Gly Val Thr Arg Ser Val Thr Lys
1               5                   10                  15

Arg Ser Val Met Thr Leu Ala Tyr Gly Ser Lys Glu Phe Gly Phe Arg
            20                  25                  30

Gln Gln Val Leu
        35

<210> SEQ ID NO 114
<211> LENGTH: 31
<212> TYPE: PRT
<213> ORGANISM: Artificial
<220> FEATURE:
<223> OTHER INFORMATION: Syn5 RNAP figure 26

<400> SEQUENCE: 114

His Glu Trp Ile Thr Arg Lys Val Thr Lys Arg Pro Val Met Cys Thr
1               5                   10                  15

Pro Tyr Gly Val Thr Met Ser Ser Ala Arg Gly Tyr Ile Arg Asp
            20                  25                  30

<210> SEQ ID NO 115
<211> LENGTH: 37
<212> TYPE: PRT
<213> ORGANISM: Artificial
<220> FEATURE:
<223> OTHER INFORMATION: Consensus figure 26.
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: misc_feature
<222> LOCATION: (28)..(31)
<223> OTHER INFORMATION: Xaa can be any naturally occurring amino acid
<220> FEATURE:
<221> NAME/KEY: misc_feature
<222> LOCATION: (33)..(34)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid

<400> SEQUENCE: 115

Xaa Ala Xaa Xaa Trp Xaa Xaa Xaa Gly Ile Thr Arg Ser Val Thr Lys
1               5                   10                  15

Arg Pro Val Met Thr Leu Pro Tyr Gly Ser Thr Xaa Xaa Xaa Xaa Arg
            20                  25                  30

Xaa Xaa Val Xaa Asp
```

```
<210> SEQ ID NO 116
<211> LENGTH: 12
<212> TYPE: RNA
<213> ORGANISM: Artificial
<220> FEATURE:
<223> OTHER INFORMATION: Syn5 RNA polymerase Figure 28B.

<400> SEQUENCE: 116
gggucuagag uc                                                             12
```